United States Patent
Park et al.

(10) Patent No.: US 10,808,255 B2
(45) Date of Patent: Oct. 20, 2020

(54) PROMOTER SYSTEM INDUCING EXPRESSION BY 3-HYDROXYPROPIONIC ACID AND METHOD FOR BIOLOGICAL PRODUCTION OF 3-HYDROXYPROPIONIC ACID USING SAME

(71) Applicants: NOROO IC Co., Ltd., Suwanee, GA (US); NOROO R&C CO., LTD., Ansan-si, Gyeonggi-do (KR)

(72) Inventors: Sung-Hoon Park, Busan (KR); Shengfang Zhou, Busan (KR); Somasundar Ashok, Busan (KR); Eun Hee Seol, Busan (KR); Satish Kumar Ainala, Busan (KR)

(73) Assignees: NOROO IC CO., LTD., Suwanee, GA (US); NOROO R&C CO., LTD., Ansan-si, Gyeonggi-Do (KR)

( * ) Notice: Subject to any disclaimer, the term of this patent is extended or adjusted under 35 U.S.C. 154(b) by 238 days.

(21) Appl. No.: 15/735,585

(22) PCT Filed: Jun. 13, 2016

(86) PCT No.: PCT/KR2016/006261
§ 371 (c)(1),
(2) Date: May 24, 2018

(87) PCT Pub. No.: WO2016/200239
PCT Pub. Date: Dec. 15, 2016

(65) Prior Publication Data
US 2018/0312852 A1    Nov. 1, 2018

(30) Foreign Application Priority Data

Jun. 11, 2015 (KR) ........................ 10-2015-0082593
Jun. 13, 2016 (KR) ........................ 10-2016-0073091

(51) Int. Cl.
| C12N 15/74 | (2006.01) |
| C12N 15/78 | (2006.01) |
| C12P 7/52  | (2006.01) |
| C12P 7/62  | (2006.01) |

(52) U.S. Cl.
CPC ............ *C12N 15/74* (2013.01); *C12N 15/78* (2013.01); *C12P 7/52* (2013.01); *C12P 7/62* (2013.01)

(58) Field of Classification Search
CPC .................................. C12N 15/74; C12P 7/62
USPC ........................... 435/141, 146, 254.2, 253.2
See application file for complete search history.

(56) References Cited

U.S. PATENT DOCUMENTS 8,883,464 B2    11/2014  Lynch et al.
9,428,778 B2 *   8/2016  Lynch .................... A61L 15/24
2012/0135481 A1  5/2012  Jessen et al.

FOREIGN PATENT DOCUMENTS

| JP | 2013-542747 A | 11/2013 |
| KR | 10-1437042 B1 | 9/2014  |

OTHER PUBLICATIONS

International Search Report for PCT/KR2016/006261 dated Oct. 6, 2016 from Korean Intellectual Property Office.
Zhou, Shengfang et al., "Development of a deletion mutant of Pseudomonas denitrificans that does not degrade 3-hydroxypropionic acid", Applied Microbiology and Biotechnology, 2014, vol. 98, No. 10, pp. 4389-4398.
Zhou, Shengfang et al., "Cloning, Expression and Characterization of 3-Hydroxyisobutyrate Dehydrogenase from Pseudomonas denitrificans ATCC 13867", PloS One, 2013, vol. 8, No. 5, e62666 (inner pp. 1-11).
Zhou, Shengfang et al., "Inducible gene expression system by 3-hydroxypropionic acid", Biotechnology for Biofuels, (2015) 8:169.

* cited by examiner

*Primary Examiner* — Tekchand Saidha
(74) *Attorney, Agent, or Firm* — Revolution IP, PLLC

(57) ABSTRACT

The present invention relates to a promoter system inducing expression of 3-hydroxypropionic acid (3-HP) and a method of biologically producing 3-HP using the same. To improve production of 3-HP in a biological manner, continuous synthesis of new enzymes having enzyme activity is necessary. As a result of screening 3-HP reactive transcription regulators and 3-HP reactive promoters from several microorganisms including *Pseudomonas denitrificans*, it was confirmed that the transcriptions regulations and promoters are composed of LysR proteins and particular gene nucleotide sequences binding to the LysR proteins. Therefore, the 3-HP inducible system is expected to be effectively used to regulate 3-HP metabolic pathways.

13 Claims, 24 Drawing Sheets

Specification includes a Sequence Listing.

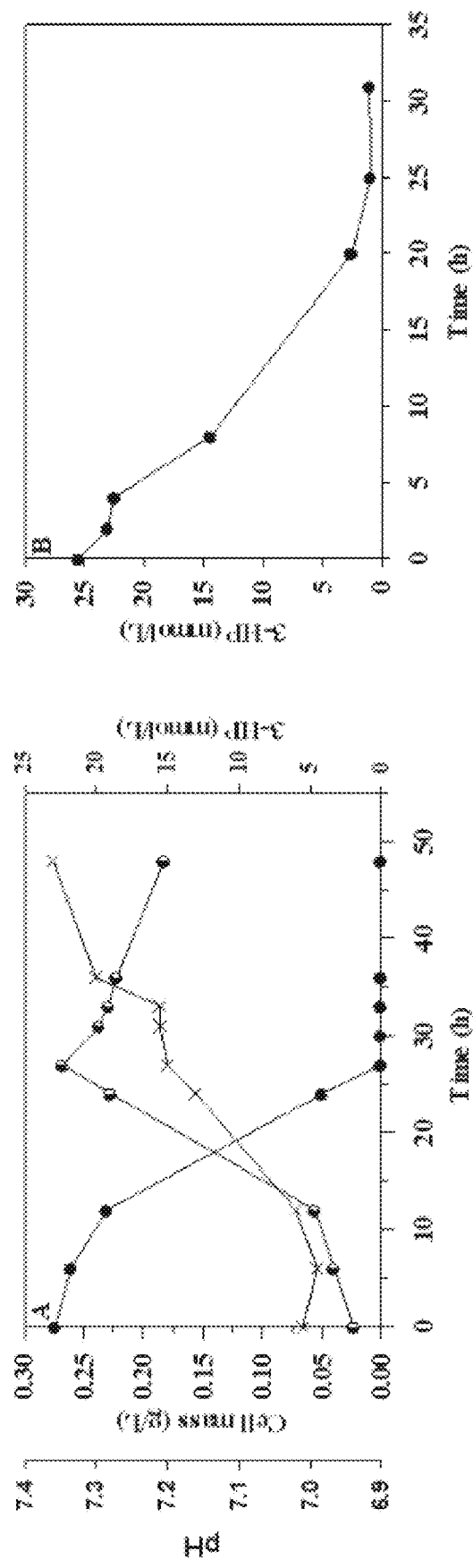
[FIG. 1]

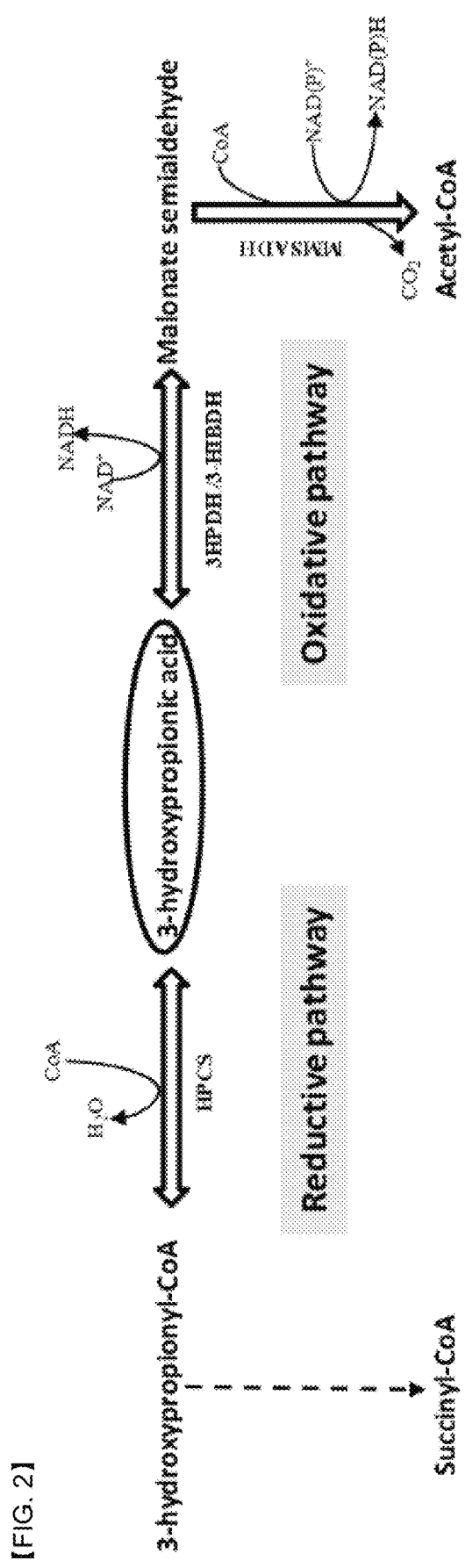
[FIG. 2]

[FIG. 3]
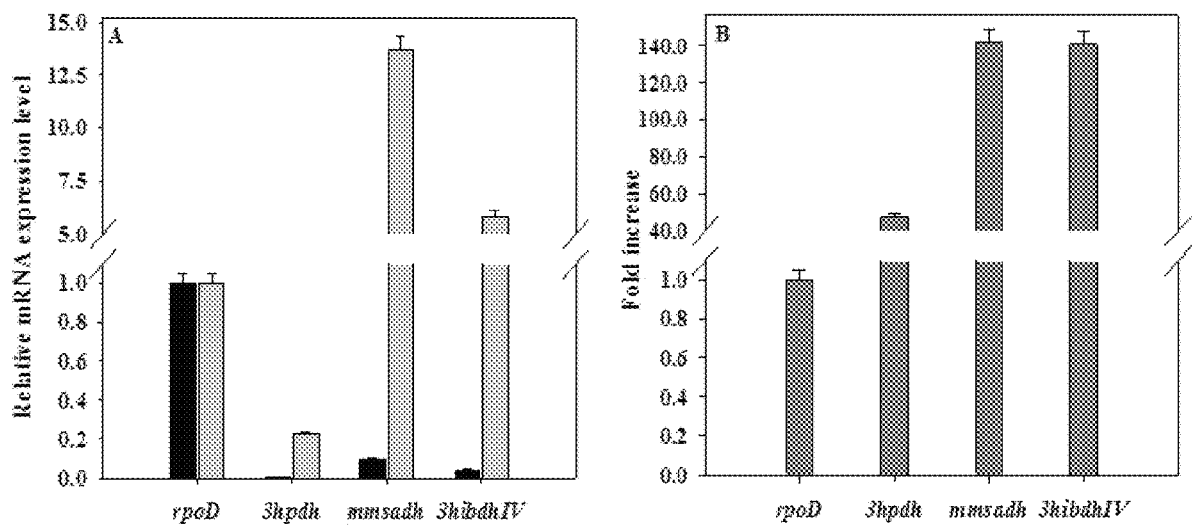
[FIG. 4]
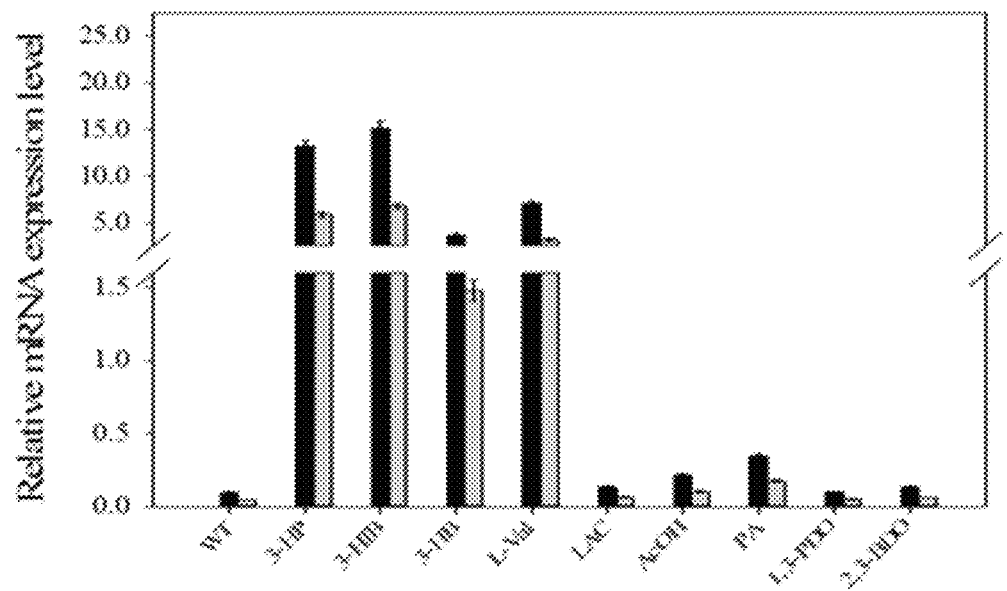

[FIG. 5]
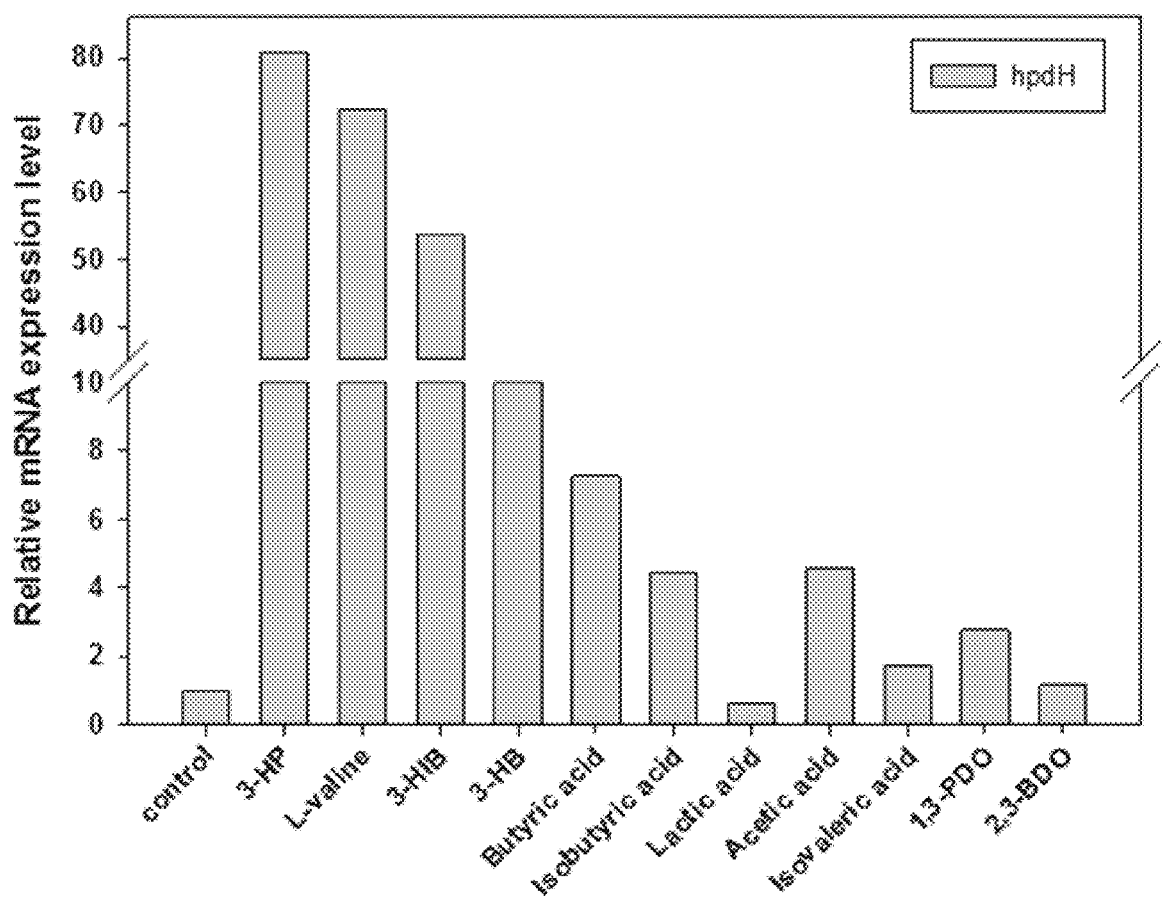

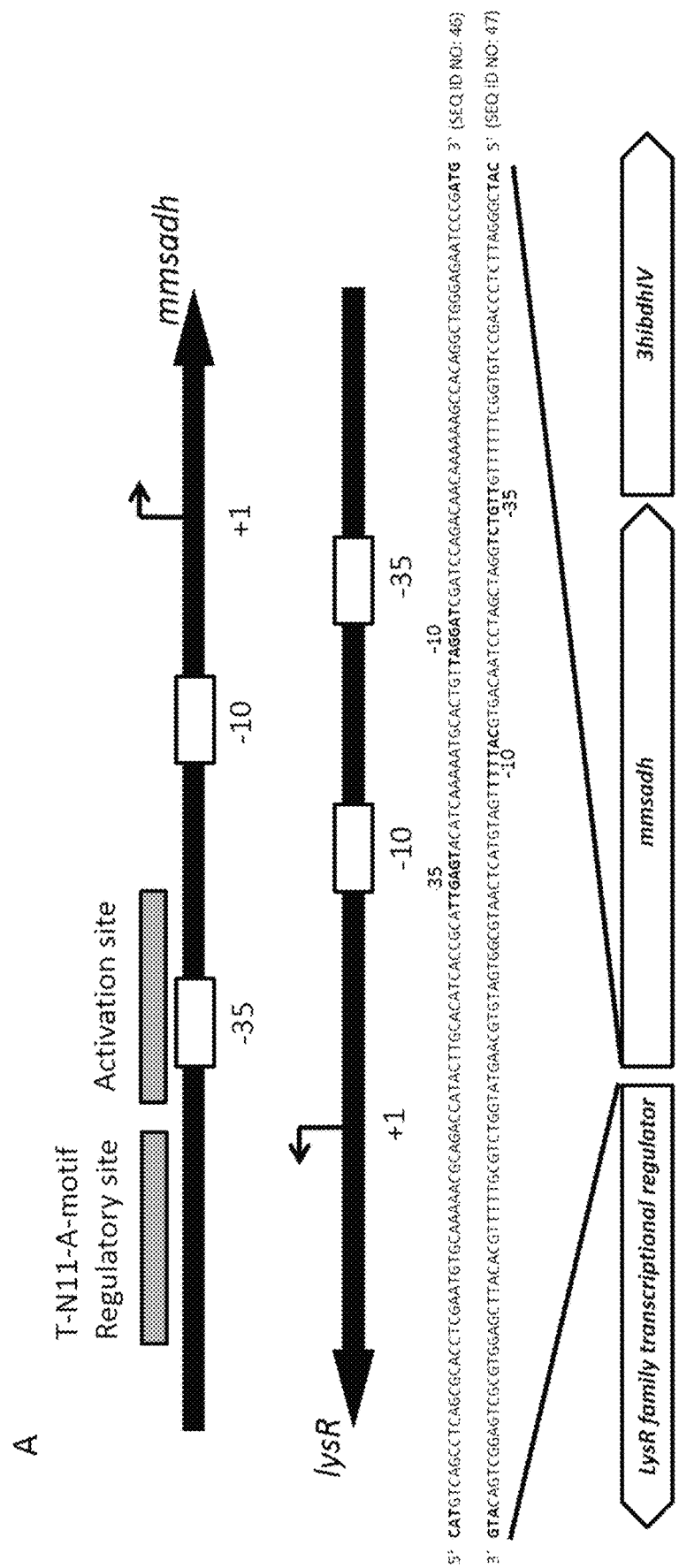

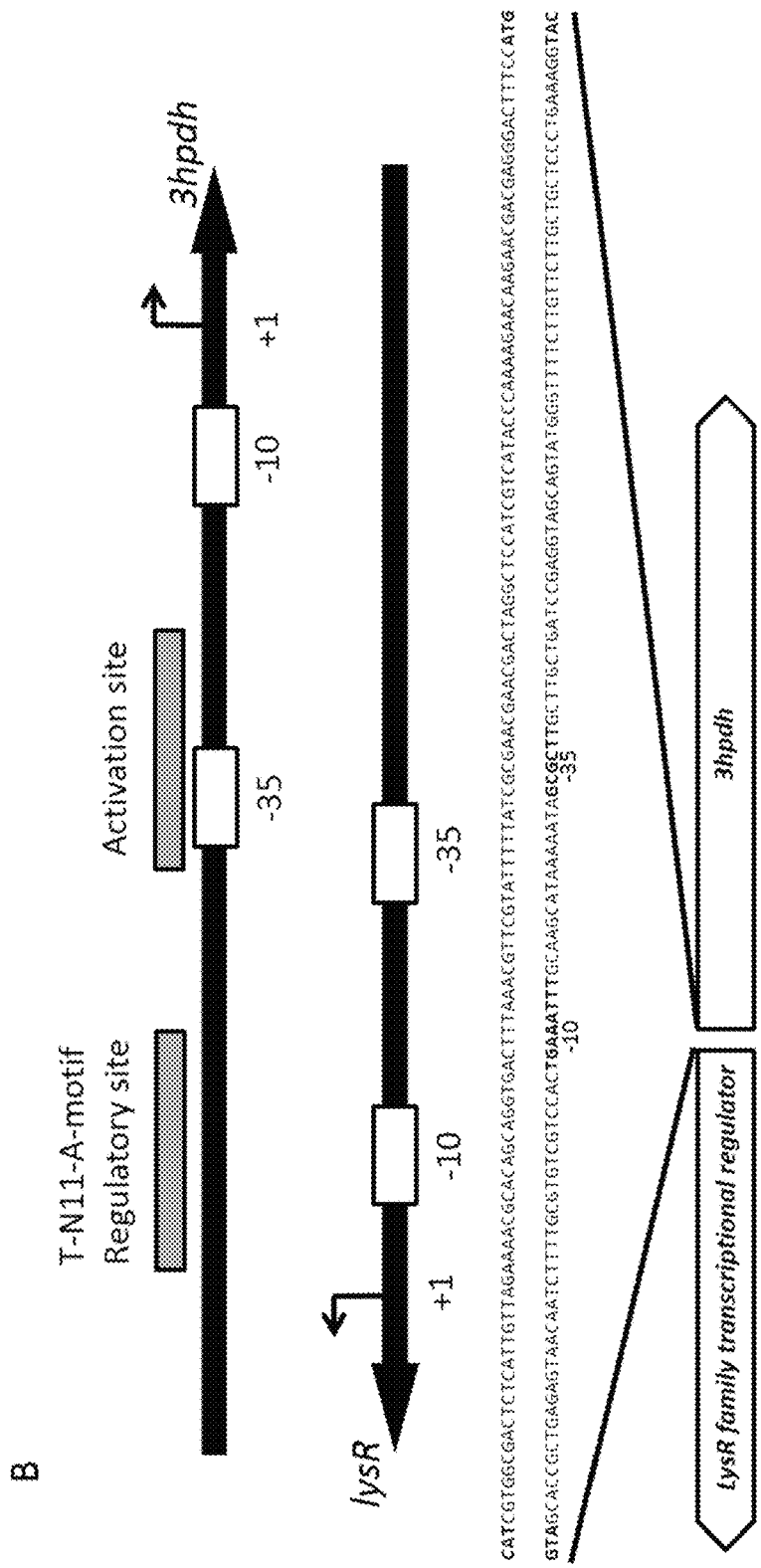
[FIG. 6b]

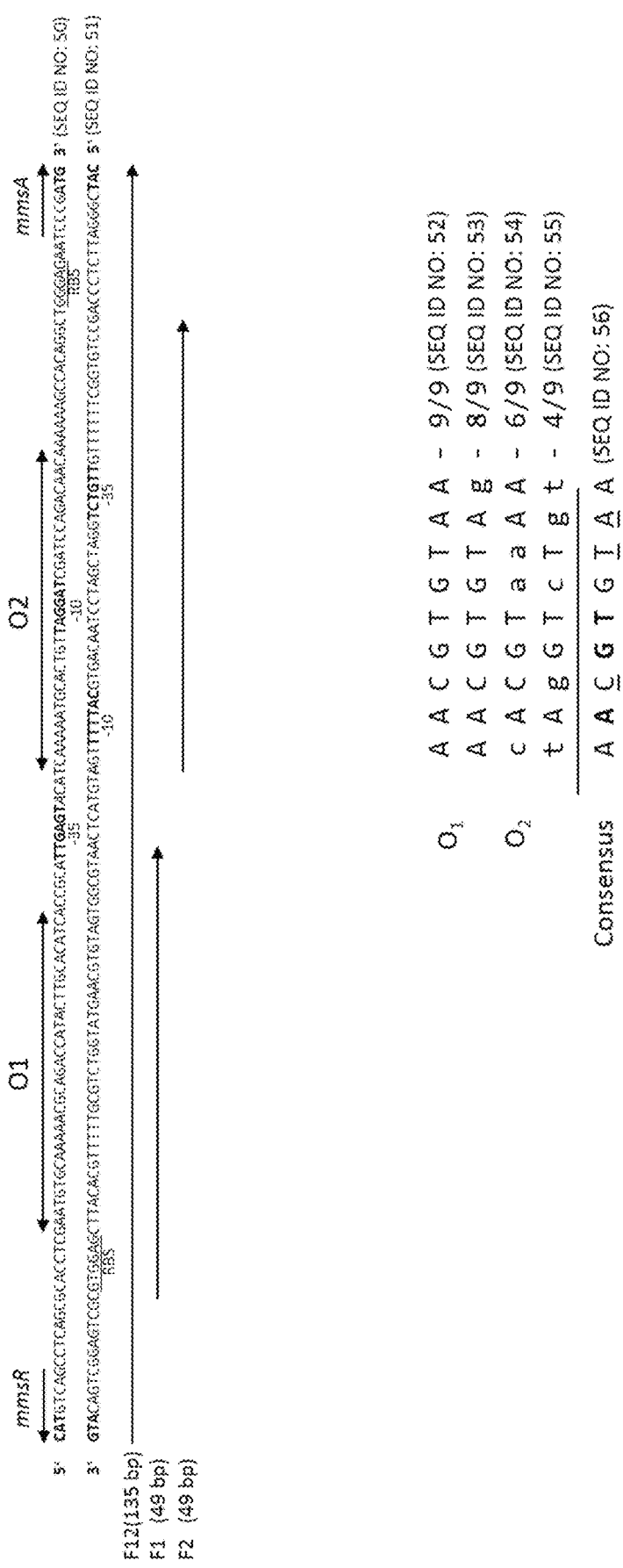
[FIG. 7]

[FIG. 8]
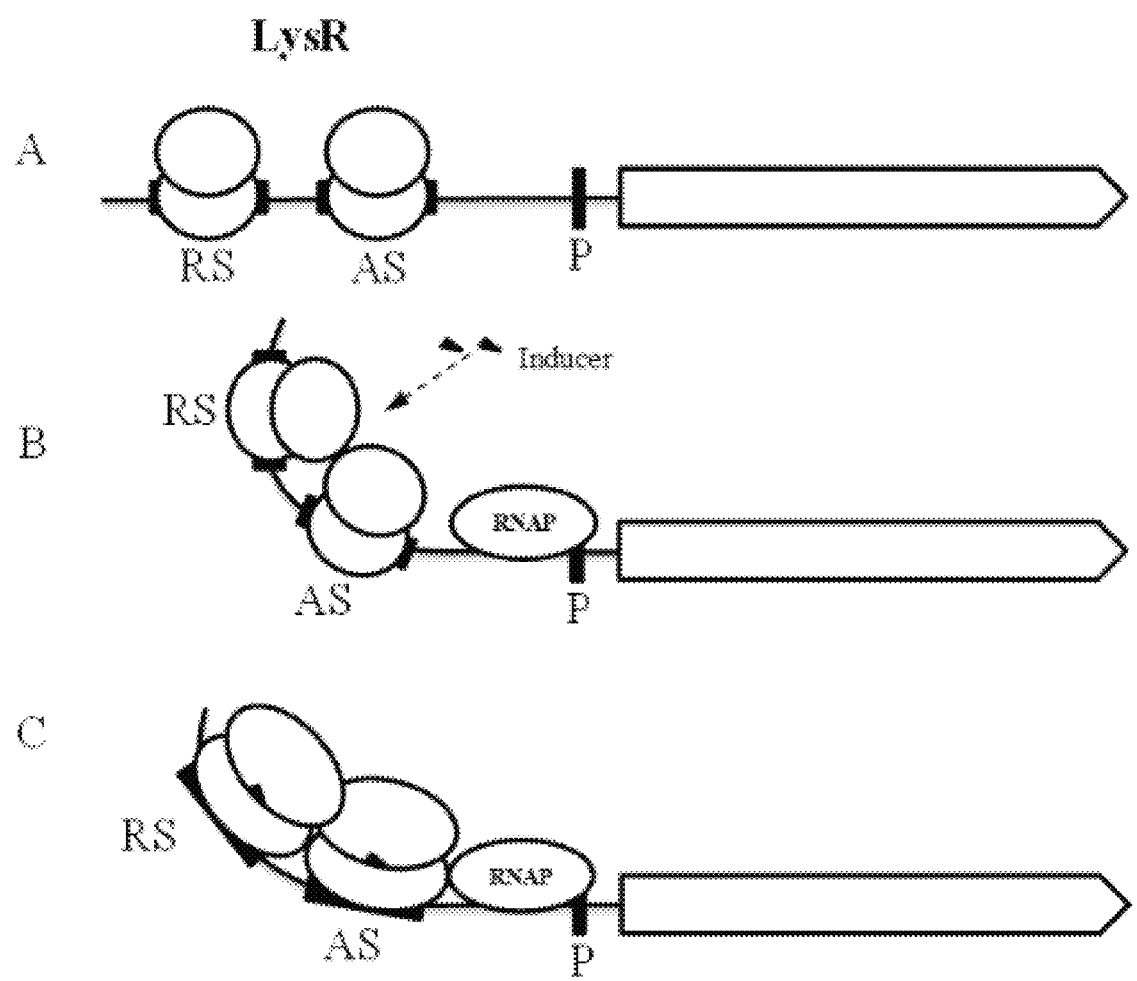

[FIG. 9]
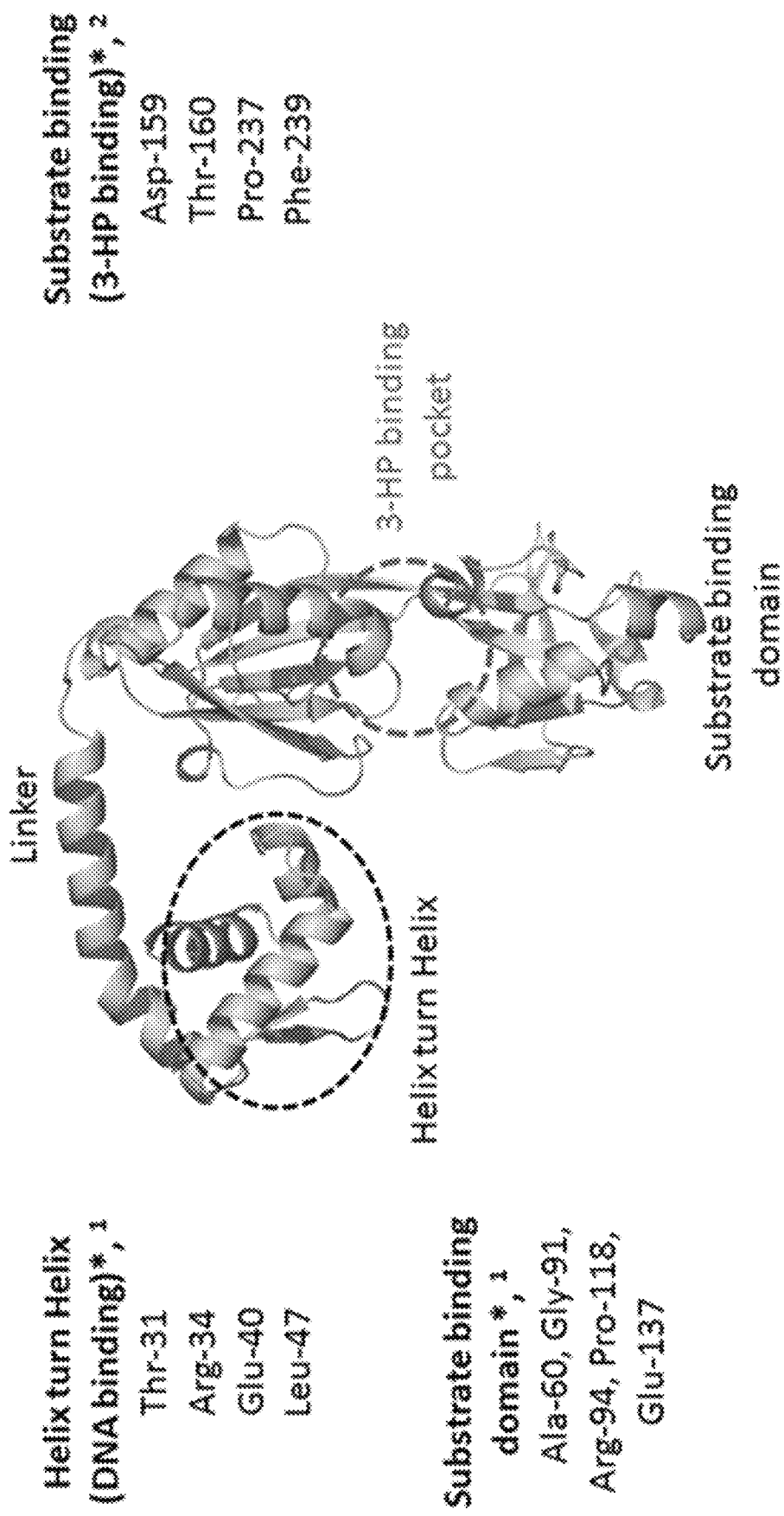
**Helix turn Helix (DNA binding)\*, ¹**
Thr-31
Arg-34
Glu-40
Leu-47
**Substrate binding domain\*, ¹**
Ala-60, Gly-91,
Arg-94, Pro-118,
Glu-137
**Substrate binding (3-HP binding)\*, ²**
Asp-159
Thr-160
Pro-237
Phe-239
\* Highly conserved residues with reference to C4-LysR in *P. denitrificans*.
¹ Proposed based on Multiple Sequence Alignment of LysR from 62 different genus; and
² based on molecular modeling, docking and MSA.

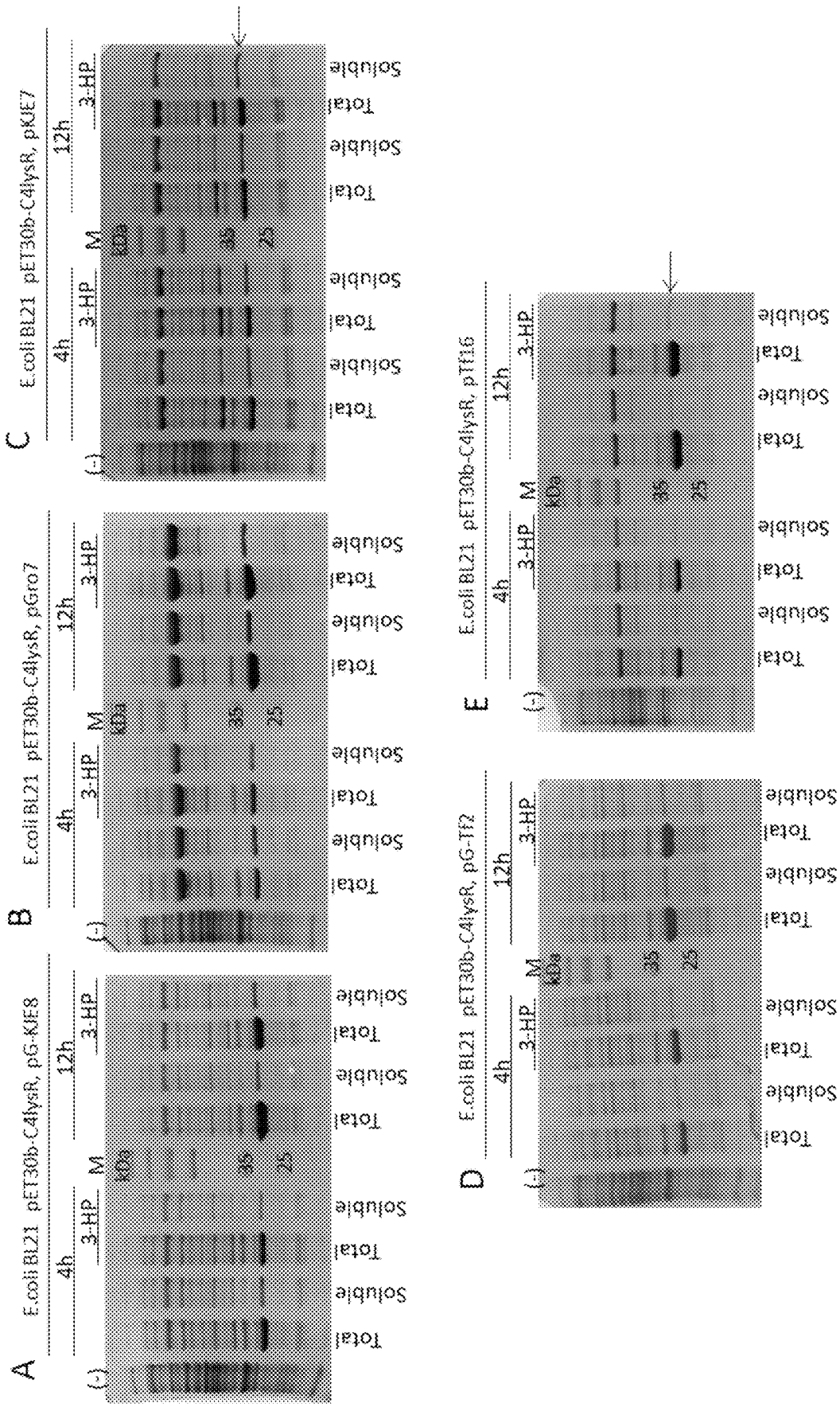
[FIG. 10]

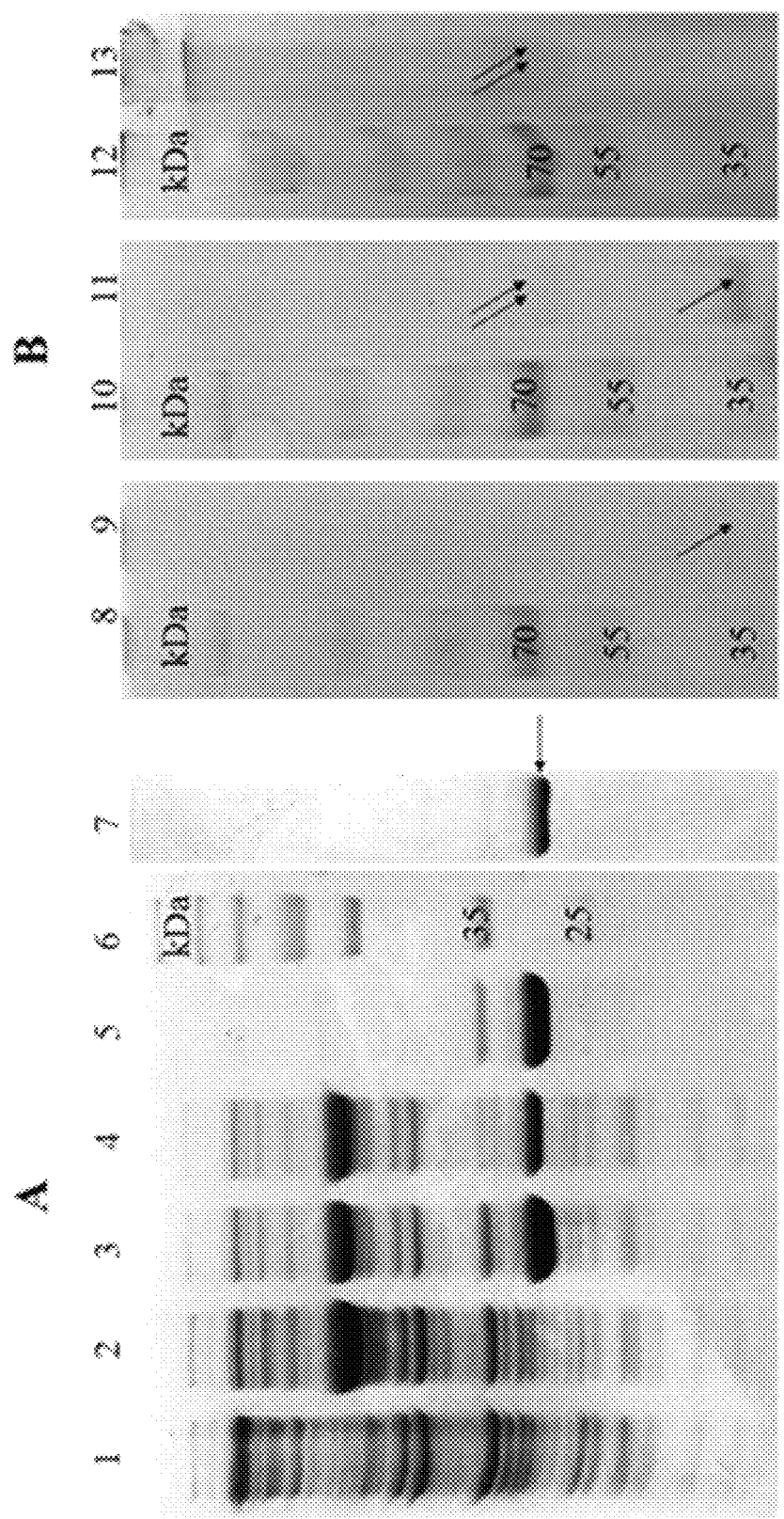
[FIG. 11]

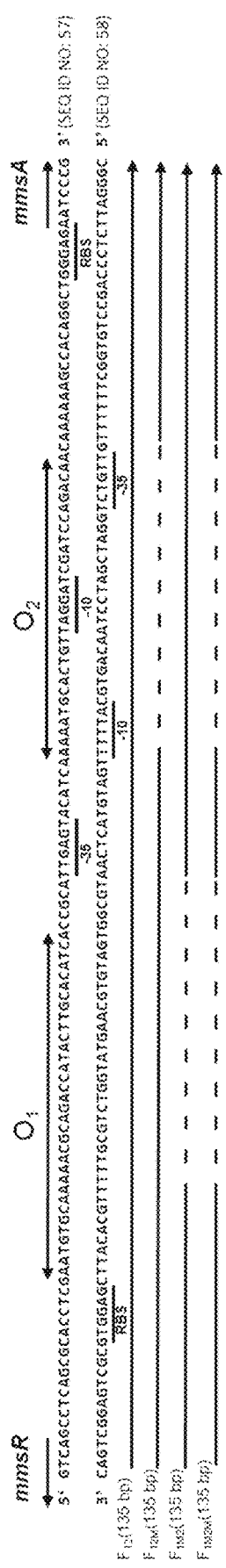
[FIG. 12a]

[FIG. 12b]
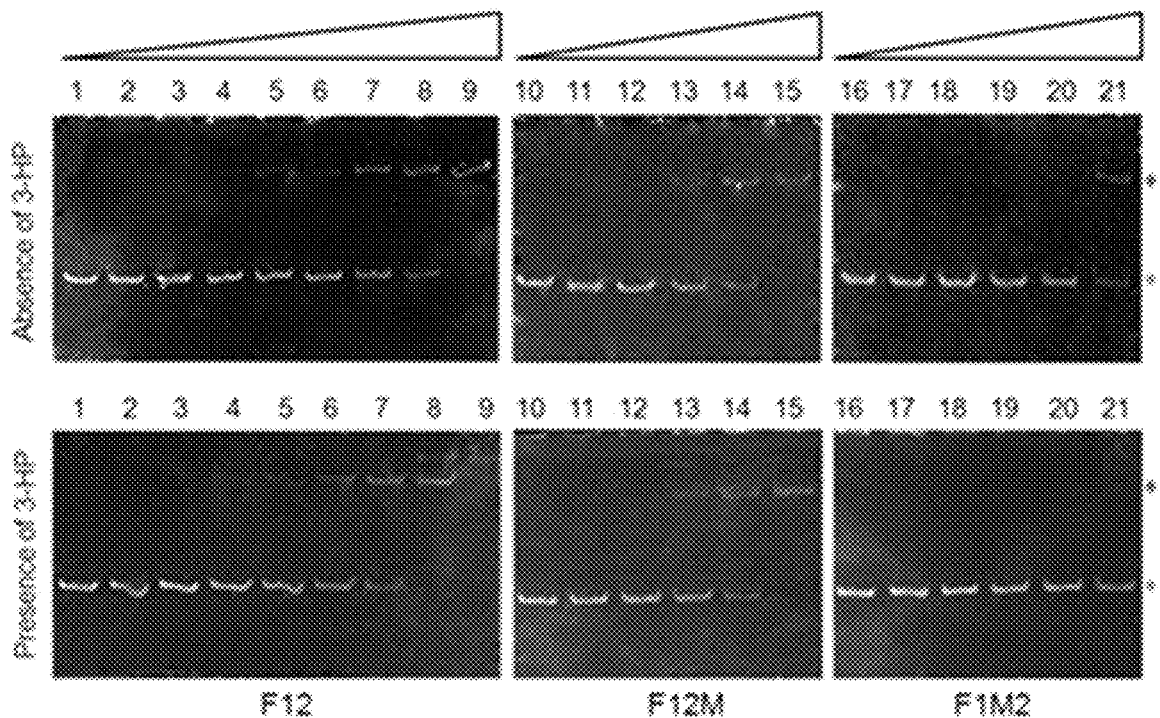
[FIG. 12c]

[FIG. 13a]

Group 1: *Pseudomonas*

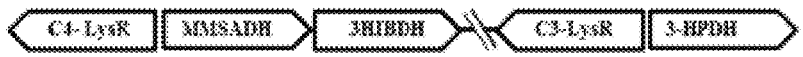

Group 2: *Acinetobacter, Cupriavidus*

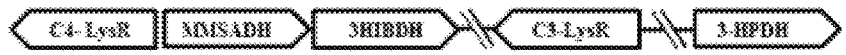

Group 3: *Collimonas*

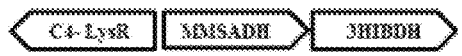

Group 4: *Alcanivorax, Burkholderia*

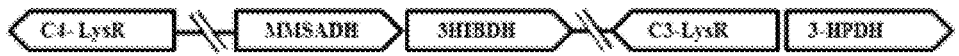

Group 5: *Corynebacterium, Segniliparus*

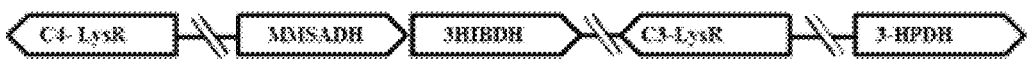

Group 6: *Methylocystis, Tatlockia, Curvibacter*

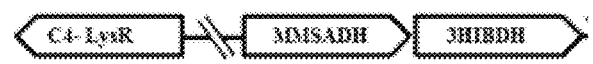

Group 7: *Sphingobium, Polynucleobacter, Bradyrhizobium, Xanthobacter, Catenulispora, Agrobacterium, Methylobacterium, Novosphingobium, Sphingomonas, Thalassospira*

Group 8: *Alicyclophilus, Alteromonas, Kitasatospora, Paracoccus, Simiduia, Sphingopyxis*

Group 9: *Sinorhizobium, Beijerinckia, Aeromonas, Castellaniella, Amycolatopsis*

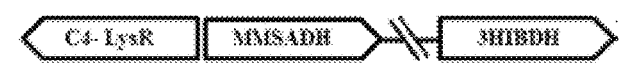

[FIG. 13b]

Group 10: *Verminephrobacter, Janthinobacterium, Idiomarina, Glaciecola, Gordonia*

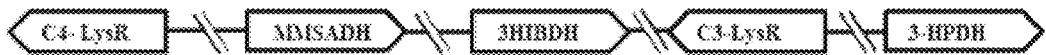

Group 11: *Achrmobacter, Acidovorax, Alcaligenes, Halomonas, Azospirillum, Chromobacterium, Comamonas*

Group 12: *Oceanimonas, Rastolnia, Pseudoalteromonas, Ferrimonas, Delftia, Pseudogulbenkiania, Anaeromyxobacter, Bordetella*

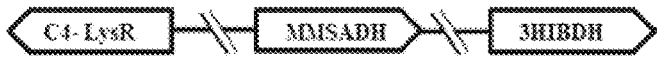

Group 13: *Phenylobacterium, Psychrobacter, Shewanella, Vibrio, Xanthomonas, Stenotrophomonas, Caulobacter, Hahella, Kutzneria, Rhodomicrobium,*

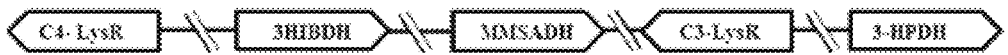

Group 14: *Pseudoxanthomonas, Azotobacter*

Group 15: *Parvibaculum, Hirschia*

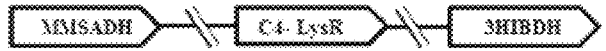

Group 16: *Photobacterium*

[FIG. 14c]

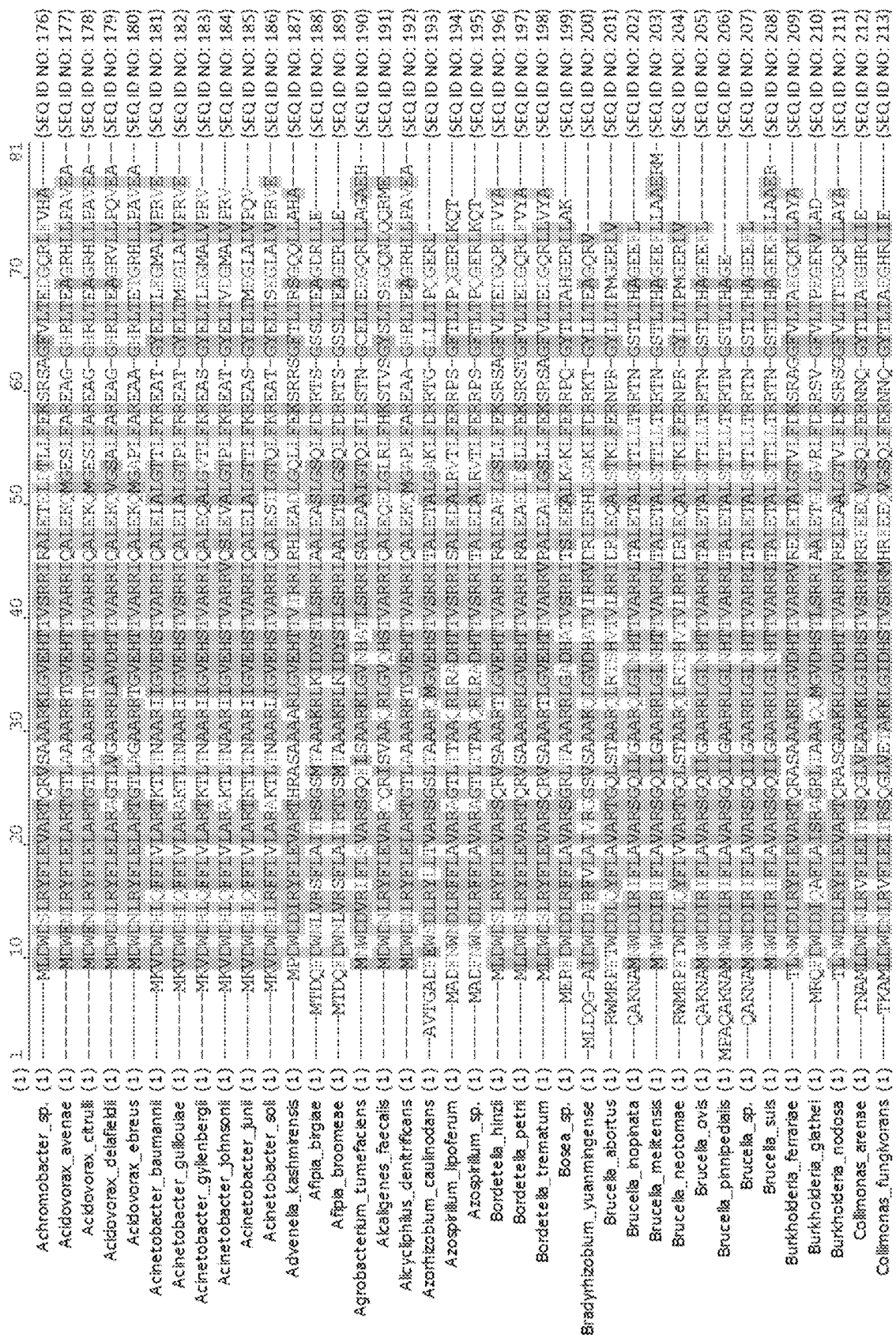
[FIG. 15a]

[FIG. 15b]

[FIG. 16]

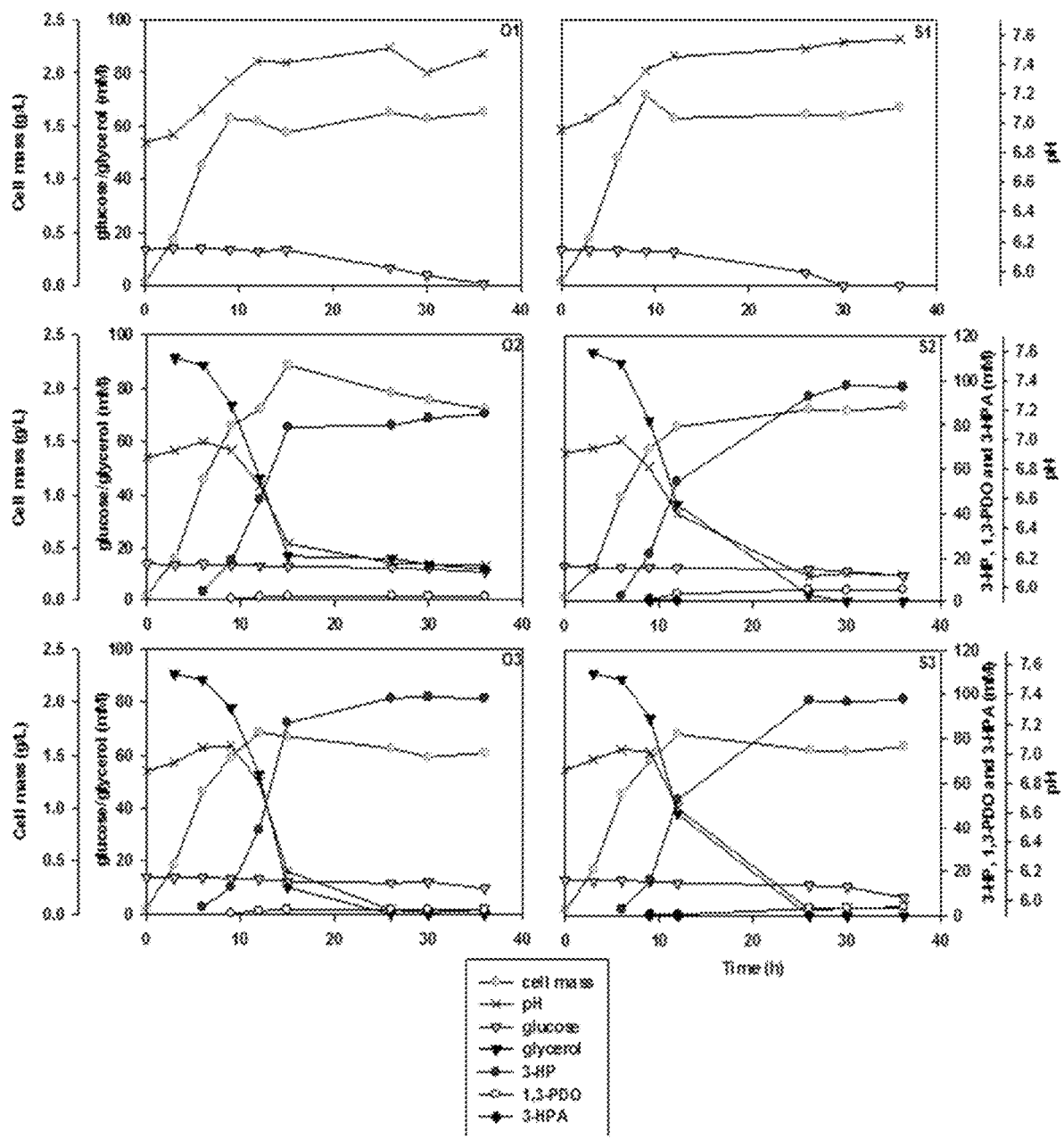
[FIG. 17]

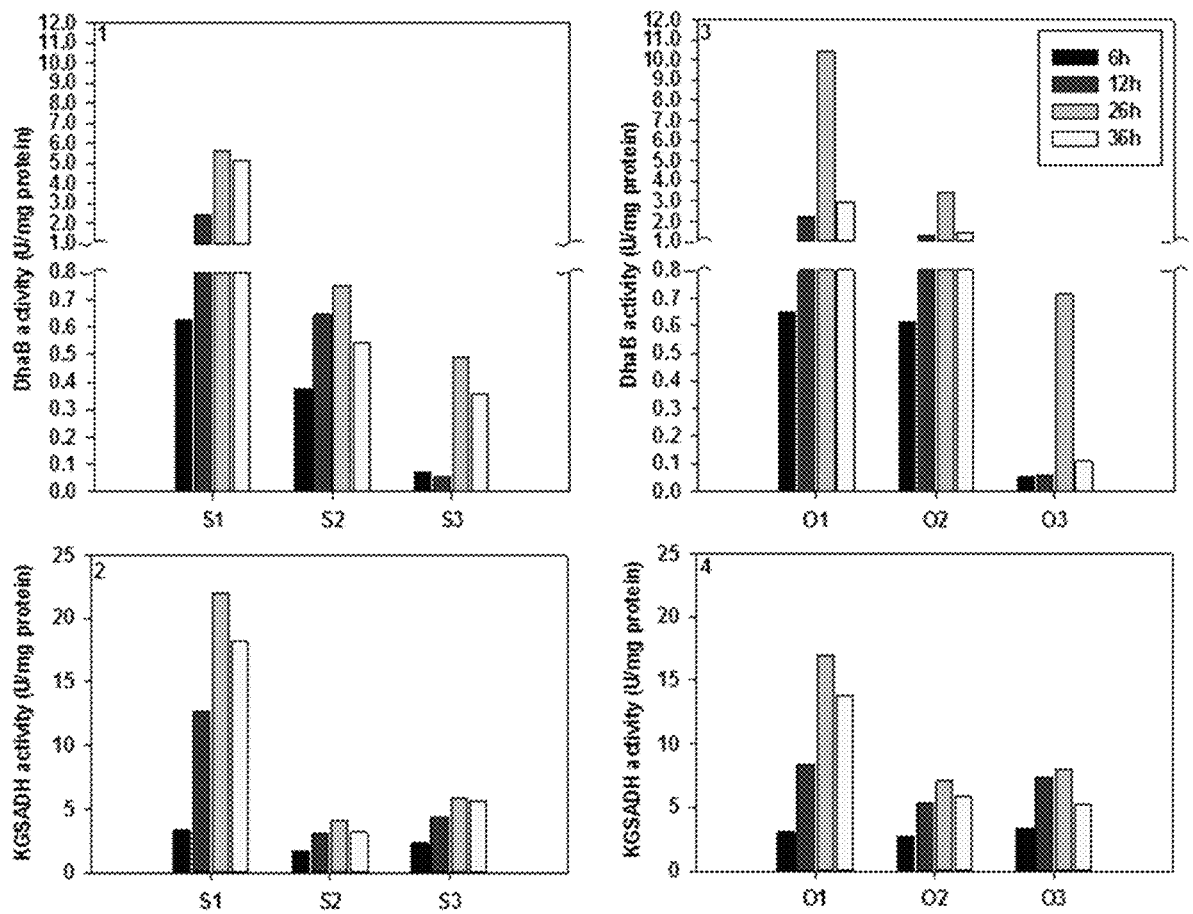
[FIG. 18]

[FIG. 19]
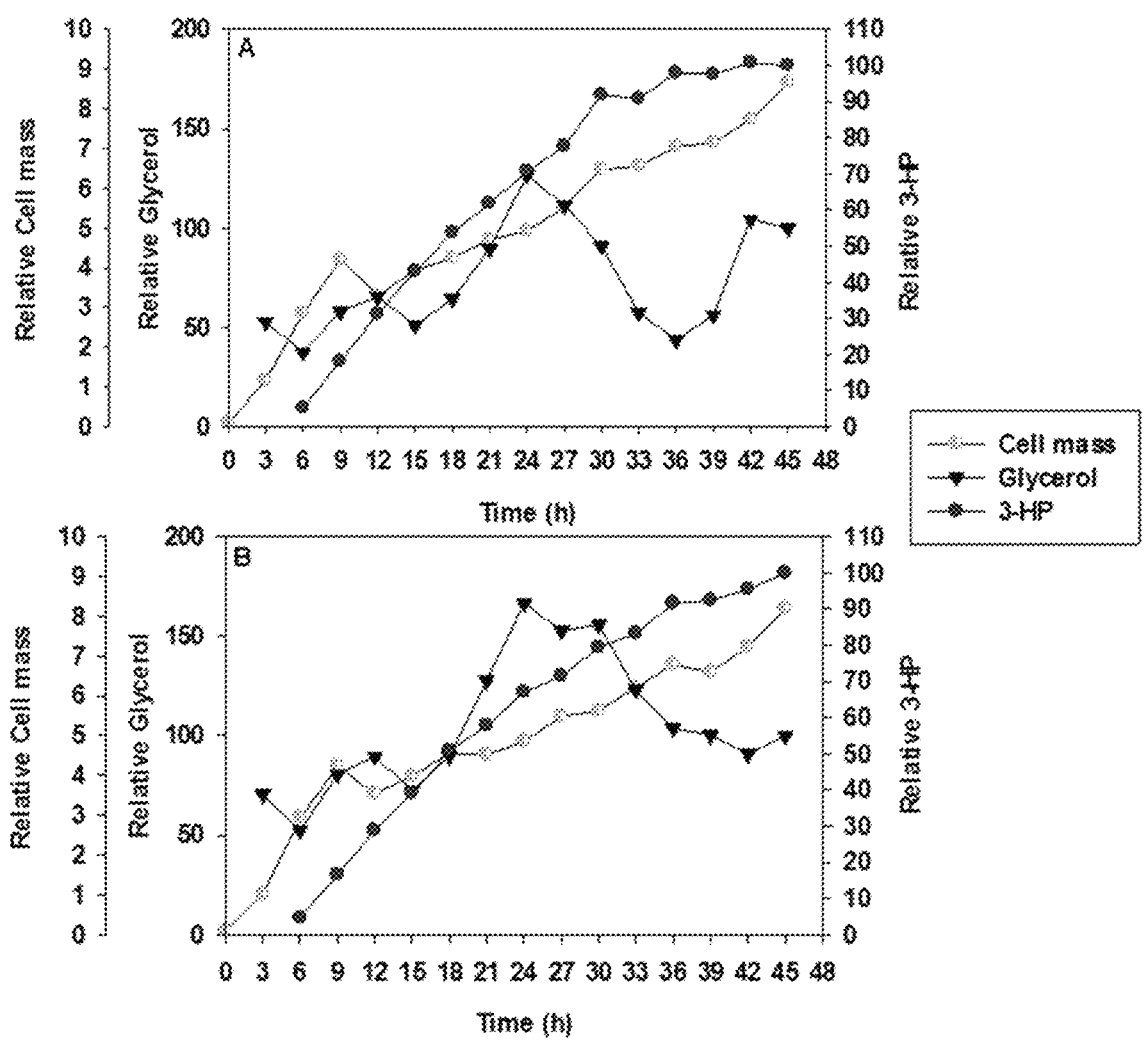

PROMOTER SYSTEM INDUCING EXPRESSION BY 3-HYDROXYPROPIONIC ACID AND METHOD FOR BIOLOGICAL PRODUCTION OF 3-HYDROXYPROPIONIC ACID USING SAME

TECHNICAL FIELD

The present invention relates to a promoter system inducing expression of 3-hydroxypropionic acid (3-HP) and a method for biological production of 3-HP.

BACKGROUND ART 3-hydroxypropionic acid (3-HP) is an important synthetic immediate used in various chemical processes, and is used as a raw material for producing acrylic acid, acrylamide, 1,3-propanediol, malonic acid, and the like. 3-HP is also used for synthesis of a biodegradable polymer. Biological production of 3-HP using glycerol has been successfully accomplished through genetic engineering of key enzymes required for 3-HP production pathways in various bacteria. In detail, production of 3-HP has been confirmed in bacteria, such as *Escherichia coli, Klebsiella pneumoniae, Pseudomonas denitrificans*, and the like, by (over)expression of glycerol dehydratase which is a coenzyme $B_{12}$-dependent enzyme, DhaB reactivase which is a glycerol dehydratase reactivase, and aldehyde dehydrogenase which is a $NAD^+$-dependent enzyme, and the like through genetic engineering. Some recombinant strains including *E. coli* W DUBGK were able to produce more than 40 g/L of 3-HP for 48 hours, but had a difficulty in increasing 3-HP production beyond that. It was particularly observed that, as fermentation time for the production of 3-HP continues, problems that enzymes, such as glycerol dehydratase and aldehyde dehydrogenase, become unstable or lose activity occur. In this regard, one important reason why the activity of glycerol dehydratase disappears is due to a mechanism called suicidal inactivation. In such a mechanism, coenzyme $B_{12}$ which is a coenzyme of glycerol dehydratase is irreversible damaged during a dehydration reaction from glycerol to 3-hydroxypropionaldehyde (3-HPA), and such a deactivation reaction is promoted in the presence of oxygen. In recent years, to ease deactivation-based on such a mechanism above, mutant glycerol dehydratase has been developed according to site-directed mutagenesis. Several mutant enzymes have been found to have improved enzyme stability, but enzyme activity thereof has been observed to be significantly reduced when compared to conventional enzymes.

Another reason for the problems above is due to toxicity of 3-HPA which is a highly reactive intermediate. When glycerol dehydratase or aldehyde dehydrogenase is present with 3-HPA, activity of glycerol dehydratase or aldehyde dehydrogenase decreases depending on a concentration of 3-HPA. Aldehydes are known to react with amino acid residues, such as ε-amino acid ($NH3^+$), a sulfhydryl group (—C—SH), and an imidazole group that are present in lysine, cysteine, and histidine, respectively. Efforts have been made to improve the stability of many enzymes in the presence of aldehydes using site-directed mutagenesis and random mutagenesis, but have been limitedly succeeded.

An interesting alternative to solving the problems that the enzymes become unstable is continuous synthesis of new enzymes having activity during the whole period of cell culture. Theoretically, if new enzymes can be supplied as much as the enzymes that become unstable, the enzyme activity of the enzymes in cells can be kept constant. In particular, it is necessary to continuously express enzymes at the time when the growth of cells in the latter half of fermentation slows down and the total metabolic activity of the cells is decreased due to high concentrations of 3-HP.

DETAILED DESCRIPTION OF THE INVENTION

Technical Problem

The present invention provides an inducible promoter for 3-hydroxypropionic acid (3-HP) or a derivative thereof, the inducible promoter including a binding site to a LysR protein that is reactive to 3-HP or a derivative thereof.

The present invention also provides a recombinant gene expression cassette reactive to 3-HP or a derivative thereof, the recombinant gene expression cassette including a lysR gene encoding a LysR protein that is reactive to 3-HP or a derivative thereof, a promoter comprising a binding site to a LysR protein, and a gene encoding a target expression protein.

Technical Solution

To achieve the technical problems above, the present invention provides an inducible promoter for 3-hydroxypropionic acid (3-HP) or a derivative thereof, the inducible promoter including a binding site to a LysR protein that is reactive to 3-HP or a derivative thereof.

In addition, the present invention relates to a recombinant expression vector including the inducible promoter for 3-HP or a derivative thereof, a recombinant microorganism transformed by the recombinant expression vector, and a method of producing 3-HP, the method including culturing the recombinant microorganism.

In addition, the present invention provides a recombinant gene expression cassette reactive to 3-HP or a derivative thereof, the recombinant gene expression cassette including a lysR gene encoding a LysR protein that is reactive to 3-HP or a derivative thereof, a promoter including a binding site to a LysR protein, and a gene encoding a target expression protein.

In addition, the present invention provides a recombinant expression vector including the recombinant gene expression cassette that is reactive to 3-HP or a derivative thereof, a recombinant microorganism transformed with the recombinant expression vector, a recombinant microorganism including the recombinant gene expression cassette, which is reactive to 3-HP or a derivative thereof, inserted in a chromosome of a host cell, and a method of producing a target expression protein, the method including culturing the recombinant microorganism.

Advantageous Effects of the Invention

The present invention relates to a promoter system inducing expression of 3-hydroxypropionic acid (3-HP) and a method of biologically producing 3-HP using the same. To improve production of 3-HP in a biological manner, continuous synthesis of new enzymes having enzyme activity is necessary. As a result of screening 3-HP reactive transcription regulators and 3-HP reactive promoters from several microorganisms including *Pseudomonas denitrificans*, it was confirmed that the transcriptions regulations and promoters are composed of LysR proteins and particular gene nucleotide sequences binding to the LysR proteins. Therefore, the 3-HP inducible system is expected to be effectively used to regulate 3-HP metabolic pathways.

DESCRIPTION OF THE DRAWINGS

FIG. 1 is shows production (A) of 3-hydroxypropionic acid (3-HP) in proliferating cells and degradation (B) of 3-HP. A strain for a 3-HP production test of *Pseudomonas denitrificans* was cultured in an M9 medium supplemented with 25±2 mmol/L of 3-HP as a single carbon energy source and an energy source. Meanwhile, resting cells for a 3-HP degradation test of *P. denitrificans* were prepared by culturing on an M9 medium supplemented with 25±2 mmol/L of 3-HP. Here, the standard deviation for 3-HP concentration measurements was calculated to be 10% or less. Symbols: closed circle, 3-HP; semi-circle left, cell mass; cross, pH.

FIG. 2 shows two metabolic pathways of 3-HP (oxidation and reduction pathways). Abbreviations: 3-HPDH, 3-hydroxypropionate dehydrogenase; 3-HIBDH, 3-hydroxyisobutyrate dehydrogenase; MMSADH, methylmalonate semialdehyde dehydrogenase; HPCS, 3-hydroxypropionyl-CoA synthetase.

FIG. 3 shows a relative mRNA expression level (A) and a fold increase in *P. denitrificans* ATCC13867 with respect to a 3-hydroxypropionate catabolite gene. FIG. 3(A) shows a result (shown in a grey bar) obtained by culturing *P. denitrificans* in an M9 medium supplemented with 25 mmol/L of 3-HP and a result (shown in a black bar) obtained by culturing *P. denitrificans* in an M9 medium not supplemented with 3-HP. FIG. 3(B) shows a result (shown in a grey bar) of a difference in mRNA expression levels depending on the 3-HP supply, wherein the result is indicated as a fold increase. Here, the standard deviation for mRNA level measurements was calculated to be 10% or less. Here, the mRNA expression levels are compared using a rpoD gene as a reference gene.

FIG. 4 shows expression of genes, i.e., mmsadh (shown in black) and 3hibdhIV (shown in grey). In addition to 3-HP, 3-hydroxyisobutyrate (3HIB), 3-hydroxybutyrate (3-HB), L-valine, or the like also acts as an inducer.

FIG. 5 shows expression of a gene, 3hpdH. In addition to 3-HP, 3HIB, 3-HB, L-valine, or the like also acts as an inducer.

FIGS. 6A and 6B show a promoter system gene sequence and a structure thereof, the promoter system being induced by 3-HP. FIG. 6A shows positions of genes, mmsadh and 3hibdh, and a gene of a LysR protein (C4-LysR) that regulates gene transcription of mmsadh and 3hibdh. FIG. 6B shows positions of a 3hpdh gene and a gene of a LysR protein (C3-LysR) that regulates gene transcription of 3hpdh.

FIG. 7 shows results of analysis for an inducible promoter for a C4-LysR gene. O1 and O2 operators between the genes, such as C4-LysR (represented by mmsR) and mmsadh (represented by mmsA), are each present at position −58 and position −9 at positions relative to, as a standard, a transcription start site of mmsadh, and each include an inverted repeat sequence. As a result of the analysis of the inverted repeat sequence constituting each of O1 and O2, a T$\underline{A}$CGTGT$\underline{A}$A sequence was conserved.

FIG. 8 shows a regulatory mechanism of a LysR family transcriptional regulator.

FIG. 9 shows an amino acid sequence that is highly conserved in a LysR protein. Positions of the amino acid was centered on the C4-LysR protein. However, the amino acid sequence conserved in a DNA binding domain or a substrate binding domain was the same for all LysR proteins derived from a strain used in the present invention.

FIG. 10 shows SDS-PAGE results for analyzing solubility of C-his tag C4-LysR by using a chaperon plasmid: pG-KJE8 (A), pGro7 (B), pKJE7 (C), pG-Tf2 (D), and pTf16 (E). A genetically engineered strain of *E. coli* BL21 was cultured in an LB medium at a temperature of 25° C., induced with 0.1 mM IPTG, and harvested within 4 or 12 hours. Here, the blue arrow shows the size of 34.4 kDa for the C4-LysR protein.

FIG. 11 shows SDS- and native-PAGE analysis results of the purified C4-LysR protein. FIG. 11(A) shows purification results by denaturing SDS-PAGE, wherein lane 1 shows a wild-type (crude) result; lane 2 shows a (−)IPTG result; lanes 3, 4, 5, and 7 each show cell-free, soluble, insoluble, and purified fraction results; and lane 6 shows a protein marker result. FIG. 11(B) shows native PAGE analysis results, wherein lanes 8, 10, and 12 show protein marker results, and lanes 9, 11, and 13 show purified C4-LysR protein results when loaded at a concentration of 65 nM, 220 nM, and 550 nM, respectively.

FIGS. 12A-12C show the effect of C4-LysR concentrations and 3-HP on binding of DNA fragments between the C4-LysR protein and a promoter region thereof. FIG. 12A shows a DNA fragment sequence of a promoter used in the experiment, wherein F12 indicates a fragment including both O1 and O2, F12M indicates a fragment including only an O1 operator, F1M2 indicates a fragment including only an O2 operator, and F1M2M indicates a fragment from which both O1 and O2 are removed, and the DNA fragments used in the experiment had the same length of 135 bp. FIG. 12B shows results of electromobility shift assay (EMSA) obtained by analyzing in vitro binding of DNA fragments between the C4-LysR protein and a promoter region thereof, wherein the upper panel shows the results of electrophoresis performed in the absence of 3-HP, and the lower panel shows the results of electrophoresis performed in the presence of 25 mM of 3-HP, and in lanes 1 to 9, the concentration of the C4-LysR protein was gradually increased from 0 nM to 0.36 nM, 0.73 nM, 1.45 nM, 2.9 nM, 5.8 nM, 11.6 nM, 14.5 nM and 24.2 nM, in lanes 10 to 15, the concentration of the C4-LysR protein was gradually increased from 0 nM to 2.9 nM, 5.8 nM, 11.6, nM 14.5 nM, and 24.2 nM, and in lanes 16 to 21, the concentration of the C4-LysR protein was gradually increased from 0 nM to 2.9 nM, 11.6 nM, 24.2 nM, and 72.7 nM. FIG. 12C shows quantitative results of binding affinity of DNA fragments between the C4-LysR protein and a promoter region thereof, wherein affinity refers to a dissociation constant ($K_D$), and that is, half of the DNA fragments was represented by the concentration of a protein required to bind the C4-LysR protein.

FIGS. 13A and 13B show the structural comparison of genetic populations involved in the 3-HP degradation pathway between *P. denitrificans* ATCC13861 and various microorganisms.

FIGS. 14A-14C and FIGS. 15A-15B show the multiple sequence arrangement of the N-terminal HTH included in a LysR region: C4-LysR (FIGS. 14A-14C) and C3-LysR (FIGS. 15A-15B).

FIG. 16 shows a pUCPK'/PC3-gdrAB-dhaB, PC4-KGSADH plasmid developed for the expression of glycerol dehydratase and KGSADH in *P. denitrificans*.

FIG. 17 shows results (O1 & S1) of comparing consumption of glucose and glycerol, cell growth, 3-HP production, and pH changes by a strain of Pd Δ3hpdhΔ3hibdhIVΔ3hibdhI (pUCPK'/PC3-dhaB-gdrAB, PC4-KGSADH) (O1, O2 & O3) and a strain of Pd Δ3hpdhΔ3hibdhIVΔ3hibdhI (pUCPK'/PC3-gdrAB-dhaB, PC4-KGSADH) (S1, S2 & S3): no glycerol; (O2 & S2), 25 mg/L of CoCl$_2$.6H$_2$O added to a culture medium; (O3 & S3), 12 μmol/L of coenzyme B12 added to a culture medium, and 100 mM of glycerol added at 3 hours.

FIG. 18 shows results of comparing time-dependent inactivation of glycerol dehydratase and KGSADH by using cell lysates of Pd Δ3hpdhΔ3hibdhIVΔ3hibdhI (pUCPK'/PC3-dhaB-gdrAB, PC4-KGSADH) and Pd Δ3hpdhΔ3hibdhIVΔ3hibdhI (pUCPK'/PC3-gdrAB-dhaB, PC4-KGSADH).

FIG. 19 shows time-dependent changes in consumption of glycerol and glucose, biomass, and 3-HP production upon a fed-batch bioreactor operation: (A) recombinant Pd Δ3hpdhΔ3hibdhIVΔ3hibdhI (pUCPK'/PC3-dhaB-gdrAB, PC4-KGSADH) and (B) Pd Δ3hpdhΔ3hibdhIVΔ3hibdhI (pUCPK'/PC3-gdrAB-dhaB, PC4-KGSADH).

BEST MODE

Accordingly, in terms of efficiently maintaining expression of a 3-hydroxypropionic acid (3-HP) production enzyme, the inventors of the present invention have discovered a specific gene transcription promoter system, which induces the expression of 3-HP, in various microorganisms, and then, examined genetic and biochemical characteristics of the promoter system. The promoter system is an unusual system that has never been reported in documents yet, and consists of a transcription activating protein of 3-HP and a DNA sequence specifically binding to the transcription activating protein. The inventors of the present invention developed a recombinant strain capable of producing 3-HP at a high concentration from glycerol by overexpressing DhaB, GdrAB, and KGSADH by using the promoter system, thereby completing the present invention.

The present invention provides an inducible promoter for 3-HP or a derivative thereof, the inducible promoter including a binding site to a LysR protein which is reactive to 3-HP or a derivative thereof.

In addition, the present invention provides a recombinant expression vector including the inducible promoter for 3-HP or a derivative thereof. Preferably, the recombinant expression vector may further include a gene encoding a foreign protein linked to the inducible promoter for 3-HP or a derivative thereof. More preferably, the foreign protein may be glycerol dehydratase (DhaB), DhaB reactivase (GdrAB), or α-ketoglutaric semialdehyde dehydrogenase (KGSADH), but embodiments of the present disclosure are not limited thereto.

In addition, the present invention provides a recombinant microorganism transformed with the recombinant expression vector. Preferably, the recombinant microorganism may have producibility of 3-HP. More preferably, the recombinant microorganism may be *Pseudomonas denitrificans*, and more preferably, may be a stain of *Pseudomonas denitrificans* Δ3hpdhΔ3hibdhIVΔ3hibdhI from which 3hpdh, 3hibdh, and mmsadh genes relating to degradation of 3-HP are deleted in a strain of *P. denitrificans*, but embodiments of the present disclosure are not limited thereto.

In addition, the present invention provides a method of producing 3-HP, the method including culturing the recombinant microorganism.

In addition, the present invention provides a recombinant gene expression cassette reactive to 3-HP or a derivative thereof, the recombinant gene expression cassette including a lysR gene encoding a LysR protein that is reactive to 3-HP or a derivative thereof, a promoter comprising a binding site to a LysR protein, and a gene encoding a target expression protein.

In addition, the present invention provides a recombinant expression vector including the recombinant gene expression cassette that is reactive to 3-HP or a derivative thereof, and a recombinant microorganism transformed with the recombinant expression vector.

In addition, the present invention provides a recombinant microorganism including the recombinant gene expression cassette that is reactive to 3-HP or a derivative thereof inserted in a chromosome of a host cell. It will be obvious to one of ordinary skill in the art that, even if the recombinant gene expression cassette is inserted into the genome of the host cell, the same effect as the case where the recombinant vector is introduced into a host cell is made.

In the present invention, as a method of inserting the recombinant gene expression cassette to a chromosome of a host cell, any gene engineering method known in the art may be used. In one embodiment, a method using a retrovirus vector, an adenovirus vector, an adeno-associated virus vector, a herpes simplex virus vector, a poxvirus vector, a lentivirus vector, or a non-viral vector may be used.

In addition, the present invention provides a method of producing a target expression protein, the method including culturing the recombinant microorganism.

Preferably, the culturing of the recombinant microorganism may further include adding for 3-HP.

Preferably, the LysR protein or the promoter may be derived from a microorganism with 3-HP degradability. More preferably, the LysR protein or the promoter may be *Achromobacter denitrificans*, *Acidovorax avenae* subsp., *Acidovorax* sp., *Acinetobacter baumannii*, *Aeromonas hydrophilia*, *Agrobacterium* sp., *Alcaligenes faecalis*, *Alcanivorax hongdengensis*, *Alicycliphilus denitrificans*, *Alteromonas marina*, *Amycolatopsis* sp., *Anaeromyxobacter dehalogenans*, *Azospirillum brasilense*, *Azotobacter vinelandii*, *Beijerinckia indica*, *Bordetella avium*, *Bradyrhizobium japonicum*, *Burkholderia ambifaria*, *Catenulispora acidiphilia*, *Caulobacter* sp., *Castellaniella defragrans*, *Chromobacterium violaceum*, *Collimonas arenae*, *Comamonas testosteroni*, *Corynebacterium vitaeruminis*, *Cupriavidus necator*, *Curvibacter gracilus*, *Delftia acidovorans*, *Ferrimonas balearica*, *Glaciecola nitratireducens*, *Gordonia bronchialis*, *Hahella chijuensis*, *Halomonas elongata*, *Hirschia litorea*, *Idiomarina* sp., *Janthinobacterium lividum*, *Kitasatospora setae*, *Kutzneria albida*, *Methylobacterium* sp., *Methylocystis* sp., *Novosphingobium* sp., *Oceanimonas smirnovii*, *Paracoccus* sp., *Parvibaculum lavamentivorans*, *Phenylobacterium kunshanensis*, *Photobacterium gaetbuleda*, *Polynucleobacter necessarius asymbioticus*, *Pseudoalteromonas carrageenovora*, *Pseudogulbenkiania* sp., *Pseudomonas denitrificans* ATCC13867, *P. knackmussii*, *P. protegens*, *P. fluorescens*, *Pseudoxanthomonas spadix*, *Psychrobacter phenylpyruvicus*, *Ralstonia oxalatica*, *Rhodomicrobium vannielli*, *Segniliparus rotundus*, *Shewanella oneidensis*, *Simiduia agarovorans*, *Sinorhizobium meliloti*, *Sphingobium chlorophenolicum*, *Sphingomonas wittichii*, *Sphingopyxis alaskensis*, *Stenotrophomonas maltophilia*, *Streptomyces nodosus*, *Tatlockia micdadei*, *Thalassospira xiamenensis*, *Variovorax paradoxus*, *Verminephrobacter eiseniae*, *Vibrio furnissii*, *Xanthobacter autotrophicus*, *Xanthomonas campestri*, and *Xanthomonas oryzae*, but embodiments of the present disclosure.

Preferably, the LysR protein may have an N-terminal domain having a helix-turn-helix structure and binding to DNA, a C-terminal domain binding to 3-HP or a derivative thereof, and a C-terminal domain contributing to stabilization of a LysR protein dimer, but embodiments of the disclosure are not limited thereto.

More preferably, the N-terminal domain having a helix-turn-helix structure and binding to DNA may include an amino acid sequence represented by SEQ ID NO: 1 or 2, the C-terminal domain binding to 3-HP or a derivative thereof may include an amino acid sequence represented by SEQ ID NO: 3, and the C-terminal domain contributing to stabilization of a LysR protein dimer may include an amino acid sequence represented by SEQ ID NO: 4, but embodiments of the present disclosure are not limited thereto.

"X" or "Xaa" described in SEQ ID NOs: 1 to 4 does not refer to particular amino acid, meaning that any amino acid may be used. More preferably, the LysR protein may be a LysR protein having Genebank ID represented by Table 4 and 5, but embodiments of the disclosure are not limited thereto.

Preferably, the binding site to the LysR may include two LysR protein dimers that are bonded to each other, and may include a base sequence selected from SEQ ID NOs: 5 to 43, wherein an inverted repeat sequence and another inverted repeat sequence paired with therewith may be repeated twice in the binding site to a LysR protein, wherein the inverted repeat sequence may consist of a base sequence represented by one selected from SEQ ID NOs: 5 to 43, but embodiments of the disclosure are not limited thereto.

More preferably, the binding site to a LysR protein may consist of a base sequence represented by SEQ ID NO: 44 or 45.

"n" described in the SEQ ID NOs: 5 to 43 does not refer to a particular base, meaning the any base may be used.

The SEQ ID NO: 44 or 45 may be a promoter base sequence derived from *Pseudomonas denitrificans* ATCC13867.

Preferably, the derivative may be 3-hydroxyisobutyrate (3HIB) or 3-hydroxybutyrate (3-HB), but embodiments of the disclosure are not limited thereto.

The term "vector" as used herein refers to a self-replicating DNA molecule that is used to carry the clone gene (or other fragments of the clone DNA).

The term "expression vector" as used herein refers to a recombinant DNA molecule including a desired coding sequence and a suitable nucleic acid sequence necessary for expressing a coding sequence operably linked to a particular host organism. The expression vector may include at least one selective marker. The marker may be a nucleic acid sequence having characteristics that can be generally selected by a chemical method, and may include all genes capable of distinguishing a transformed cell from a non-transformed cell. Examples of the marker include antibiotic resistance genes, such as ampicilin, kanamycin, G418, Bleomycin, hygromycin, and chloramphenicol, but embodiments of the present disclosure are not limited thereto. Such a marker can be appropriately selected from one of ordinary skill in the art.

Hereinafter, the present inventive concept will be described below in further detail through Examples and Comparative Examples. However, such Examples are for illustrative purposes only and do not limit the scope of the present inventive concept.

<Example 1> Identification of Gene Expression System by 3-HP

1. Materials

A number of strains including *Achromobacter denitrificans* and *Acinetobacter baumannii* were obtained from the Korean Culture Center of Microorganisms (KCCM). A number of strains including *Acidovorax avenae* subsp. and *Agrobacterium* sp. were purchased from the Korean Collection for Type Cultures (KCTC). A number of strains including *Alicycliphilus denitrificans* and *Anaeromyxobacter dehalogenans* were obtained from DSM in Germany. A number of strains including *Aeromonas hydrophilia* and *Pseudomonas denitrificans* ATCC13867 purchased from ATCC in the United States. A primer was synthesized by COSMO GENETECH (Seoul, Korea). 3-HP was purchased from Tokyo Kasei Kogyo (TCI America, Portland, Oreg.) in Japan. An enzyme extract (Cat. 212750) and tripton (Cat. 211705) were purchased from Difco (Becton Dickinson; Franklin Lakes, N.J.). All chemicals and enzymes not mentioned were purchased from Sigma Aldrich (St. Louis, Mo.).

2. 3-HP Production of Proliferating Cells and 3-HP Degradation in Dormant Cells

Shake flask experiments were carried out in a 250 mL non-baffled Erlenmeyer flask in a volume of 30 mL in shaking incubator at a temperature of 37° C. and a stirring speed of 200 rpm. Experiments on 3-HP production by *P. denitrificans* were performed under conditions where an M9 medium having a modified volume of 30 mL was added to a 250 mL non-baffled Erlenmeyer flask for culturing in a shaking incubator at a temperature of 37° C. at a stirring speed of 200 rpm. Here, compositions of the modified M9 medium for culturing a strain included 100 mM phosphate buffer (pH 7.0), 0.25 g/L of $MgSO_4 \cdot 7H_2O$, 1.0 g/L of NaCl, 1.0 g/L of $NH_4Cl$, and 3-HP 25 mM.

Experiments on the dormant cells were carried out to investigate 3-HP degradation in a total of 69 microorganisms including *P. denitrificans*, and bacteria used in the experiments are shown in Table 1. To prepare active cells, 3-HP was added to a nutrient-enriched medium specified for each strain, and then, cultured in a for 250 mL non-baffled erlenmeyer flask at a volume of 50 mL. Strain culture was performed at a temperature of 37° C., and when $OD_{600}$ of cells reached about 1 to 1.5, cells were harvested by centrifugation at a speed of 5,000 rpm for 10 minutes. The precipitated cells were washed with 100 mM phosphate buffer (pH 7.0), and resuspended with 25±2 mmol/L of 3-HP in the same buffer. The above-mentioned cell harvesting, washing and resuspending procedures were performed prior to the 3-HP degradation experiments. Samples were taken periodically to investigate the concentration of 3-HP.

TABLE 1

| | | Strains used in the present invention | | | |
|---|---|---|---|---|---|
| Genus No. | Strain | Medium | Culture temperature | Aerobic condition | Purchase site |
| 1 | *Achromobacter denitrificans* | Nutrient medium | 26° C. | Aerobic | KCCM |
| 2 | *Acidovorax avenae*subsp. | Nutrient medium | 25° C. | Aerobic | KCTC |
| | *Acidovorax sp* | Tryptone soya broth | 28° C. | Aerobic | DSM |

TABLE 1-continued

Strains used in the present invention

| Genus No. | Strain | Medium | Culture temperature | Aerobic condition | Purchase site |
|---|---|---|---|---|---|
| 3 | *Acinetobacter baumannii* | Nutrient medium | 30° C. | Aerobic | KCCM |
| 4 | *Aeromonas hydrophilia* | Nutrient medium | 30° C. | Aerobic | ATCC |
| 5 | *Agrobacterium* sp. | Nutrient medium | 30° C. | Aerobic | KCTC |
| 6 | *Alcaligenes faecalis* | Nutrient medium | 30° C. | Aerobic | KCCM |
| 7 | *Alcanivorax hongdengensis* | Nutrient medium | 26° C. | Aerobic | KCTC |
| 8 | *Alicycliphilus denitrificans* | Nutrient medium | 26° C. | Aerobic | DSM |
| 9 | *Alteromonas marina* | Marine broth 2216 (DIFCO 0791) | 30° C. | Aerobic | KCCM |
| 10 | *Amycolatopsis* sp. | Nutrient medium | 30° C. | Aerobic | KCTC |
| 11 | *Anaeromyxobacter dehalogenans* | R2A medium | 28° C. | Micro-aerobic | DSM |
| 12 | *Azospirillum brasilense* | *Azospirillum* medium | 30° C. | Aerobic | KCCM |
| 13 | *Azotobacter vinelandii* | *Azotobacter* medium | 30° C. | Aerobic | KCCM |
| 14 | *Beijerinckia indica* | *Beijerinckia* medium | 30° C. | Aerobic | KCTC |
| 15 | *Bordetella avium* | Trypticase soy broth | 37° C. | Aerobic | KCCM |
| 16 | *Bradyrhizobium japonicum* | *Rhizobium* medium | 26° C. | Aerobic | KCCM |
| 17 | *Burkholderia ambifaria* | Trypticase soy broth | 28° C. | Aerobic | KCCM |
| 18 | *Catenulispora acidiphilia* | Nutrient medium | 30° C. | Aerobic | KCTC |
| 19 | *Caulobacter* sp. | Nutrient medium | 30° C. | Aerobic | KCTC |
| 20 | *Castellaniella defragrans* | Nutrient medium | 30° C. | Aerobic | KCTC |
| 21 | *Chromobacterium violaceum* | Nutrient medium | 26° C. | Aerobic | ATCC |
| 22 | *Collimonas arenae* | Nutrient medium with 5 g/L NaCl | 28° C. | Aerobic | DSM |
| 23 | *Comamonas testosteroni* | Nutrient medium | 30° C. | Aerobic | KCCM |
| 24 | *Corynebacterium vitaeruminis* | *Corynebacterium* broth | 30° C. | Aerobic | KCCM |
| 25 | *Cupriavidus necator* | Nutrient medium | 26° C. | Aerobic | KCCM |
| 26 | *Curvibacter gracilus* | Peptone, yeast extract with magnesium sulfate | 30° C. | Aerobic | ATCC |
| 27 | *Delftia acidovorans* | Nutrient medium | 30° C. | Aerobic | KCTC |
| 28 | *Ferrimonas balearica* | Triple-sugar-iron medium (Difco) | 28° C. | Aerobic | KCTC |
| 29 | *Glaciecola nitratireducens* | Broth Medium Marine Broth 2216 (BD 279110) | 25° C. | Aerobic | KCTC |
| 30 | *Gordonia bronchialis* | Trypticase soy broth | 28° C. | Aerobic | KCCM |
| 31 | *Hahella chijuensis* | Nutrient medium | 30° C. | Aerobic | KCTC |
| 32 | *Halomonas elongata* | *Halomonas* medium | 30° C. | Aerobic | KCCM |
| 33 | *Hirschia litorea* | Nutrient medium | 30° C. | Aerobic | KCTC |
| 34 | *Idiomarina* sp. | Bactomarine broth (Difco 2216) | 30° C. | Aerobic | KCTC |
| 35 | *Janthinobacterium lividum* | Nutrient medium | 25° C. | Aerobic | KCTC |
| 36 | *Kitasatospora setae* | Nutrient medium | 30° C. | Aerobic | KCTC |
| 37 | *Kutzneria albida* | Nutrient medium | 30° C. | Aerobic | KCTC |
| 38 | *Methylobacterium* sp. | Nutrient medium | 30° C. | Aerobic | KCTC |
| 39 | *Methylocystis* sp. | NMS medium for Methanotrophs with 20% methane(v/v) in the air head space | 28° C. | Aerobic | ATCC |
| 40 | *Novosphingobium* sp. | Nutrient medium | 30° C. | Aerobic | KCTC |
| 41 | *Oceanimonas smirnovii* | Marine Broth 2216 (BD 279110) | 23° C. | Aerobic | ATCC |
| 42 | *Paracoccus* sp. | Nutrient medium | 30° C. | Aerobic | KCTC |
| 43 | *Parvibaculum lavamentivorans* | Peptone 10.0 g/L; NaCl 5.0 g/L; $CaCl_2H_2O$ 0.1 g/L; Tween 80 10.0 g/L | 30° C. | Aerobic | KCTC |
| 44 | *Phenylobacterium kunshanensis* | R2A medium | 30° C. | Aerobic | KCTC |
| 45 | *Photobacterium gaetbuleda* | Nutrient medium | 30° C. | Aerobic | KCTC |

TABLE 1-continued

Strains used in the present invention

| Genus No. | Strain | Medium | Culture temperature | Aerobic condition | Purchase site |
|---|---|---|---|---|---|
| 46 | Polynucleobacter necessarius asymbioticus | R2A medium | 28° C. | Aerobic | DSM |
| 47 | Pseudoalteromonas carrageenovora | Sea water yeast peptone broth | 20° C. | Aerobic | KCCM |
| 48 | Pseudogulbenkiania sp. | Nutrient medium | 37° C. | Aerobic | DSM |
| 49 | Pseudomonas denitrificans ATCC13867 | Minimal medium | 37° C. | Aerobic | ATCC |
|  | Pseudomonas knackmussii | Nutrient medium | 30° C. | Aerobic | DSM |
|  | Pseudomonas protegens | Nutrient medium | 28° C. | Aerobic | DSM |
|  | Pseudomonas fluorescens | 1213 King medium B | 28° C. | Aerobic | ATCC |
| 50 | Pseudoxanthomonas spadix | R2A medium | 35° C. | Micro-aerobic | KCTC |
| 51 | Psychrobacter phenylpyruvicus | Trypticase soy broth | 30° C. | Aerobic | ATCC |
| 52 | Ralstonia oxalatica | Nutrient medium | 30° C. | Aerobic | KCCM |
| 53 | Rhodomicrobium vannielli | Nutrient medium | 30° C. | Aerobic | KCTC |
| 54 | Segniliparus rotundus | Bacto Middle brook7H10 medium (Difco 262710) | 28° C. | Aerobic | DSM |
| 55 | Shewanella oneidensis | Trypticase soy broth | 30° C. | Aerobic | ATCC |
| 56 | Simiduia agarovorans | Nutrient medium | 30° C. | Aerobic | KCTC |
| 57 | Sinorhizobium meliloti | Rhizobium medium | 26° C. | Aerobic | KCCM |
| 58 | Sphingobium chlorophenolicum | Nutrient medium | 30° C. | Aerobic | KCTC |
| 59 | Sphingomonas wittichii | Nutrient medium | 30° C. | Aerobic | KCTC |
| 60 | Sphingopyxis alaskensis | Nutrient medium | 30° C. | Aerobic | KCTC |
| 61 | Stenotrophomonas maltophilia | Nutrient medium | 30° C. | Aerobic | KCCM |
| 62 | Streptomyces nodosus | Nutrient medium | 30° C. | Aerobic | KCTC |
| 63 | Tatlockia micdadei | BCYE (Buffered Charcoal Yeast Extract) medium | 37° C. | Micro-aerophilic | DSM |
| 64 | Thalassospira xiamenensis | Nutrient medium | 30° C. | Aerobic | KCTC |
| 65 | Variovorax paradoxus | Nutrient medium | 30° C. | Aerobic | KCTC |
| 66 | Verminephrobacter eiseniae | R2A medium | 28° C. | Aerobic | DSM |
| 67 | Vibrio furnissii | Bactomarine broth (Difco 2216) | 28° C. | Aerobic | KCCM |
| 68 | Xanthobacter autotrophicus | Nutrient medium | 30° C. | Aerobic | KCCM |
| 69 | Xanthomonas campestri | Nutrient medium | 26° C. | Aerobic | KCCM |
|  | Xanthomonas oryzae | IFO medium 802 | 30° C. | Aerobic | KCCM |

3. RNA Extraction and Reverse Transcription Polymerase Chain Reaction

An M9 medium was used for culture of a *P. denitrificans* strain (ATCC 13567), and a nutrient medium specified for each strain was used for culture of other microorganisms shown in Table 1. Then, when examining the effect of 3-HP, 25 mM of 3-HP was added to the media provided herein. all the strains were cultured in a shaking incubator at a temperature of 37° C. at a stirring speed of 200 rpm under an aerobic condition, and cells were harvested when the cultured cells reached an exponential growth phase. After the cells were harvested in an amount of about $5\times10^8$, centrifugation was performed thereon at 5,000 g for 10 minutes. Then, 500 µl of RNA later solution (Ambion, UK) was immediately added to the precipitated cells, and then, the mixed solution was resuspended. RNA was extracted by using a total RNA isolation kit (Macherey-Nagel, Germany). 1 µg of total RNA was used for synthesis of 20 µl first-strand cDNA, and a SuperScript III first-strand synthesis system provided by Invitrogen was used for synthesis of cDNA.

A reverse transcription polymerase chain reaction was performed by using a SYBR green step with a One Real Time PCR system (Applied Biosystems, USA). In a reaction solution (20 µL) for the reverse transcription polymerase chain reaction, 300 ng of cDNA, 10 µL 2×Power SYBR Green PCR Master Mix (Applied Biosystems, UK), 5 µmol of forward and reverse primers, and DEPC treated water were contained. Conditions for the reverse transcription polymerase chain reaction were determined as follows: denaturation, 1 cycle of 95° C. for 30 seconds; amplification, 40 cycles of 95° C. for 15 seconds, 62° C. for 30 sections, and 72° C. for 30 seconds. Prior to performing the reverse transcription polymerase chain reaction, PCR was performed to confirm the effect of the primers used in the experiments for measurement of mRNA levels, and relative quantification for mRNA levels was calculated according to the ΔΔCT method.

4. Gene Cloning of LysR Protein, Protein Production, and Separation-Purification In the case of P. denitrificans, two operons, i.e., 3HPDH (hereinafter, referred to as C3 system) and 3HIBDH-IV (hereinafter, referred to as C4 system), that are involved in the 3-HP degradation were present, as well as LysR proteins, such as C3-LysR and C4-LysR, that regulate transcription of the operons. Among the proteins, protein production was attempted for C4-LysR. E. coli BL21 (DE3) was used as a host and E. coli strain Top10 was used for cloning and maintaining of plasmids. C4 LysR genes were amplified in the P. denitrificans genome by PCR, cloned into a pET30b (+) plasmid, and E. coli strain Top10 was added thereto to confirm sequences, and then, E. coli BL21 (DE3) was added thereto. For protein purification, a His tag was labeled at a C-terminus site. To express the LysR protein in an active soluble form, the LysR protein was co-expressed along with several chaperone plasmids, such as pG-KJE8, pGRO7, pG-TF2, and pTF-16. For use as a medium, an LB medium appropriately supplemented with kanamycin, chloramphenicol, L-arabinose, or the like was used and cultured under aerobic conditions. When the cell concentration reached OD of 0.6, 0.1 mM of IPTG was added to induce production of the LysR protein. For water-soluble expression of the LysR protein, various culture conditions were examined, and eventually, the LysR protein was cultured at a temperature of 25° C. at a speed of 150 rpm for 10 hours. The cultured cells were obtained by centrifugation, washed with 100 mM (pH 7) phosphate buffer, resuspended in binding buffer, and then, disrupted by French Press. Afterwards, the resulting cells were subjected to centrifugation again, and solid and undisrupted cells were removed while the solution was purified by using a Ni-affinity column. followed by being stored in a 20% glycerol solution at a temperature of 80° C.

5. Measurement of Electrophoretic Mobility Shift Assay (EMSA) for Analyzing Protein-DNA Binding Under In Vitro Conditions To study binding between the separated C4-LysR gene and a promoter region thereof under in vitro conditions, a DNA fragment of the promoter region was synthesized (see FIG. 7). Three types of fragments were synthesized: first, a fragment (designated as F12) including both O1 and O2 operators, expecting that a transcription regulatory protein binds to the entire DNA fragments between genes, C4-LysR and mmsadh; second, a fragment (designated as F12M) including a part of the O1 operator; third, a fragment (designated as F1M2) including a part of the O2 operator. The EMSA experiments were performed by using a molecular probes fluorescence-based mobility shift assay kit (fluorescence-EMSA) manufactured by Invitrogen Company. First, a DNA fragment of the promoter region was purified by a glass fiber column, mixed with a LysR protein purified with binding buffer, and a reaction was allowed at room temperature for 30 minutes. Afterwards, the mixture was loaded onto a 6% non-denaturing polyacrylamide gel, and developed in TBE buffer (pH 8) at 220 V for 30 minutes. Then, to confirm DNA bands after fixing the gel, SYBR Green EMSA staining was performed thereon, followed by quantification of band intensity by a gel documentation system (Bio-Rad). For observation of the proteins, the DNA-protein band was stained with SYPRO Ruby EMSA.

6. Analysis Method

The cell concentration was measured by using a double beam spectrophotometer (Lambda 20, Perkin-Elmer, Norwalk, Conn.) with a cuvette having a length of 10 mm. The 3-HP concentration was measured by using a high performance liquid chromatography (HPLC) (Raj et al, 2008). For preparation of a sample, a sample taken for HPLC analysis was centrifuged at 10,000×g for 10 minutes to remove cell precipitates, and a tuffryn membrane filter (Acrodisc; Pall Life Sciences, Port Washington, N.Y.). A column used for HPLC analysis had a size of 300 mm×7.8 mm Aminex HPX-87H (Bio-Rad, USA) and 2.5 mmol/L of $H_2SO_4$ was used as a mobile phase at a temperature of 65° C.

7. Results (1) Screening of 3-HP Inducible Promoter in P. denitrificans

3-HP is a carbon compound rarely present in natural environments, and there are few reports on its use as a carbon substrate or its biological degradation. However, recently, the inventors of the present invention found that P. denitrificans degraded 3-HP rapidly in both a growth phase and a non-growth phase. During the growth phase of the cells, P. denitrificans was able to be use 3-HP as a sole carbon source and an energy source (FIG. 1A). During non-growth phase of the cells, P. denitrificans showed characteristics of degrading 3-HP in the presence of oxygen (FIG. 1B). Biological degradation of 3-HP is known to use a reducing or oxidative pathway (FIG. 2). Through genome analysis and metabolite analysis using gas chromatography-mass spectrometry, it was estimated that the 3-HP degradation in P. denitrificans utilized an oxidation pathway. According to this pathway, two enzymes, presumably 3-hydroxypropionated dehydrogenase (3HPDH) and (methyl) malonate-semialdehyde dehydrogenase (MMSADH), sequentially converted 3-HP to methylmalonate semialdehyde and methylmalonate semialdehyde to acetyl-CoA (FIG. 2). In addition to 3HPDH, many 3-hydroxybutylate dehydrogenases assumed to be capable of degrading 3-HP and 3-hydroxy acid similar to 3-HP were confirmed in P. denitrificans. In this regard, the expression of various enzymes having activity against 3-HP may be possible induced by 3-HP. The mRNA levels of three genes (3hpdh, 3hibdhIV, and mmsadh) assumed to be 3-HP catabolic genes were compared by RT-PCR (FIG. 3). Here, rpoD, which is known to encode sigma factor 70 and is known as a housekeeping gene, was used as a reference gene. As a result, it was interesting to observe that the expression of genes, assumed to be related to the 3-HP degradation, was significantly increased by 3-HP. When the cells were exposed to 3-HP, 3hpdh showed a 46-fold increase, 3hibdhIV showed a 146-fold increase, and mmsadh showed a 137-fold increase. As such, up-regulation of the genes can be explained by the nature of the promoters of genes induced by 3-HP.

The expression of the genes, i.e., 3hpdh, 3hibdhIV, and mmsadh, was similar with 3-HP in size, but the possibility of being amplified by other compounds having different structures from the genes above was also examined (FIGS. 4 and 5). The genes were all amplified by 3-HP, 3-hydroxyisobutyrate (3HIB), and 3-hydroxybutyrate (3-HB). However, the amplification of the genes was not induced by lactic acid, acetic acid, propionic acid, 1,3-propanediol, and 2,3-butandiol. In particular, the amplification of the genes was induced by L-valine, and it is assumed that the induction is due to conversion from L-valine to 3-HIB in a process of metabolism. In this regard, it is determined that the transcriptional regulatory proteins were specifically reactive to 3-HP, 3-HIB, 3-HB, or the like.

(2) Analysis of 3-HP Inducible Gene Expression System

LysR-type transcriptional regulators (LTTRs) are known as transcriptional activators that regulate the same catabolic pathway as the aromatic compounds. In general, genes encoding the LTTRs are located in front of a population of genes involved in degradation of aromatic compounds and regulate the compound degradation. To identify the 3-HP degradation pathway, the gene structure analysis of operons related to 3HPDH and 3HIBDH-IV of *P. denitrificans* was performed. As a result, it was confirmed that the LTTRs were located in a similar gene sequence in the front part of the 3-HP degrading genes (FIG. 6). That is, it showed possibility that the expression of the 3-HP degrading genes may be related to the LysR protein in *P. denitrificans*. In particular, the genes (i.e., mmsadh, 3hibdh4, and 3hpdh) whose transcription was regulated by a lysR gene and a gene binding to the LysR protein (hereinafter, LysR binding to a gene of 3-hydroxyisobutyrate dehydrogenase which is a C4 compound is designated as C4-LysR, and LysR binding to a gene of 3-HP dehydrogenase which is a C3 compound is designated as C3-LysR) were located in an opposite orientation, two specific binding sites, i.e., a regulatory binding site (RS) having a conservative T-N11-A motif and an activation binding site (AS) adjacent to a 35 RNA polymerase binding site, were confirmed (FIG. 6). In addition, it was confirmed that the RS and AS overlap over positions 10 and −35 of the genes encoding the LysR protein. In this regard, it is assumed that the expression of the lysR gene is suppressed by an expression product, LysR.

More detailed analysis of the C4 LysR inducible promoter present in *P. denitrificans* was performed. O1 and O2 operators between a LysR gene and a mmsadh gene were each located at positions −58 and −9 relative to a transcription start site of the mmsadh gene, and each had an inverted repeat (FIG. 7). The inverted repeat sequence or the palindromic structure was often found in an operator site of prokaryotes, and is known to be a binding site for the transcriptional regulatory proteins. A distance between O1 and O2 sites was about 50 bp, which corresponds to 5 turns of helical DNA, and thus, it is assumed that the LysR protein can bind in the same direction when binding to O1 and O2 sites. The O1 site dyad consists of 9 bases at an interval of 15 bp, but since there was only one mismatch, it was found that the O1 site dyad was highly symmetrical. Meanwhile, the inverted repeat sequence of the O2 site also consists of 9 bases at a relatively short interval of 11 bp. 6 out of 9 was mismatched, and that is, the symmetry of the O2 site was weak. As a result of examining homology of four palindromic fragments present in the O1 and O2 operators, T<u>A</u>CGTGT<u>A</u>A was found. The bases at positions 3, 4, and 5 (bold letters) were conserved in all fragments, and the bases at positions 2 and 8 (underlined) were conserved in three fragments, suggesting that these bases play an important role in binding to the C4 LysR protein.

The effect of the O1 and O2 operators on biosynthesis of the C4-LysR protein and the mmsadh expression was examined by using a green fluorescent protein (GFP) as a reporter (Table 2). In Table 2, the effect of the C4-LysR protein and the O1 and O2 operators on the expression of the C4-LysR and the mmsadh. The relative size of the GFP was shown relative to the wild type in the absence of 3-HP. the C4-LysR protein was either not present or was produced by a constitutive promoter, and a plasmid was prepared to control the expression of the GFP upon the existing promoter having the O1 and O2 operators. Then, the experiment was carried out by inserting the prepared plasmid into a host of *P. denitrificans* from which genes between the C4-LysR and the mmsadh was deleted. Accordingly, the expression of the GFP was suppressed by the C4-LysR protein itself. That is, when the C4-LysR is expressed, the GFP expression was reduced by more than 10-fold. In addition, the expression regulation was also constant regardless of the presence of 3-HP. In this regard, it was confirmed that the transcription of C4-LysR mRNA was negatively regulated by the C4-LysR protein. This experiment was repeated by using a promoter that randomized the O1 and O2 operators to eliminate the symmetrical dyad. As a result, in the case where the O1 or O2 operator site was randomized, the GFP expression was not regulated by the C4-LysR protein, referring that the C4-LysR protein in the *P. denitrificans* strain was negatively regulated by the strain itself.

Meanwhile, the effect of the O1 and O2 operators on the mmsadh gene expression was examined in a similar manner. That is, the C4-LysR protein was constitutively expressed, and a plasmid was prepared so that GFP can be located after a promoter having O1 and O2 promoters. Here, an O1 or O2 operator was mutated so that the symmetrical dyad of an O1 or O2 site was randomized. As a result, when the O1 or O2 site was mutated, the phenomenon of up-regulation of transcription by 3-HP disappeared. That is, it means that the O1 and O2 operators are all essential sites for up-regulation of the expression by 3-HP. Thus, it has been found that the promoter of the present invention is a promoter requiring the presence of the O1 and O2 operators.

TABLE 2

| Genes tested[1] | 3-HP addition[2] | wildtype | ΔC4-LysR | O1 mutation[3] | O2 mutation[3] | O1 & O2 mutation[3] |
|---|---|---|---|---|---|---|
| C4-LysR | w/o 3-HP | 1 | 10 | 10 | 1 | 10 |
| C4-LysR | w 3-HP | 1 | 10 | 10 | 1 | 10 |
| mmsadh | w/o 3-HP | 1 | 3 | 3 | 3 | 3 |
| mmsadh | w 3-HP | 55 | 3 | 3 | 3 | 3 |

[1]GFP was used as a reporter protein, and that is, a plasmid to which a GFP gene was inserted at a C4-LysR position or a mmsadh position was used.
[2]3-HP was added in a concentration of 25 mM.
[3]When O1 and O2 were randomized, C4-LysR used a promoter expressed weakly but constitutively.

Meanwhile, the LTTRs protein was known to consist of an N-terminal which is a DNA binding domain (helix-turn-helix motif), a C-terminal which is a substrate binding domain, and a linker connecting the N-terminal and the C-terminal. The LysR protein forms a homodimer to bind RS and AS, and when an effector molecule (3-HP in the case of the present invention) binds each of the LysR proteins, due to protein-protein interaction between two LTTR dimmers the LTTR forms a tetramer, which in turn causes a structural change in DAN associated with the LysR protein. A derivative specifically binding to the LTTR tetramer is known to cause a structural changes of the LysR protein, and subsequently alter the structure of the promoter region DNA, thereby ultimately helping binding of a RNA polymerase to the promoter (FIG. 8).

When examining the structure of the C4-LysR protein which has been emphasized in the present invention, it was also resulted that the C4-LysR protein consists of an N-terminal which is a DNA binding domain (helix-turn-helix motif), a C-terminal which is a substrate binding domain, and a linker connecting the N-terminal and the C-terminal (FIG. 9). It was found that four amino acids, i.e., Thr-31, Arg-34, Glu-40, and Leu-47, played a key role in the DNA binding domain, and in the substrate binding domain, amino acids that are important for binding 3-HP and amino acids that play an important role in the dimer formation have been identified. Among these amino acids, amino acids that play an important role in the binding to 3-HP were Asp-159, Thr-160, Pro-237, and Phe-239, and amino acids that play an important role in the dimer formation were Ala-60, Gly-91, Arg-94, Pro-118, and Glu-137. In particular, amino acids that play an important role in the dimer formation were all located on the protein surface, except for Pro-118.

To confirm that the LysR protein is a transcriptional regulator, genes encoding the C3 and C4 LysR proteins were removed from *P. denitrificans* chromosomes, and then, transcription induction of transcriptionally regulated genes (mmsadh, 3hibdhIV, and 3hpdh) was examined. First, when the C4 LysR gene was removed, regardless of the presence of 3-HP, the expression of the mmsadh and 3hibdhIV genes was low, and addition of 3-HP did not increase the expression. When the C3 LysR gene was removed, the expression of the 3hpdh gene was not amplified by addition of 3-HP. However, when C3 LysR or C4 LysR gene was expressed again by using a plasmid in strains from which the C3 LysR or C4 LysR gene was removed (complementation experiment), the gene expression was amplified and restored to the same level as that of the wild type strain upon 3-HP. In this regard, it was confirmed that the C3 LysR protein and the C4 LysR protein were each a transcriptional regulatory protein that regulates the expression of the mmsadh, 3hibdhIV, and 3hpdh in cells.

(3) In Vitro Examination of Binding Characteristics of C4-LysR Protein and O1 and O2 Operator Sites To examine in vitro characteristics of the C4-LysR protein, the C4-LysR protein having a histidine tag at the C-terminal was produced in *E. coli* and purified therefrom.

First, the His tag was labeled at the C-terminal and the N-terminal, and then, the above-mentioned complementation experiment was carried out. As a result, both cases showed the same performance as the wild type LysR having no His tag. Accordingly, among two recombinant LysR proteins, only the C-His tagged LysR was subjected to biochemical experiment. The recombinant LysR was mostly expressed in an insoluble form in *E. coli*. Here, detailed optimization experiment for the expression conditions (temperature, pH, medium composition, IPTG concentration, etc) was also carried out. In addition, the influence of the various chaperon proteins also carried out. As a result, a sufficient amount of water-soluble C4-LysR was able to be produced from *E. coli* at a comparatively low temperature of 25° C. under common conditions with 0.1 M IPTG, an LB medium, and GroEL-ES chaperon (FIG. 10). The purely separated proteins were identified by SDS-PAGE. Here, the size of the C4-LysR was estimated to be about 33 kDa, which was in good match with the predicted size of the gene. However, the result of native gel electrophoresis showed that a dimer was formed in a buffer solution when the protein concentration was high (FIG. 11).

The binding between the genetically recombinant C4-LysR and the promoter DNA through EMSA experiments (FIG. 12). For the EMSA experiments, three DNA fragments were synthesized. F12 (135 bp) is a DNA fragment serving as an entire promoter region between C4-Lys and mmsadh genes and including both O1 and O2 operators; F12M (135 bp) is a DNA fragment including only the O1 operator region; and F1M2 (135 bp) is a DNA fragment including only the O2 operator region. For use as a control group, one fragment was synthesized, wherein the one fragment had the same size as F12, but was designed not to have a palindrome structure by randomizing both O1 and O2 regions. The C4-LysR protein was reacted with the DNA fragments (F12, F12M, and F1M2) and electrophoresis was carried out thereon. As a result, it was observed that the mobility of the DNA fragments decreased (FIG. 12), meaning that the C4-LysR protein binds to the DNA fragments under in vitro conditions. Such a decrease in the mobility was not observed in the control fragment. That is, the binding between C4-LysR and the DNA fragment can be achieved in the presence of base sequences of the DNA fragments, and more particularly, sequences of the O1 and O2 operators. Among the three fragments, F12 showed the highest affinity to the LysR protein, followed by F12M and F1M2. The EMASA experiments were repeated in the presence of 3-HP, and the presence of 3-HP changed affinity. That is, F12 had increased affinity, F1 had barely changed affinity, and F2 had slightly decreased affinity.

When F12 had higher affinity than F12M or F1M2, it means that the binding of O1 and O2 of the LsyR is cooperative. That is, when the LysR protein binds to the O1 site having high affinity, the binding to the O2 site is promoted. The results of the EMSA experiments showed that F12 always had low mobility, compared to F12M or F1M2. In addition, at a low concentration of the LysR, the bane having only one shift was shown, meaning that there is always more LysR proteins bound to F12. That is, when the LysR binds to F12, it means that the LysR binds to both O1 and O2 sites. F12 having higher affinity than F12M or F1M2 and having lower mobility than F12M or F1M2 shows the fact that the binding of the LysR protein to the O1 and O2 sites in F12 was cooperative. From these results of the EMSA experiments, the important properties of the 3-HP inducible promoter can be summarized as follows: (i) the promoter is characterized by having two or more inverted repeat sequence pairs, each consisting of 9 bases, and providing a binding site of the LysR protein; (ii) the LysR protein is able to bind to the promoter regardless of the binding with an inducer molecule, but the improvement in transcription efficiency is only shown by the LysR protein associated with an inducer molecule, wherein the inducer molecule may be 3-HP or 3-HIB and 3-HB that are structurally similar with 3-HP; (iii) the promoter provides a site where two LysR protein dimmers are bound, wherein the binding is cooperative each other; (iv) the promoter provides a structure that can interact with the LysR protein when the RNA polymerase binds thereto; and (v) the promoter includes the O1 and O2 operators, wherein each operator consists of 9 bases and has well conserved inverted repeat sequences.

(4) Virtual Search of 3-HP Inducible Gene Expression System and Analysis of Characteristics of the Expression System To find out a new 3-HP inducible gene expression system, putative LysR regulatory genes and mmsadh, 3hipdh, 3hpdh, and the like were screened from various microorganisms, based on the gene homology of *P. denitrificans*. The BlastP similarity search results show that similar 3-HP inducible gene expression systems are present in various microorganisms, and among well-known microorganisms, the presence of a population of genes assumed to be 3HIBDH (C4 system) and 3HPDH(C3 system) was discovered (FIG. 13 and Tables 4 and 5). As a result of structure analysis and comparison of the genes, it was confirmed that each microorganism had various genetic structures.

In a total more than 150 microorganisms, the 3-HP inducible gene expression systems were discovered, and depending on the presence of the C3-LysR and the C4-LysR and the gene arrangement characteristics, the gene expression systems were divided into a total of 16 groups. Among the groups, 9 groups had both C4 the C3 systems, and 7 groups had only the C4 system. A group having only the C3 system was not discovered. In addition, the case of the C3 system, a gene encoding the LysR protein and a gene regulating the expression thereof by the LysR protein were all characterized in that the direction of transcription was opposite. In the case of the C4 system, a gene encoding the LysR protein and a gene regulating the expression thereby of the LysR were mostly characterized in that the direction of transcription was opposite. However, in the microorganisms belonging to Groups 15 and Group 16, the direction of transcription was the same.

The characteristics of the promoter sequences that are reactive to the C3 and C4 LysR proteins were analyzed. In the same manner as in *P. denitrificans*, two tandem operator sites (designated as O1 and O2) were present. Two operators had a dyad symmetry, wherein each of the inverted repeats consists of 9 bases. Here, the distance between the centers of the dyad symmetry was 50 bases, so that when the LysR protein binds to the O1 and O2 operator sites, the LysR protein was spaced to bind in the same direction. In addition, the 9 bases within the inverted repeat sequence was well conserved in many microorganisms.

The palindromic binding site to the LysR that is reactive to 3-HP was conserved in various microorganisms. However, depending on species, only the O1 operator, i.e., a primary/repression binding site (PBS/RBS), was conserved (Table 3). In addition, in all species, PBS including the conserved $T-N_{11/12}$-A motif and having high affinity was present adjacent to positions −65 and −75 relative to a transcription start site (TSS). That is, the O2 operator, i.e., a secondary/activation binding site (SBS/ABS) motif, had low sequence conservation, so that in silico prediction of the ABS motif is complex and difficult. The RBS and ABS sites were each reported to play a key role in autogenic inhibition and activation. Despite having a common function as proteins that are reactive to 3-HP, the 3-HP-LysR protein had low sequence similarity among other genus and had high sequence similarity within the same genus. Therefore, it is not logically wrong that the DNA sequence of the operator region to which the LysR protein binds is different among different genus. Here, transcription factors (promoters; −10 and −35 regions) were predicted by using BPROM and BDGP tools.

The 9 base sequences shown in Table 3 refer to the conserved regions corresponding to the binding sites to the LysR that is reactive to 3-HP in each genus, wherein the capital letters are bases that appear to be conserved in all target subjects.

TABLE 3

| Genus | Repressive Binding Site ($T-N_{11/12}$-A motif) | # Representatives |
|---|---|---|
| Achromobacter | CAcAcATct | 4 |
| Acidovorax | TcGCAcAcC | 3 |
| Acinetobacter | GTcaAaGAT | 7 |
| Advenella | TTGCAaATT | 4 |
| Aeromonas | GGGcAaaCA | 2 |
| Alcaligenes | CAcAcATct | 5 |
| Alcanivorax | AgCAGCATG | 2 |
| Alicycliphilus | TGCaAAGcc | 2 |
| Anaeromyxobacter | GGGaCGacG | 3 |
| Azospirillum | gTGCCcGCG | 4 |
| Azotobacter | gTatcGAGC | 4 |
| Beijerinckia | ATTgcCgTG | 3 |
| Bordetella | gTTtCGTtG | 6 |
| Bradyrhizobium | AtATATcaG | 3 |
| Brucella | AaaAAtGCa | 3 |
| Burkholderia | GCCtACacT | 16 |
| Corynebacterium | CACCTtTgC | 6 |
| Cupriavidus | AGTtCAgcG | 3 |
| Delftia | GCAAAAAcg | 3 |
| Ferrimonas | GCGGTTTTa | 2 |
| Glaciecola | TgAaTtGAC | 3 |
| Gordonia | GAaaCCGGC | 2 |
| Halomonas | tACACacAA | 3 |
| Janthinobacterium | TtCGcATTa | 3 |
| Marinobacter | CAgaAgGcT | 2 |
| Methylocystis | CGAtCgACC | 2 |
| Phenylobaculum | GTcCCGCtC | 2 |
| Pseudomonas | TTGCAcatC | 24 |
| Ralstonia | GCCtACacT | 5 |
| Shewanella | gTTcGcgTA | 6 |
| Sinorhizobium | TcGgAAaTT | 2 |
| Sphingobium | CgcACaAcC | 2 |
| Stenotrophomonas | GgcCaGATT | 2 |
| Tistrella | CCGGcgGcG | 3 |
| Variovorax | gTcTATTgT | 2 |
| Verminephrobacter | CgTGgcCGA | 2 |
| Vibrio | TGcaCcgTT | 6 |
| Xanthobacter | CTgtGCACa | 2 |
| Xanthomonas | GcgGTGGgC | 6 |

Representitives: The number of species identified as having the same repressive binding site (RBS) within the genus.

TABLE 4

Comparison of enzyme protein sequence homology for C4-LysR, MMSADH, and 3HIBDH

| Enzyme Source | C4-LysR Size (AA) | C4-LysR Identity (%) | MMSADH Size (AA) | MMSADH Identity (%) | 3HIBDH Size (AA) | 3HIBDH Identity (%) | Genbank ID C4-LysR MMSADH 3HIBDH |
|---|---|---|---|---|---|---|---|
| *Achromobacter* sp. | 306 | 47 | 497 | 67 | 296 | 56 | WP_013392250.1 WP_020924676.1 WP_046807163.1 |
| *Acidovorax avenae* subsp. | 295 | 59 | 507 | 82 | 299 | 54 | WP_019701544.1 WP_019701545.1 WP_019701549.1 |
| *Acidovorax* sp. | 301 | 60 | 507 | 82 | 296 | 55 | WP_005799303.1 WP_008905850.1 WP_026437393.1 |
| *Acinetobacter baumannii* | 293 | 49 | 505 | 70 | 296 | 59 | WP_005014261.1 WP_039237888.1 WP_005025914.1 |
| *Aeromonas hydrophilia* | 304 | 36 | 503 | 58 | 306 | 55 | WP_029302009.1 WP_042863805.1 WP_017784754.1 |
| *Agrobacterium* sp. | 293 | 37 | 518 | 47 | 294 | 45 | NA |
| *Alcaligenes faecalis* | 297 | 45 | 497 | 60 | 298 | 55 | WP_026483089.1 WP_045930222.1 WP_026483274.1 |
| *Alcanivorax hongdengensis* | 302 | 39 | 498 | 56 | 287 | 48 | WP_008927645.1 WP_008929937.1 WP_040297229.1 |
| *Alicycliphilus denitrificans* | 304 | 58 | 505 | 81 | 298 | 53 | WP_013519376.1 WP_013519377.1 WP_013519381.1 |
| *Alteromonas marina* | 294 | 35 | 496 | 48 | 291 | 62 | WP_039223538.1 WP_039216373.1 WP_039223543.1 |
| *Anaeromyxobacter dehalogenans* | 313 | 31 | 491 | 53 | 293 | 29 | WP_012631783.1 ABC82015.1 WP_011419642.1 |
| *Azospirillum brasilensse* | 291 | 33 | 499 | 51 | 296 | 53 | EZQ04117.1 WP_014241748.1 WP_035679372.1 |
| *Azotobacter vinelandii* | 296 | 72 | 501 | 92 | 297 | 79 | WP_012699721.1 WP_012699726.1 WP_012699724.1 |
| *Beijerinckia indica* | 301 | 43 | 509 | 50 | 295 | 52 | WP_012383627.1 WP_012383190.1 WP_012383623.1 |
| *Bordetella avium* | 307 | 48 | 497 | 66 | 294 | 58 | WP_012416822.1 WP_012416824.1 WP_012417430.1 |
| *Bradyrhizobium japonicum* | 302 | 42 | 498 | 49 | 296 | 50 | WP_024338218.1 WP_024338217.1 WP_028153398.1 |
| *Burkholderia ambifaria* | 319 | 47 | 509 | 74 | 300 | 65 | WP_012365776.1 WP_012366631.1 WP_006761413.1 |
| *Catenulispora acidiphila* | 296 | 35 | 504 | 42 | 301 | 41 | NA |
| *Caulobacter* sp. | 295 | 31 | 498 | 45 | 295 | 43 | NA |
| *Castellaniella defragrans* | 303 | 46 | 497 | 64 | 297 | 59 | WP_043685951.1 WP_043680927.1 WP_043682533.1 |
| *Chromobacterium violaceum* | 305 | 41 | 500 | 79 | 296 | 58 | WP_043617011.1 WP_045051895.1 WP_043613761.1 |
| *Collimonas arenae* | 319 | 47 | 502 | 67 | 297 | 54 | AIY40998.1 WP_038487725.1 WP_038487728.1 |
| *Comamonas testosteroni* | 300 | 54 | 507 | 83 | 298 | 52 | WP_034389635.1 WP_003075837.1 WP_043003783.1 |
| *Corynebacterium vitaeruminis* | 304 | 28 | 504 | 51 | 291 | 42 | WP_025251982.1 WP_025251535.1 WP_025251536.1 |

TABLE 4-continued

Comparison of enzyme protein sequence homology for C4-LysR, MMSADH, and 3HIBDH

| Enzyme Source | C4-LysR Size (AA) | C4-LysR Identity (%) | MMSADH Size (AA) | MMSADH Identity (%) | 3HIBDH Size (AA) | 3HIBDH Identity (%) | Genbank ID C4-LysR MMSADH 3HIBDH |
|---|---|---|---|---|---|---|---|
| *Cupriavidus necator* | 308 | 40 | 507 | 73 | 296 | 66 | WP_042881289.1 WP_042878263.1 WP_042878261.1 |
| *Carvibacter gracilus* | 296 | 60 | 505 | 82 | 294 | 54 | WP_027474562.1 WP_027474565.1 WP_027474567.1 |
| *Delftia acidovorans* | 300 | 54 | 507 | 82 | 298 | 53 | WP_034393435.1 WP_012205523.1 WP_016453478.1 |
| *Ferrimonas balearica* | 284 | 25 | 497 | 55 | 296 | 51 | ADN76259.1 WP_013344534.1 WP_013344538.1 |
| *Glaciecola nitratireducens* | 281 | 28 | 496 | 56 | 295 | 47 | WP_014109619.1 WP_014108982.1 WP_014108979.1 |
| *Gordonia bronchialis* | 298 | 32 | 513 | 48 | 289 | 46 | WP_041920477.1 WP_012835581.1 WP_012835579.1 |
| *Hahella chejuensis* | 302 | 28 | 498 | 51 | 296 | 51 | NA |
| *Halomonas elongata* | 315 | 44 | 499 | 67 | 300 | 53 | WP_013331269.1 WP_013331270.1 WP_013332181.1 |
| *Hirschia* sp. | 294 | 37 | 498 | 43 | 293 | 45 | NA |
| *Idiomarina* sp. | 312 | 28 | 499 | 57 | 297 | 52 | WP_007420015.1 WP_034729012.1 WP_007419652.1 |
| *Janthinobacterium lividum* | 305 | 46 | 502 | 75 | 297 | 53 | WP_034757572.1 WP_034778805.1 WP_034757584.1 |
| *Kitasatospora setae* | 304 | 31 | 508 | 43 | 298 | 40 | NA |
| *Kutzneria albida* | 300 | 35 | 501 | 45 | 284 | 44 | NA |
| *Methylobacterium* sp. | 302 | 41 | 499 | 47 | 297 | 47 | NA |
| *Methylocystis* sp. | 294 | 30 | 498 | 48 | 295 | 46 | WP_036241816.1 WP_036286001.1 WP_036289118.1 |
| *Novosphingobium* sp. | 316 | 39 | 499 | 45 | 289 | 45 | NA |
| *Oceanimonas smirnovii* | 288 | 28 | 497 | 58 | 297 | 47 | WP_019933245.1 WP_019933168.1 WP_019933171.1 |
| *Paracoccus* sp. | 297 | 38 | 533 | 46 | 302 | 45 | NA |
| *Parvibaculum lavamentivorans* | 304 | 30 | 500 | 52 | 296 | 57 | WP_041536697.1 WP_041536463.1 WP_012111823.1 |
| *Phenylobacterium koreense* | 282 | 32 | 498 | 52 | 298 | 49 | WP_041374440.1 WP_012520768.1 WP_012522231.1 |
| *Photobacterium gaetbuleda* | 303 | 26 | 502 | 53 | 303 | 44 | NA |
| *Polynucleobacter necessarius asymbioticus* | 291 | 49 | 500 | 79 | 298 | 66 | ABP34774.1 ABP34773.1 ABP34771.1 |
| *Pseudoalteromonas carrageenovora* | 299 | 29 | 496 | 55 | 299 | 52 | WP_009840151.1 WP_010381506.1 WP_033103466.1 |
| *Pseudogulbenkiania* sp. | 320 | 46 | 500 | 79 | 298 | 59 | WP_008953966.1 WP_008954515.1 WP_014086932.1 |
| *Pseudomonas denitrificans* ATCC13867 | 298 | 100 | 501 | 100 | 291 | 100 | WP_015477414.1 WP_015477415.1 WP_015477416.1 |
| *Pseudomonas knackmussii* | 298 | 95% | 504 | 93 | 291 | 92 | WP_043252263.1 WP_043252261.1 WP_043252259.1 |
| *Pseudomonas protegens* | 316 | 45 | 508 | 73 | 295 | 62 | WP_041751937.1 WP_011059111.1 WP_015634046.1 |

TABLE 4-continued

Comparison of enzyme protein sequence homology for C4-LysR, MMSADH, and 3HIBDH

| Enzyme Source | C4-LysR Size (AA) | C4-LysR Identity (%) | MMSADH Size (AA) | MMSADH Identity (%) | 3HIBDH Size (AA) | 3HIBDH Identity (%) | Genbank ID C4-LysR MMSADH 3HIBDH |
|---|---|---|---|---|---|---|---|
| Pseudomonas fluorescens | 315 | 45 | 505 | 73 | 295 | 60 | WP_034128788.1 WP_046055588.1 WP_034128786.1 |
| Pseudoxanthomonas spadix | 297 | 27 | 501 | 79 | 297 | 57 | WP_014159583.1 WP_014159749.1 WP_014159753.1 |
| Psychrobacter phenylpyruvicus | 302 | 27 | 495 | 71 | 314 | 52 | WP_028859590.1 WP_028859166.1 WP_028859170.1 |
| Ralstonia oxalatica | 298 | 30 | 515 | 73 | 301 | 65 | NA |
| Rhodomicrobium vannielii | 296 | 30 | 496 | 48 | 296 | 48 | NA |
| Segniliparus rotundus | 300 | 25 | 509 | 51 | 300 | 46 | WP_013137524.1 WP_013137611.1 WP_013137610.1 |
| Shewanella oneidensis | 291 | 24 | 499 | 55 | 300 | 51 | WP_011072126.1 WP_011071828.1 WP_011071832.1 |
| Simiduia agarivorans | 297 | 29 | 505 | 55 | 296 | 47 | NA |
| Sinorhizobium meliloti | 315 | 40 | 498 | 50 | 298 | 52 | WP_018099720.1 WP_027990465.1 WP_027991426.1 |
| Sphingobium chlorophenolicum | 292 | 43 | 499 | 49 | 294 | 48 | WP_037446180.1 WP_037456635.1 WP_037446174.1 |
| Sphingomonas wittichi | 325 | 43 | 503 | 44 | 296 | 46 | NA |
| Sphingopyxis alaskensis | 310 | 36 | 497 | 45 | 291 | 44 | NA |
| Stenotrophomonas maltophilia | 289 | 32 | 501 | 80 | 296 | 57 | WP_044569661.1 WP_019185504.1 WP_005407687.1 |
| Tatlockia micdadei | 293 | 22 | 499 | 45 | 295 | 47 | WP_045099921.1 WP_045098082.1 WP_045098081.1 |
| Thalassospira xiamenensis | 295 | 38 | 499 | 45 | 296 | 48 | NA |
| Variovorax paradoxus | 298 | 60 | 507 | 82 | 300 | 55 | WP_018905631.1 WP_012748355.1 WP_012748351.1 |
| Verminephrobacter eiseniae | 298 | 26 | 507 | 78 | 299 | 51 | WP_011807819.1 WP_011811243.1 WP_011811250.1 |
| Vibrio furnissii | 304 | 25 | 520 | 57 | 300 | 49 | WP_014257826.1 WP_041943477.1 WP_004727845.1 |
| Xanthobacter autotrophicus | 307 | 44 | 498 | 50 | 299 | 51 | WP_012114222.1 WP_012114221.1 WP_041575420.1 |
| Xanthomonas campestri | 301 | 29 | 501 | 77 | 295 | 58 | WP_044099340.1 WP_003488244.1 WP_003488236.1 |
| Xanthomonas oryzae | 304 | 27 | 501 | 77 | 300 | 57 | WP_024711534.1 WP_044750113.1 WP_024744051.1 |

TABLE 5

Comparison of enzyme protein sequence homology for C3-LysR and 3HPDH

| | C3-LysR | | 3HPDH | | Genbank accession no |
|---|---|---|---|---|---|
| Enzyme Source | Size (AA) | Identity (%) | Size (AA) | Identity (%) | C3-LysR / 3HPDH |
| *Achromobacter* sp. | 306 | 45 | 547 | 65 | WP_006223849.1 / WP_006225226.1 |
| *Acidovorax avenae* | 295 | 45 | 564 | 59 | WP_013595009.1 / WP_013592873.1 |
| *Acidovorax* sp. | 301 | 44 | 556 | 61 | WP_020229646.1 / WP_020229941.1 |
| *Acinetobacter baumannii* | 293 | 40 | 534 | 39 | WP_000861803.1 / WP_032868291.1 |
| *Alcaligenes faecalis* | 297 | 42 | 555 | 64 | WP_026483089.1 / ADT64694.1 |
| *Alcanivorax hongdengensis* | 290 | 27 | 531 | 42 | WP_008929468.1 / WP_008927596.1 |
| *Alicycliphilus denitrificans* | 304 | 44 | 560 | 60 | WP_013519376.1 / WP_013721241.1 |
| *Alteromonas marina* | 294 | 36 | 550 | 43 | WP_039223538.1 / WP_039222748.1 |
| *Azospirillum brasilense* | 391 | 35 | 537 | 36 | WP_040137273.1 / WP_035676856.1 |
| *Bordetella avium* | 307 | 45 | 540 | 66 | WP_012416822.1 / WP_012415815.1 |
| *Bradyrhizobium japonicum* | 302 | 41 | 539 | 57 | WP_024338218.1 / WP_028143201.1 |
| *Burkholderia ambifaria* | 323 | 38 | 567 | 60 | WP_006754369.1 / WP_011659279.1 |
| *Castellaniella defragrans* | 303 | 42 | 537 | 63 | WP_043685951.1 / WP_043679553.1 |
| *Chromobacterium violaceum* | 305 | 54 | 556 | 68 | WP_043617011.1 / WP_043617013.1 |
| *Collimonas arenae* | 319 | 44 | 541 | 61 | AIY40998.1 / WP_038494339.1 |
| *Comamonas testosteroni* | 300 | 39 | 555 | 69 | WP_043003771.1 / WP_012836757.1 |
| *Cupriavidus necator* | 308 | 38 | 554 | 61 | WP_042881289.1 / WP_042883575.1 |
| *Carvibacter gracilus* | 296 | 45 | 575 | 57 | WP_027474562.1 / WP_027477384.1 |
| *Delftia acidovorans* | 300 | 41 | 575 | 59 | WP_034393435.1 / WP_043780341.1 |
| *Glaciecola nitratireducens* | 310 | 23 | 533 | 41 | WP_014110217.1 / WP_014110368.1 |
| *Gordonia bronchialis* | 298 | 24 | 443 | 42 | WP_041920477.1 / WP_012835455.1 |
| *Halomonas elongate* | 315 | 42 | 551 | 61 | WP_013331269.1 / WP_013332997.1 |
| *Idiomarina* sp. | 303 | 25 | 564 | 37 | WP_008487425.1 / WP_034821838.1 |
| *Janthinobacterium lividum* | 305 | 44 | 541 | 62 | WP_034788899.1 / WP_010393822.1 |
| *Parvibaculum lavamentivorans* | 304 | 28 | 548 | 40 | WP_041536697.1 / WP_041536013.1 |
| *Polynucleobacter necessarius asymbioticus* | 291 | 41 | 539 | 58 | ABP34774.1 / ABP33573.1 |
| *Pseudogulbenkiania* sp. | 320 | 42 | 547 | 42 | WP_014086927.1 / WP_014087291.1 |
| *Pseudomonas denitrificans* ATCC13867 | 304 | 100 | 554 | 100 | WP_015478424.1 / WP_015478425.1 |
| *Pseudomonas knackmussii* | 301 | 89 | 552 | 85 | WP_043249755.1 / WP_043249752.1 |
| *Pseudomonas protegens* | 297 | 71 | 548 | 75 | WP_041117574.1 / WP_011060785.1 |
| *Pseudomonas fluorescens* | 294 | 72 | 548 | 76 | WP_046048946.1 / WP_038984218.1 |
| *Pseudoxanthomonas spadix* | 307 | 28 | 545 | 43 | WP_043290476.1 / WP_014160845.1 |
| *Psychrobacter phenylpyruvicus* | 302 | 25 | 565 | 40 | WP_028859810.1 / WP_028859590.1 |
| *Segniliparus rotundus* | 300 | 26 | 516 | 37 | WP_013139368.1 / WP_013137524.1 |
| *Sinorhizobium meliloti* | 315 | 37 | 531 | 77 | WP_018094277.1 / WP_010970328.1 |

TABLE 5-continued

Comparison of enzyme protein sequence homology for C3-LysR and 3HPDH

| | Enzyme Source | | | | |
|---|---|---|---|---|---|
| | C3-LysR | | 3HPDH | | Genbank accession no |
| | Size (AA) | Identity (%) | Size (AA) | Identity (%) | C3-LysR 3HPDH |
| *Sphingobium chlorophenolicum* | 292 | 38 | 544 | 40 | WP_037446180.1 WP_037446228.1 |
| *Stenotrophomonas maltophilia* | 289 | 29 | 534 | 44 | WP_037590748.1 WP_044569661.1 |
| *Variovorax paradoxus* | 298 | 44 | 544 | 61 | WP_018905631.1 WP_042580440.1 |
| *Verminephrobacter eiseniae* | 306 | 28 | 556 | 59 | WP_011812258.1 WP_011808703.1 |
| *Vibrio furnissii* | 295 | 27 | 573 | 39 | WP_004729245.1 WP_004724290.1 |
| *Xanthobacter autotrophicus* | 307 | 43 | 556 | 56 | ABS68474.1 WP_012114222.1 |
| *Xanthomonas campestris* | 304 | 30 | 556 | 53 | WP_033484874.1 WP_011038502.1 |

Figure 14A:
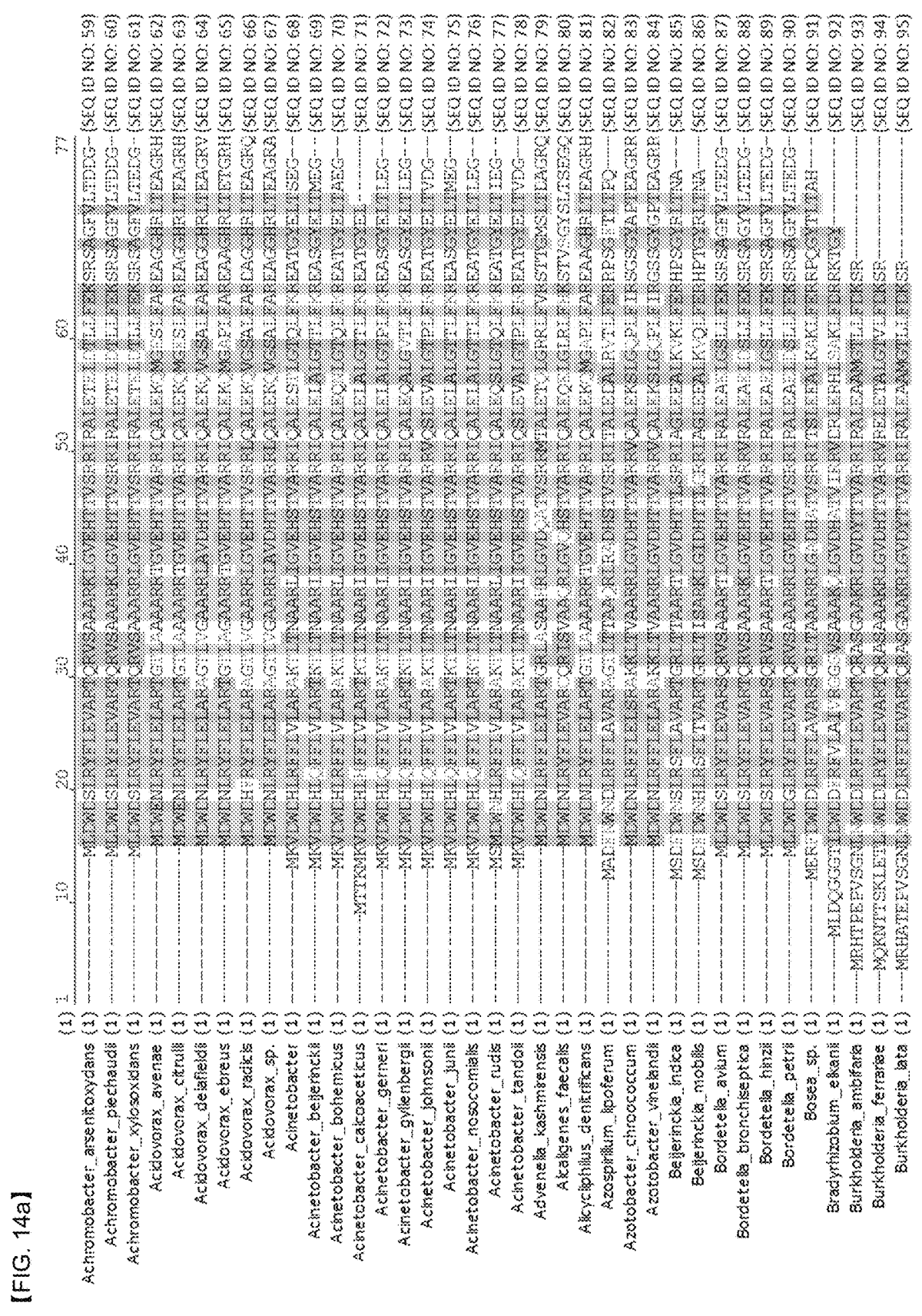
Figure 14B:
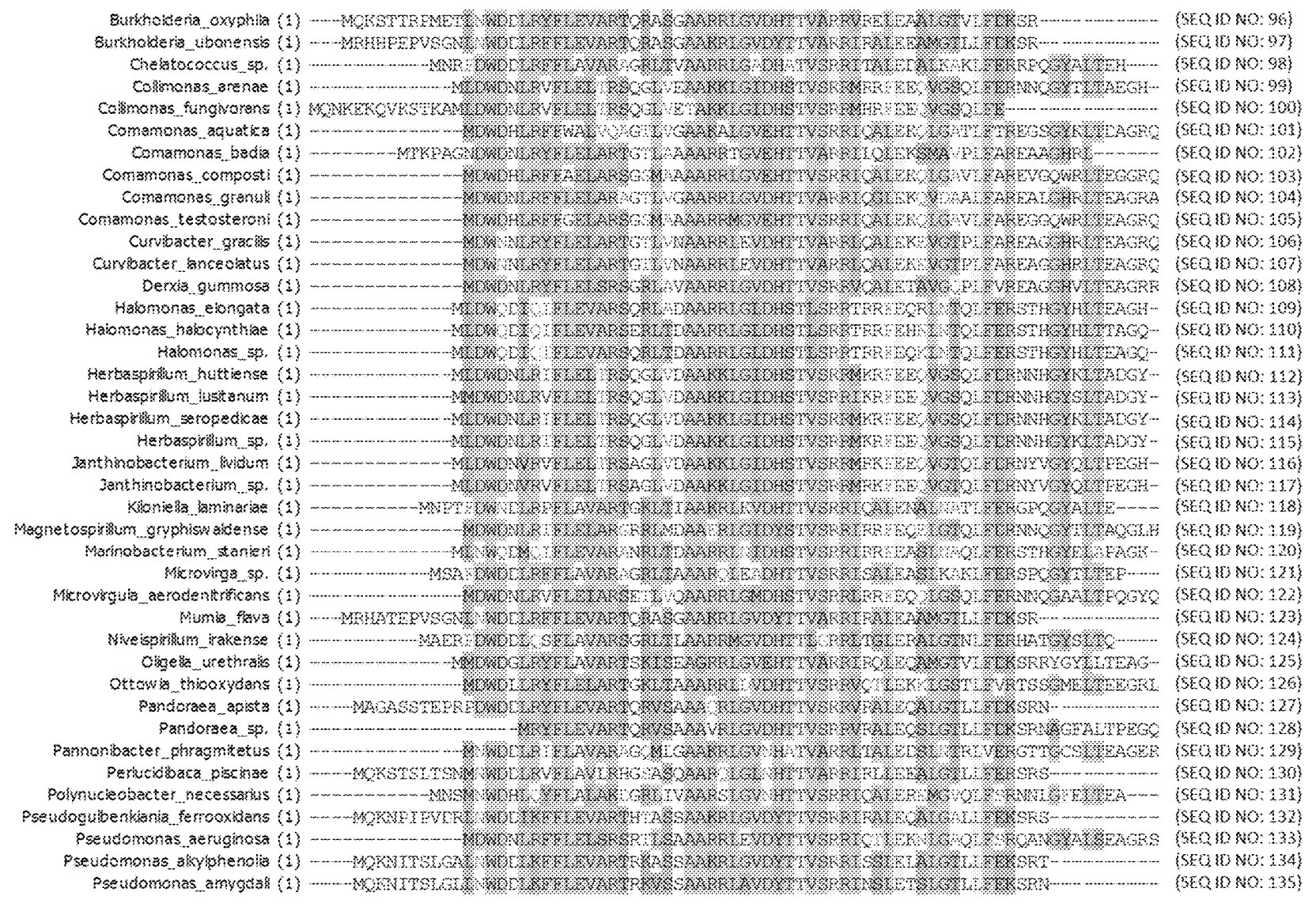
Figure 15B:
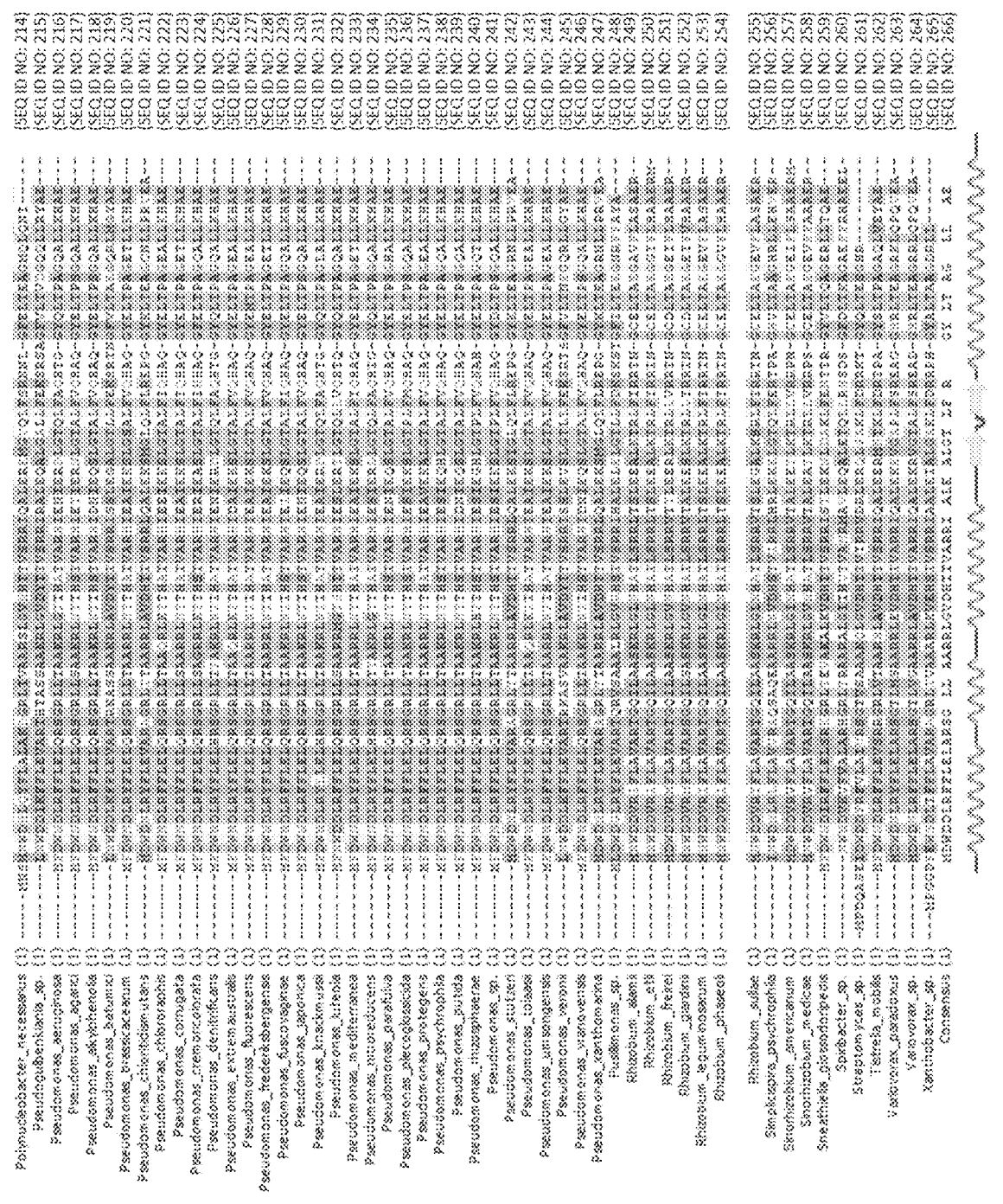

The analysis of the LysR protein was performed in the same manner. As a result BLAST search for the C4 LysR and C3 LysR sequences from the non-redundant NCBI database, it was confirmed that there were 126 and 132 sequences that were homologous to the DNA-binding helix-turn-helix region. FIGS. 14 and 15 show the multiple sequence alignments of these sequences. As a result of the sequence alignments, it was confirmed that a significant portion of the LysR sequences was found to be highly conserved, and that the LysR sequences were also found to be conserved at a high level in other microorganisms. That is, it is suggested that most microorganisms use LysR in cells. In addition, the helix-turn-helix region assumed to bind strongly to the inverted repeat sequences of the operator region in the 3-HP expression promoter in all C4 LysR and C3 LysR sequences was found. In this helix-turn-helix region, four residues, such as Thr-31, Arg-34, Glu-40, and Leu-47, are well conserved. The conserved amino acid residues are considered as important parts in strong interaction upon binding between the LysR protein and DNA (FIG. 9).

To further examine protein-ligand interaction between LysR and 3-HP, homology modeling and docking experiments were carried out. First, a structure available from the PDB database was used, and as a result of comparing sequence similarity of C4-LysR and C3-LysR in *P. denitrificans* using the structure, the sequence similarity of 35% or less was shown (PDB ID: 3SZP, 24% identical). Therefore, the modeling of the C4-LysR and the C3-LysR was carried out according to a threading method using MUSTER and LOMET server. As a result, the predicted C4-LysR and C3-LysR models were purified and verified using RAMPAGE, and it was confirmed by Ramachandran plot that 98% of the amino acid residues were in the appropriate region. Then, the active sites to which 3-HP binds in C4-LysR and C3-LysR were predicted by using COACH. Here, the valid models and the residues at the predicted active sites were used to perform docking experiments in the Maestro program on SCHRODINGER™. Target proteins (C4-LysR and C3-LysR) and a ligand (3-HP) were each examined by using Protein Preparation Wizard and LigPrep Wizard. To produce a grid box, a receptor grid generation tool was used, and ligand docking was performed in the produced grid box by using standard precision (SP) and eXtra precision (XP) docking settings. Consequently, the excellent docking pose was shown when having a docking score of 5.01 for C4-LysR and a docking score of 3.74 for C3-LysR. It was also confirmed that C4-LysR and C3-LysR had interaction with 3-HP and several molecules. Among amino acid residues of C4-LysR, it was examined that Asp-159, Thr-160, Pro-237, and Phe-239 had hydrogen bonding with 3-HP, and ARG24 had hydrophobic interaction with 3-HP (FIG. 9). Among amino acid residues of C3-LysR, it was examined that LEU74, THR190, and THR28 had hydrogen bonding, and THR73, VAL150, PRO167, PHE127, and PHE169 had hydrophobic interaction. Unlike the prediction that there is no interaction between 3-HP and LysR, the docking results interestingly show that 3-HP had strong interaction with a substrate binding domain (ARG94, LYS96, and GLU137) and a helix-turn-helix domain (ARG24) in C4-LysR. In a similar manner, THR28 (helix-turn-helix domain) of C3-LysR was found to have strong interaction with 3-HP. In particular, in a substrate binding domain, in addition to the 3-HP bonding, amino acids that play an important role in the dimer formation have been identified, and the identified amino acids are Ala-60, Gly-91, Arg-94, Pro-118, and Glu-137. In particular, amino acids that play an important role in the dimer formation were all located on the protein surface, except for Pro-118. In this regard, when 3-HP directly affects LysR and causes dimerization of LysR, LysR undergoing dimerization binds to DNA and highly regulates transcription of the 3-HP degrading genes located below the LysR gene.

(5) 3-HP Degradation and Expression of 3-HP Inducible Genes by Microorganisms Having 3-HP Inducible Genes According to the gene structure analysis, the 3-HP degradation pathway was found to be present in various microorganisms. To evaluate the 3-HP degradation ability of various microorganisms, cells were suspended in a 100 mM phosphate solution containing 25 mmol/L of 3-HP and allowed to degrade 3-HP for 24 hours (Table 6). As a result, there was a difference in 3-HP degrading rates depending on the microorganisms, but all of the microorganisms were found to effectively degrade 3-HP. The transcription levels of the 3-HP degrading genes (3hpdh, 3hibdh, and mmsadh) were evaluated depending on the presence of 3-HP (Table 7). As shown in Table 7, 3-HP increased the expression of the 3hpdh, 3hibdh, and mmsadh genes by 6-fold, 14-fold, and 16-fold, respectively in the microorganisms. Such results refer that the 3-HP inducible systems are common in various microorganisms. Meanwhile, in comparison with *P. denitrificans*, the rate of transcription increase in other microorganisms was about 10 times lower than that of *P. denitrificans*, probably due to differences in culture conditions. That is, except for *P. denitrificans*, to improve the growth of other microorganisms, the microorganisms were cultured in a medium supplemented with a large amount of complex nitrogen source, but in this case, in addition to 3-HP, amino acids included in the complex nitrogen source or degradation products of the amino acids activated the transcription of 3hpdh, 3hibdh, and mmsadh at a certain point under conditions where 3-HP was not present so that the amount of the transcription was able to be highly maintained even in the absence of 3-HP.

TABLE 6

3-HP degradation of dormant cells

| Genus No. | Strains | 3-HP degraded (mM)[a] |
|---|---|---|
| 1 | *Achromobacter denitrificans* | 18.40 |
| 2 | *Acidovorax avenae* subsp. *Acidovorax* sp. | 20.43 16.60 |
| 3 | *Acinetobacter baumannii* | 18.76 |
| 4 | *Aeromonas hydrophilia* | 17.88 |
| 5 | *Agrobacterium* sp. | 20.54 |
| 6 | *Alcaligenes faecalis* | 19.32 |
| 7 | *Alcanivorax hongdengensis* | 24.51 |
| 8 | *Alicycliphilus denitrificans* | 20.62 |
| 9 | *Alteromonas marina* | 20.42 |
| 10 | *Amycolatopsis* sp. | 21.13 |
| 11 | *Anaeromyxobacter dehalogenans* | 23.14 |
| 12 | *Azospirillum brasilensse* | 17.96 |
| 13 | *Azotobacter vinelandii* | 19.44 |
| 14 | *Beijerinckia indica* | 23.13 |
| 15 | *Bordetella avium* | 23.87 |
| 16 | *Bradyrhizobium japonicum* | 21.67 |
| 17 | *Burkholderia ambifaria* | 18.33 |
| 18 | *Catenulispora acidiphilia* | 19.45 |
| 19 | *Caulobacter* sp. | 22.34 |
| 20 | *Castellaniella defragrans* | 13.97 |
| 21 | *Chromobacterium violaceum* | 14.56 |
| 22 | *Collimonas arenae* | 16.11 |
| 23 | *Comamonas testosteroni* | 15.96 |
| 24 | *Corynebacterium vitaeruminis* | 17.35 |
| 25 | *Cupriavidus necator* | 18.46 |
| 26 | *Curvibacter gracilus* | 19.12 |
| 27 | *Delftia acidovorans* | 15.89 |

TABLE 6-continued

3-HP degradation of dormant cells

| Genus No. | Strains | 3-HP degraded (mM)[a] |
|---|---|---|
| 28 | *Ferrimonas balearica* | 17.32 |
| 29 | *Glaciecola nitratireducens* | 16.57 |
| 30 | *Gordonia bronchialis* | 18.41 |
| 31 | *Hahella chijuensis* | 17.59 |
| 32 | *Halomonas elongata* | 19.14 |
| 33 | *Hirschia litorea* | 18.47 |
| 34 | *Idiomarina* sp. | 17.86 |
| 35 | *Janthinobacterium lividum* | 18.02 |
| 36 | *Kitasatospora setae* | 19.05 |
| 37 | *Kutzneria albida* | 21.14 |
| 38 | *Methylobacterium* sp. | 23.04 |
| 39 | *Methylocystis* sp. | 16.97 |
| 40 | *Novosphingobium* sp. | 15.87 |
| 41 | *Oceanimonas smirnovii* | 15.91 |
| 42 | *Paracoccus* sp. | 17.96 |
| 43 | *Parvibaculum lavamentivorans* | 18.02 |
| 44 | *Phenylobacterium kunshanensis* | 17.56 |
| 45 | *Photobacterium gaetbuleda* | 19.04 |
| 46 | *Polynucleobacter necessarius asymbioticus* | 16.97 |
| 47 | *Pseudoalteromonas carrageenovora* | 19.03 |
| 48 | *Pseudogulbenkiania* sp. | 7.36 |
| 49 | *Pseudomonas denitrificans* ATCC13867 | 20.53 |
|  | *Pseudomonas knackmussii* | 7.42 |
|  | *Pseudomonas protegens* | 25.24 |
|  | *Pseudomonas fluorescens* | 24.41 |
| 50 | *Pseudoxanthomonas spadix* | 23.01 |
| 51 | *Psychrobacter phenylpyruvicus* | 20.17 |
| 52 | *Ralstonia oxalatica* | 18.09 |
| 53 | *Rhodomicrobium vannielli* | 19.42 |
| 54 | *Segniliparus rotundus* | 8.96 |
| 55 | *Shewanella oneidensis* | 10.14 |
| 56 | *Simiduia agarovorans* | 23.78 |
| 57 | *Sinorhizobium meliloti* | 13.87 |
| 58 | *Sphingobium chlorophenolicum* | 14.76 |
| 59 | *Sphingomonas wittichii* | 21.04 |
| 60 | *Sphingopyxis alaskensis* | 23.56 |
| 61 | *Stenotrophomonas maltophilia* | 15.34 |
| 62 | *Streptomyces nodosus* | 21.13 |
| 63 | *Tatlockia micdadei* | 17.81 |
| 64 | *Thalassospira xiamenensis* | 18.88 |
| 65 | *Variovorax paradoxus* | 19.34 |
| 66 | *Verminephrobacter eiseniae* | 17.04 |
| 67 | *Vibrio furnissii* | 16.98 |
| 68 | *Xanthobacter autotrophicus* | 15.92 |
| 69 | *Xanthomonas campestri* | 14.37 |
|  | *Xanthomonas oryzae* | 13.88 |

[a]The amount of 3-HP degraded was calculated between 0 and 24 h.

TABLE 7

Relative mRNA levels of 3-HP degrading genes

| Genus No. Genus Strains | Strains | 3hpdh | | 3hibdh | | mmsadh | |
|---|---|---|---|---|---|---|---|
| No. | Strains | −3-HP | +3-HP | −3-HP | +3-HP | −3-HP | +3-HP |
| 1 | *Achromobacter denitrificans* | 0.04 | 0.24 | 0.31 | 6.40 | 0.24 | 6.34 |
| 2 | *Acidovorax avenae* subsp. *Acidovorax* sp. | 0.05 0.02 | 0.28 0.31 | 0.34 0.33 | 5.97 6.76 | 0.21 0.36 | 5.98 6.04 |
| 3 | *Acinetobacter baumannii* | 0.01 | 0.19 | 0.35 | 6.02 | 0.27 | 5.76 |
| 4 | *Aeromonas hydrophilia* | — | — | 0.37 | 6.17 | 0.32 | 6.14 |
| 5 | *Agrobacterium* sp. | 0.01 | 0.27 | 0.36 | 6.27 | 0.41 | 6.56 |
| 6 | *Alcaligenes faecalis* | 0.04 | 0.26 | 0.39 | 5.87 | 0.28 | 5.73 |
| 7 | *Alcanivorax hongdengensis* | 0.03 | 0.27 | 0.33 | 6.74 | 0.37 | 6.58 |
| 8 | *Alicycliphilus denitrificans* | 0.07 | 0.30 | 0.31 | 7.01 | 0.25 | 6.01 |
| 9 | *Alteromonas marina* | 0.06 | 0.34 | 0.34 | 6.09 | 0.22 | 5.73 |
| 10 | *Amycolatopsis* sp. | — | — | 0.32 | 5.96 | 0.24 | 6.05 |

TABLE 7-continued

Relative mRNA levels of 3-HP degrading genes

| Genus No. | Strains | 3hpdh | | 3hibdh | | mmsadh | |
|---|---|---|---|---|---|---|---|
| | | −3-HP | +3-HP | −3-HP | +3-HP | −3-HP | +3-HP |
| 11 | *Anaeromyxobacter dehalogenans* | — | — | 0.37 | 6.43 | 0.28 | 5.44 |
| 12 | *Azospirillum brasilensse* | 0.05 | 0.41 | 0.36 | 6.54 | 0.33 | 6.05 |
| 13 | *Azotobacter vinelandii* | — | — | 0.38 | 6.73 | 0.31 | 5.87 |
| 14 | *Beijerinckia indica* | — | — | 0.34 | 6.59 | 0.29 | 5.01 |
| 15 | *Bordetella avium* | 0.08 | 0.45 | 0.31 | 6.04 | 0.24 | 4.98 |
| 16 | *Bradyrhizobium japonicum* | 0.07 | 0.52 | 0.41 | 7.21 | 0.34 | 5.49 |
| 17 | *Burkholderia ambifaria* | 0.03 | 0.31 | 0.29 | 5.94 | 0.21 | 5.13 |
| 18 | *Catenulispora acidiphilia* | 0.05 | 0.41 | 0.32 | 5.84 | 0.25 | 5.24 |
| 19 | *Caulobacter sp.* | 0.04 | 0.45 | 0.35 | 5.96 | 0.24 | 5.96 |
| 20 | *Castellaniella defragrans* | — | — | 0.45 | 7.43 | 0.37 | 5.98 |
| 21 | *Chromobacterium violaceum* | 0.02 | 0.25 | 0.38 | 7.02 | 0.32 | 6.31 |
| 22 | *Collimonas arenae* | — | — | 0.37 | 7.20 | 0.30 | 5.87 |
| 23 | *Comamonas testosteroni* | 0.04 | 0.24 | 0.28 | 5.88 | 0.21 | 4.96 |
| 24 | *Corynebacterium vitaeruminis* | 0.03 | 0.28 | 0.47 | 6.99 | 0.34 | 5.89 |
| 25 | *Cupriavidus necator* | 0.02 | 0.21 | 0.42 | 6.84 | 0.33 | 6.05 |
| 26 | *Curvibacter gracilus* | — | — | 0.29 | 5.76 | 0.19 | 3.99 |
| 27 | *Delftia acidovorans* | — | — | 0.33 | 6.34 | 0.26 | 4.03 |
| 28 | *Ferrimonas balearica* | — | — | 0.41 | 7.04 | 0.34 | 5.17 |
| 29 | *Glaciecola nitratireducens* | 0.05 | 0.30 | 0.36 | 7.11 | 0.29 | 4.81 |
| 30 | *Gordonia bronchialis* | 0.04 | 0.29 | 0.45 | 6.99 | 0.33 | 5.21 |
| 31 | *Hahella chijuensis* | 0.03 | 0.28 | 0.42 | 6.81 | 0.34 | 5.97 |
| 32 | *Halomonas elongata* | 0.06 | 0.32 | 0.27 | 5.41 | 0.19 | 4.34 |
| 33 | *Hirschia litorea* | 0.05 | 0.34 | 0.29 | 6.19 | 0.18 | 4.56 |
| 34 | *Idiomarina sp.* | 0.08 | 0.42 | 0.47 | 7.21 | 0.32 | 5.43 |
| 35 | *Janthinobacterium lividum* | 0.03 | 0.33 | 0.41 | 6.98 | 0.29 | 5.01 |
| 36 | *Kitasatospora setae* | 0.04 | 0.36 | 0.39 | 6.46 | 0.25 | 5.25 |
| 37 | *Kutzneria albida* | 0.03 | 0.41 | 0.35 | 5.96 | 0.24 | 5.61 |
| 38 | *Methylobacterium sp.* | 0.05 | 0.45 | 0.33 | 6.02 | 0.23 | 598 |
| 39 | *Methylocystis sp.* | — | — | 0.32 | 6.51 | 0.21 | 4.91 |
| 40 | *Novosphingobium sp.* | 0.04 | 0.39 | 0.29 | 5.98 | 0.25 | 6.04 |
| 41 | *Oceanimonas smirnovii* | 0.02 | 0.24 | 0.36 | 6.44 | 0.28 | 4.88 |
| 42 | *Paracoccus sp.* | 0.03 | 0.25 | 0.34 | 6.32 | 0.27 | 4.96 |
| 43 | *Parvibaculum lavamentivorans* | 0.04 | 0.28 | 0.46 | 7.31 | 0.32 | 4.99 |
| 44 | *Phenylobacterium kunshanensis* | 0.06 | 0.33 | 0.41 | 7.43 | 0.33 | 5.02 |
| 45 | *Photobacterium gaetbuleda* | — | — | 0.36 | 7.02 | 0.29 | 5.06 |
| 46 | *Polynucleobacter necessarius asymbioticus* | 0.09 | 0.45 | 0.39 | 6.99 | 0.27 | 5.37 |
| 47 | *Pseudoalteromonas carrgeenovora* | — | — | 0.29 | 5.76 | 0.21 | 5.03 |
| 48 | *Pseudogulbenkiania sp.* | 0.04 | 0.26 | 0.32 | 5.98 | 0.23 | 5.36 |
| 49 | *Pseudomonas denitrificans* ATCC13867 | 0.03 | 0.23 | 0.39 | 6.20 | 0.26 | 5.43 |
| | *Pseudomonas knackmussii* | 0.03 | 0.25 | 0.41 | 6.81 | 0.35 | 5.96 |
| | *Pseudomonas protegens* | 0.02 | 0.19 | 0.28 | 5.62 | 0.21 | 5.01 |
| | *Pseudomonas fluorescens* | 0.04 | 0.27 | 0.26 | 5.81 | 0.18 | 4.70 |
| 50 | *Pseudoxanthomonas spadix* | — | — | 0.31 | 5.99 | 0.27 | 4.96 |
| 51 | *Psychrobacter phenylpyruvicus* | 0.08 | 0.37 | 0.43 | 7.04 | 0.31 | 5.03 |
| 52 | *Ralstonia oxalatica* | — | — | 0.40 | 7.21 | 0.34 | 5.21 |
| 53 | *Rhodomicrobium vannielii* | 0.05 | 0.41 | 0.39 | 7.01 | 0.32 | 6.02 |
| 54 | *Segniliparus rotundus* | 0.07 | 0.27 | 0.25 | 5.81 | 0.19 | 4.32 |
| 55 | *Shewanella oneidensis* | 0.05 | 0.28 | 0.25 | 5.81 | 0.19 | 4.07 |
| 56 | *Simiduia agarovorans* | 0.03 | 0.29 | 0.23 | 5.76 | 0.21 | 4.87 |
| 57 | *Sinorhizobium meliloti* | — | — | 0.24 | 5.79 | 0.16 | 4.07 |
| 58 | *Sphingobium chlorophenolicum* | 0.06 | 0.33 | 0.33 | 5.99 | 0.23 | 4.86 |
| 59 | *Sphingomonas wittichii* | 0.03 | 0.45 | 0.31 | 7.02 | 0.32 | 6.42 |
| 60 | *Sphingopyxis alaskensis* | — | — | 0.35 | 7.00 | 0.35 | 6.94 |
| 61 | *Stenotrophomonas maltophilia* | 0.04 | 0.31 | 0.29 | 6.02 | 0.24 | 5.21 |
| 62 | *Streptomyces nodosus* | 0.07 | 0.39 | 0.43 | 6.72 | 0.34 | 5.14 |
| 63 | *Tatlockia micdadei* | — | — | 0.47 | 6.61 | 0.36 | 5.65 |
| 64 | *Thalassospira xiamenensis* | — | — | 0.32 | 7.02 | 0.33 | 6.10 |
| 65 | *Variovorax paradoxus* | — | — | 0.38 | 6.59 | 0.28 | 4.97 |
| 66 | *Verminephrobacter eiseniae* | 0.08 | 0.43 | 0.42 | 6.43 | 0.30 | 5.14 |
| 67 | *Vibrio furnissii* | 0.05 | 0.39 | 0.39 | 6.03 | 0.27 | 4.91 |
| 68 | *Xanthobacter autotrophicus* | 0.04 | 0.27 | 0.27 | 6.23 | 0.21 | 5.41 |
| 69 | *Xanthomonas campestri* | 0.03 | 0.25 | 0.24 | 5.81 | 0.18 | 5.09 |
| | *Xanthomonas oryzae* | 0.02 | 0.19 | 0.45 | 6.43 | 0.34 | 5.19 |

Analysis of 3-HP inducible promoters was performed on the microorganism above. In the same manner as in *P. denitrificans* of the previous case, all of the promoters had O1 and O2 operator sequences, and it was confirmed that these sequences had a palindromic structure consisting of 9 bases. Although no further studies on these sequences have been made yet, binding to the LysR protein was expected in the same manner as in *P. denitrificans*.

In conclusion, to improve the 3-HP production in a biological manner, it is necessary to continuously produce new enzymes with enzyme activity. In the present invention, transcriptional regulators that are reactive to 3-HP and promoters have been screened from microorganisms including *P. denitrificans*, wherein the transcriptional regulators and promoters consist of LysR proteins and specific gene sequences binding to the LysR proteins. In addition, in the presence of 3-HP, it was found that the LysR family transcriptional regulator up-regulated the expression of the corresponding genes.

The molecular modeling and docking experiments showed the presence of important residues for C4-LysR (ARG94, LYS96, GLU137, and ARG24) and C3-LysR (LEU74, THR190, THR28, THR73, VAL150, PRO167, PHE127, and PHE169). Therefore, the 3-HP inducible system is expected to be effectively used to regulate the 3-HP metabolic pathway.

<Example 2> Optimization of 3-HP Production Pathway in *P. denitrificans*

1. Strains, Plasmids, and Experimental Materials

Bacterial species and plasmids used in the present study were shown in Table 8. An *E. coli* strain was provided from KCTC and a *P. denitrificans* strain was provided from ATCC. *E. coli* XL1-Blue was used for plasmid cloning and maintenance. A genome DNA separation kit and a pGEM-T vector were purchased from Promega (Madison, Wis., USA), a high-performance pfx polymerase was purchased from Invitrogen (Seoul, Korea), a DNA modification enzyme was purchased from New England Bio-Labs (Beverly, Mass., USA), and a Miniprep and DNA gel extraction kit was purchased from Qiagen (Mannheim, Germany). In addition, primers were purchased from Cosmogenetech Co. Ltd. (Seoul, Korea), bacto tryptone and yeast extract were purchased from Difco (Becton Dickinson; Franklin Lakes, N.J., USA), and other chemicals and enzymes were purchased from Sigma-Aldrich (St. Louis, Mo., USA).

TABLE 8

Bacterial species and plasmids used in the present study

| Strains | Analysis contents | Source |
|---|---|---|
| *E. coli* DH5α | Cloning host | KCTC, Korea |
| *P. denitrificans* wt | *P. denitrificans* ATCC13867; Source for 3hibdhlV and 3hpdh promoters and terminators | ATCC, America |
| Δ3hpdhΔ3hibdhlV | *P. denitrificans* ATCC13867 Δ3hpdhΔ3hibdhlV double mutant strain | Zhou et al. 2014 |
| Δ3hpdhΔ3hibdhlVΔ3hibdhl | *P. denitrificans* ATCC13867 Δ3hpdhΔ3hibdhlVΔ3hibdhl triple mutant strain | This study |
| Plasmids | | |
| pGEM-T | lacZa; cloning vector; pGEM 5zf(+) derivative; 3T-overhang; Amp$^r$ | Promega |
| pUCP19 | ColE1-ori; pRO1614-ori; broad-host-range cloning vector; Amp$^r$ | West et al. 1994 |
| pUCPK/ P$_{C3}$-dhaB-gdrAB, P$_{C4}$-KGSADH | KGSADH gene amplified from pQKS1 were overlapped with 3hibdhlV promoter and terminator and cloned in pUCPK/P$_{C3}$-dhaB-gdrAB; Km$^r$ | This study |
| pUCPK/ P$_{C3}$-gdrAB-dhaB, P$_{C4}$-KGSADH | gdrAB and dhaB gene order were switched and cloned in pUCPK/P$_{C4}$-KGSADH,; Km$^r$ | This study |

2. Development of Δ3hpdhΔ3hibdhlVΔ3hibdhl Deletion Mutant Strain of *P. denitrificans*

To understand the role of the 3-HP degrading genes, 3hibdhl was removed from the chromosome of *P. denitrificans* Δ3hpdhΔ3hibdhlV. A target gene was deleted therefrom based on a sacB negative counter-selection system. A sacB-Km cassette was introduced to NdeI and XbaI restriction sites of pQE-80L to prepare a pQSAK plasmid which is to be used for removal of the target gene. The genome DNA of *P. denitrificans* was used to obtain a DNA fragment including ~700 bp upstream and downstream of the target gene by PCR. After DNA sequencing thereon, the DNA fragment was cloned into a pGEM-T vector. Afterwards, sub-cloning into the pQSAK plasmid was made again, and then, a mutant strain of *P. denitrificans* was developed through two rounds of recombination. The mutant strain was re-identified by PCR and sequencing performed thereon. The mutant strains thus obtained was designated as *P. denitrificans* Δ3hpdhΔ3hibdhlVΔ3hibdhl.

3. Plasmid Construction

A gene encoding glycerol dehydratase and reactivation enzyme was amplified by using a pUCPK'/PC3-dhaB-gdrAB, PC4-KGSADH plasmid, and an expression cassette was constructed by cloning a C3 promoter and a C3 terminator onto promoters at the 5'-end and 3'-end of gdrAB and dhab123 genes, respectively. The expression cassette was replicated at XbaI and SacI restriction sites of the pUCPK'/PC3-dhaB-gdrAB, PC4-KGSADH plasmid, and a resulting plasmid was designated as pUCPK'/PC3-gdrAB-dhaB, PC4-KGSADH. The pUCPK'/PC3-gdrAB-dhaB, PC4-KGSADH plasmid thus obtained was transformed with *P. denitrificans* Δ3hpdhΔ3hibdhlVΔ3hibdhl, and finally, a Pd Δ3hpdhΔ3hibdhlVΔ3hibdhl (pUCPK'/PC3-gdrAB-dhaB, PC4-KGSADH) plasmid was constructed (FIG. 16).

4. Determination of Enzyme Activity

The DhaB activity can be measured by measuring the KGSADH enzyme activity. 1 unit of the DhaB activity is defined as the amount of enzyme required to reduce 1 μmol of NAD+ to NADH for 1 minute. Briefly, first, 20 ul of 26

U/mg NAD+-dependent KGSADH was cultured at a temperature of 37° C. for 5 minutes in 50 mM potassium phosphate buffer (pH 8.0) (total volume of 1 mL) containing 1 mM DTT, 15 uM coenzyme B12, 3 mM $MgCl_2$, and 1.5 mM ATP. Here, KGSADH contained 25% glycerol. A reaction was started by the addition of an appropriate amount of a cell extract containing 1.5 mM NAD+ and DhaB preheated at a temperature of 37° C., and was observed through changes in absorbance of NADH. The KGSADH activity was determined according to the method reported by Dr. Raj by measuring the reduction from NAD+ to NADH at 340. A reaction mixture including 50 mM potassium phosphate buffer (pH 8.0), 1 mM DTT, and an appropriate amount of an enzyme extract was cultured at a temperature of 37° C. for 5 minutes, and a reaction was initiated by the addition of 2.0 mM 3-HPA and 2.0 mM NAD+. The amount of NADH was determined by using $6.22\times10^3$ $M^{-1}$ $cm^{-1}$ of molar extinction coefficient ($\Delta\epsilon340$). 1 unit activity of KGSADH is defined as the amount of enzyme required to reduce 1 μmol of NAD+ to NADH for 1 minute. All enzyme activities were measured by using a crude cell extract.

5. Culture Medium and Culture Conditions

Unless otherwise stated, shaking culture was performed by using a 250 mL non-baffled Erlenmeyer flask containing 20 mL of a culture broth at a speed of 200 rpm at a temperature of 30° C. Here, an M9 culture medium supplemented with, per liter, $MgSO_4$, 0.25 g; NaCl, 1.0 g; $NH_4Cl$, 1.0 g; yeast extract, 1 g; glycerol, 100 mmol; L-glutamate, 5 g; tryptone, 2 g; and glucose 2.5 g was used, and the medium contained 100 mM potassium phosphate buffer (pH 7.0). If necessary, 12 μmol/L of coenzyme B12 was additionally injected, and then, the flask was sealed with an oxygen-permeable sponge plug. For the measure of cell mass, residual substrates, and metabolites, sampling was periodically done, and all shaking culture experiments were repeated three times, wherein a standard deviation of biomass and metabolites was less than 10%. The bioreactor experiments were carried out in a 1-L working volume in a 1.5-L capacity Biotron-LiFlus GM bioreactor (Biotron, Seoul, Korea).

An M9 culture medium for the bioreactor experiments was supplemented with, per liter, $MgSO_4$—$H_2O$, 0.25 g; NaCl, 1.0 g; $NH_4Cl$, 1.0 g; yeast extract, 1 g; L-glutamate, 5 g; tryptone, 2 g; casamino acids, 2 g; glucose 2.5 g, and trace element solution, 10 mL/L, and the medium contained 100 mM of potassium phosphate buffer (pH 7.0). The culturing was performed in a fed-type culturing mode at a temperature of 30° C. while concentrated glycerol (10 M) and 7 mM glucose were periodically injected thereto. Here, pH was maintained to 7.0±0.1 by using 5 N NaOH and 2.5 N HCl. Air was continuously supplied at an agitation speed of 650 rpm at 1 vvm. During the culturing, a medium supplemented with tryptone, 2 g/L; casamino acids, 2 g/L; L-glutamate, 5.0 g/L; and yeast extract, 1 g/L was added every 6 hours to the bioreactor. Samples thereof were regularly analyzed to measure cell mass, residual substrates, and metabolites.

6. Analysis Method

The cell concentration was measured by using a spectrophotometer (Lambda 20, Perkin Elmer; Norwalk, Conn., USA) with a cuvette having a length of 10 mm. 1 unit of absorbance at 600 nm (OD600) was consistent with a dry cell volume of 0.3 g per liter. The protein concentration was analyzed according to a Bradford method with a microtiter plate reader based on bovine serum albumin (1420, Wallac Victor 2; Perkin Elmer). The concentrations of glycerol, 3-HP, and other metabolites were measured by HPLC, wherein the supernatant obtained by centrifugation performed on a culturing sample for 10 minutes at 10,000×g was filtered through a tuffryn-membrane (Acrodisc, Pall Life Sciences), and then, was eluted with by 300 mm×7.8 mm Aminex HPX-87H (Bio-Rad, USA) column using 2.5 mM $H_2SO_4$ as a mobile phase at a temperature of 65° C.

7. Results (1) Shaking Flask Culture of Recombinant Pd Δ3hpdhΔ3hibdhIVΔ3hibdhI (pUCPK'/PC3-gdrAB-dhaB, PC4-KGSADH)

The inventors of the present invention had observed in the previous study that the DhaB activity was significantly reduced due to self-destructive catalytic reaction by DhaB when glycerol conversion occurred. Such reduction may be caused by low expression of GdrAb that reactivates DhaB. In addition, it was also expected that the expression of GdrAB would be improved by sequentially arranging GdrAB and DhaB right below the PC3 promoter. Based on this hypothesis, a pUCPK'/PC3-gdrAB-dhaB, PC4-KGSADH plasmid was developed and introduced to a P. denitrificans (hereinafter, referred to as Pd) Δ3hpdhΔ3hibdhIVΔ3hibdhI strain for the production of 3-HP. The effect of changing the arrangement order of GdrAB and DhaB regarding the 3-HP production from glycerol was measured in Pd Δ3hpdhΔ3hibdhIVΔ3hibdhI (pUCPK'/PC3-gdrAB-dhaB, PC4-KGSADH). The supplying effect of coenzyme B12 was examined by supplying 12 μM of coenzyme B12 at 0 h. Pd Δ3hpdhΔ3hibdhIVΔ3hibdhI (pUCPK'/PC3-dhaB-gdrAB, PC4-KGSADH) was used as a control group. S1~S3 in FIG. 17 shows the production of 3-HP from glycerol by recombinant Pd Δ3hpdhΔ3hibdhIVΔ3hibdhI (pUCPK'/PC3-gdrAB-dhaB, PC4-KGSADH), and O1~O3 in FIG. 17 shows the production of 3-HP from glycerol by recombinant Pd Δ3hpdhΔ3hibdhIVΔ3hibdhI (pUCPK'/PC3-dhaB-gdrAB, PC4-KGSADH). S1 and O1 in FIG. 17 show the results in the case where there was no supply of glycerol, and S2 and O2 of FIG. 17 show the results in the case where there was no supply of coenzyme B12. Meanwhile, S3 and O3 of FIG. 17 show the results obtained in associated with supply of coenzyme B12. It was confirmed that there was no significant difference in cell growth between the two strains. However, the production of 3-HP by the Pd Δ3hpdhΔ3hibdhIVΔ3hibdhI (pUCPK'/PC3-gdrAB-dhaB, PC4-KGSADH) strain supplied with cobalt and coenzyme B12 increased to 41% and 29% after 12 hours. These results indicate that the rate of DhaB reaction was affected by the amount of coenzyme or the amount of cobalt.

It was observed that the addition of cobalt led to the production of 3-HPA and 1,3-PDO at 12 h, but in a control strain, it was observed that 3-HPA (with cobalt) was not accumulated (Table 9). The yield of 3-HP from glycerol was about 1, meaning that glycerol supplied thereto was completed used for the production of 3-HP, and the produced 3-HP was not degraded again.

TABLE 9

Carbon distribution in 12-h culture of recombinant
P. denitrificans Δ3hpdhΔ3hibdhIVΔ3hibdhI

|  | S2 | S3 | O2 | O3 |
|---|---|---|---|---|
| substrates |  |  |  |  |
| Glucose (mM) | 0.58 | 0.91 | 0.67 | 0.88 |
| Glycerol (mM) | 64.13 | 52.15 | 44.92 | 37.45 |
| Biomass (g/L) | 1.51 | 1.36 | 1.66 | 1.17 |

TABLE 9-continued

Carbon distribution in 12-h culture of recombinant
*P. denitrificans* Δ3hpdhΔ3hibdhIVΔ3hibdhI

| | S2 | S3 | O2 | O3 |
|---|---|---|---|---|
| Metabolites | | | | |
| 3-HP (mM) | 64.83 | 49.51 | 45.93 | 38.24 |
| 3-HPA (mM) | 0.78 | 0.52 | 0 | 0.39 |
| 1,3-PDO (mM) | 3.55 | 4.95 | 1.37 | 1.42 |
| Growth rate ($\mu_{max}$, h$^{-1}$) | 0.56 | 0.54 | 0.54 | 0.53 |
| 3-HP yield on glycerol (mol/mol) | 1.01 | 0.95 | 1.02 | 1.02 |
| Glycerol carbon recovery (%) | 1.08 | 1.05 | 1.05 | 1.07 |

(2) Enzyme Activity

Time-dependent in vitro enzyme activity of DhaB and KGSADH was measured (FIG. 18). The DhaB enzyme activity was examined by using the KGSADH enzyme activity, and the KGSADH enzyme activity was measured by using propionaldehyde as a substrate. When the order of DhaB and GdrAB genes was changed, it was observed that the DhaB activity was reduced. Meanwhile, the addition of glycerol, cobalt, or coenzyme B12 was observed to rather cause significant reduction in the DhaB enzyme activity. In this regard, additional experiments are needed to determine whether such effects are caused by the accumulation of 3-HPA or other factors. However, one thing that is clear is that changing of the order of gdrAB and DhaB was not enough to sufficiently improve the DhaB enzyme activity. Thus, it is unclear whether the expression of gdrB is improved in the recombinant strain used herein. For the gdrB translation, RBS of *Klebsiella pneumonia* was used, but further verification thereof is required.

(3) Bioreactor Culture of DhaB, KGSADH Overexpression Recombinant Pd Δ3hpdhΔ3hibdhIVΔ3hibdhI (pUCPK'/PC3-gdrAB-dhaB, PC4-KGSADH)

A fed-type glycerol-glucose bioreactor bioreactor operation was performed by using Pd Δ3hpdhΔ3hibdhIVΔ3hibdhI (pUCPK'/PC3-gdrAB-dhaB, PC4-KGSADH) and Pd Δ3hpdhΔ3hibdhIVΔ3hibdhI (pUCPK'/PC3-dhaB-gdrAB, PC4-KGSADH) strains. In the bioreactor experiments, the concentrations of glucose and glycerol were maintained at low levels of 10 mM and 150 mM, respectively. For every 6 hours, glutamate was supplied for cell growth. As a result of the culture, similar cell growth was observed in the two bioreactors. The cell growth decreased in both cultures after 9 hours, but the cell growth continued until the end of the reaction. In bioreactor A, a Pd Δ3hpdhΔ3hibdhIVΔ3hibdhI (pUCPK'/PC3-dhaB-gdrAB, PC4-KGSADH) strain was used (FIG. 19). Here, the production of 3-HP mostly increased up to 36 hours, resulting in an amount of more than 58±2 g/L at a production rate of 1.2 g/L/h or more, and a 3-HP yield of more than 0.9 mol/mol from glycerol. The 3-HP production rate decreased after 36 hours. Between 36 hours to 48 hours, only 2±0.5 g/L of the 3-HP production was maintained. Overall, for 48 hours, based on a production rate of 1.0 g/L/h and a 3-HP yield of 0.93 mol/mol from glycerol, 60±2 g/L of 3-HP was produced. In comparison with previous experiments, i.e., the fermentation experiment of the strain in which 3hibdhI was not deleted, the yield of 3-HP was significantly increased, confirming that 3hibdhI had an important role in the 3-HP degradation. The influence of 3hibdhI was not observed at all in the flask experiments with short fermentation times.

In bioreactor B, the strain in which the gene order (dhaB and gdrAB) was changed was used, and as a result, the production of 3-HP was improved in the latter half of fermentation. Based on a production rate of 1.3 g/L/h and a yield of 0.95 mol/mol from glycerol, about 63±2 g/L of 3-HP was produced. In comparison with bioreactor A, the 3-HP production was increased by 5%. Although the results were not seen in the enzyme activity assays or flask experiments, the degree of GdrAB expression was significantly important in terms of the 3-HP production.

In conclusion, when the 3-HP production enzymes, i.e., DhaB, GdrAB, and KGSADH, were expressed, *P. denitrificans* was able to produce 3-HP from glycerol. The recombinant plasmids were developed by using two strong inducible promoters, PC3 and PC4, and Pd Δ3hpdhΔ3hibdhIVΔ3hibdhI from which three genes were deleted was used as a host. To alleviate the degree of inactivation of DhaB, gdrAB was located in front of dhaB, so as to enhance the expression of gdrAB. The enzyme activity analysis and protein expression analysis by SDS-PAGE showed that the activity of DhaB was reduced by such a positional change. However, regardless of the reduced activity of DhaB, the production of 3-HP was improved. As a result of operating the fed-type bioreactor using new recombinant strains, 3-HP was obtained in high concentrations, high production rates, and high yields.

The invention claimed is:

1. A recombinant gene expression cassette reactive to 3-hydroxypropionic acid (3-HP) or a derivative thereof, wherein the derivative is 3-hydroxyisobutyrate (3HIB) or 3-hydroxybutyrate (3-HB),
   the recombinant gene expression cassette comprising:
   a lysR gene encoding a LysR protein that is reactive to 3-HP or a derivative thereof;
   a promoter comprising a binding site to a LysR protein; and
   a gene encoding a target expression protein,
   wherein the binding site to a LysR protein comprises
   a base sequence selected from SEQ ID NOs: 5 to 43, or an inverted repeat sequence having a base sequence selected from SEQ ID NOs: 5 to 43 and an inverted repeat sequence paired with therewith are repeated twice.

2. The recombinant gene expression cassette of claim 1, wherein the LysR protein or the promoter is derived from a microorganism having degradability of 3-HP.

3. The recombinant gene expression cassette of claim 2, wherein the microorganism having degradability of 3-HP is one selected from the group consisting of *Achromobacter denitrificans*, *Acidovorax avenae* subsp., *Acidovorax sp.*, *Acinetobacter baumannii*, *Aeromonas hydrophilia*, *Agrobacterium sp.*, *Alcaligenes faecalis*, *Alcanivorax hongdengensis*, *Alicycliphilus denitrificans*, *Alteromonas marina*, *Amycolatopsis sp.*, *Anaeromyxobacter dehalogenans*, *Azospirillum brasilense*, *Azotobacter vinelandii*, *Beijerinckia indica*, *Bordetella avium*, *Bradyrhizobium japonicum*, *Burkholderia ambifaria*, *Catenulispora acidiphilia*, *Caulobacter sp.*, *Castellaniella defragrans*, *Chromobacterium violaceum*, *Collimonas arenae*, *Comamonas testosteroni*, *Corynebacterium vitaeruminis*, *Cupriavidus necator*, *Curvibacter gracilis*, *Delftia acidovorans*, *Ferrimonas balearica*, *Glaciecola nitratireducens*, *Gordonia bronchialis*, *Hahella chijuensis*, *Halomonas elongata*, *Hirschia litorea*, *Idiomarina sp.*, *Janthinobacterium lividum*, *Kitasatospora setae*, *Kutzneria albida*, *Methylobacterium sp.*, *Methylocystis sp.*, *Novosphingobium sp.*, *Oceanimonas smirnovii*, *Paracoccus sp.*, *Parvibaculum lavamentivorans*, *Phenylobacterium kunshanensis*, *Photobacterium gaetbuleda*, *Polynucleobacter necessarius asymbioticus*, *Pseudoalteromonas carrageenovora*, *Pseudogulbenkiania sp.*, *Pseudomonas denitrificans* ATCC 13867, *P. knackmussii*, *P. protegens*, *P. fluorescens*, *Pseudoxanthomonas spadix*, *Psychrobacter phenylpyruvicus*, *Ralstonia oxalatica*, *Rhodomicrobium vannielli*, *Segnihparus rotundus*, *Shewanella oneidensis*, *Simiduia agarovorans*, *Sinorhizobium meliloti*, *Sphingobium chlorophenolicum*, *Sphingomonas wittichii*, *Sphingopyxis alaskensis*, *Stenotrophomonas maltophilia*, *Streptomyces nodosus*, *Tatlockia micdadei*, *Thalassospira xiamenensis*, *Variovorax paradoxus*, *Verminephrobacter eiseniae*, *Vibrio furnissii*, *Xanthobacter autotrophicus*, *Xanthomonas campestri*, and *Xanthomonas oryzae*.

4. The recombinant gene expression cassette of claim 1, wherein the LysR protein comprises an N-terminal domain having a helix-turn-helix structure and binding to DNA, a C-terminal domain binding to 3-HP or a derivative thereof, and a C-terminal domain contributing to stabilization of a LysR protein dimer.

5. The recombinant gene expression cassette of claim 4, wherein the N-terminal domain having a helix-turn-helix structure and binding to DNA comprises an amino acid sequence represented by SEQ ID NO: 1 or 2.

6. The recombinant gene expression cassette of claim 4, wherein the C-terminal domain binding to 3-HP or a derivative thereof comprises an amino acid sequence represented by SEQ ID NO: 3.

7. The recombinant gene expression cassette of claim 4, wherein the C-terminal domain contributing to stabilization of a LysR protein dimer comprises an amino acid sequence represented by SEQ ID NO: 4.

8. The recombinant gene expression cassette of claim 1, wherein the binding site to a LysR protein comprises a base sequence selected from SEQ ID NOs: 44 or 45.

9. A recombinant expression vector comprising the recombinant gene expression cassette of claim 1.

10. A recombinant microorganism transformed with the recombinant expression vector of claim 9.

11. A recombinant microorganism comprising the recombinant gene expression cassette of claim 1 inserted to a chromosome of a host cell.

12. A method of producing a target expression protein, the method comprising:
    culturing the recombinant microorganism of claim 10.

13. The method of claim 12, wherein the culturing of the recombinant microorganism further comprises adding for 3-hydroxypropionic acid (3-HP) to the culture.

* * * * *

SEQUENCE LISTING

```
<160> NUMBER OF SEQ ID NOS: 266

<210> SEQ ID NO 1
<211> LENGTH: 17
<212> TYPE: PRT
<213> ORGANISM: Artificial Sequence
<220> FEATURE:
<223> OTHER INFORMATION: LysR Helix-turn-Helix
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid
```

```
<400> SEQUENCE: 1

Thr Xaa Xaa Arg Xaa Xaa Xaa Xaa Glu Xaa Xaa Xaa Xaa Xaa Xaa
1               5                   10                  15

Leu

<210> SEQ ID NO 2
<211> LENGTH: 60
<212> TYPE: PRT
<213> ORGANISM: Artificial Sequence
<220> FEATURE:
<223> OTHER INFORMATION: LysR Helix-turn-Helix
<220> FEATURE:
<221> NAME/KEY: misc_feature
<222> LOCATION: (2)..(28)
<223> OTHER INFORMATION: Xaa can be any naturally occurring amino acid
<220> FEATURE:
<221> NAME/KEY: misc_feature
<222> LOCATION: (30)..(37)
<223> OTHER INFORMATION: Xaa can be any naturally occurring amino acid
<220> FEATURE:
<221> NAME/KEY: misc_feature
<222> LOCATION: (39)..(44)
<223> OTHER INFORMATION: Xaa can be any naturally occurring amino acid
<220> FEATURE:
<221> NAME/KEY: misc_feature
<222> LOCATION: (46)..(59)
<223> OTHER INFORMATION: Xaa can be any naturally occurring amino acid

<400> SEQUENCE: 2

Trp Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Thr Xaa Xaa
                20                  25                  30

Xaa Xaa Xaa Xaa Xaa Glu Xaa Xaa Xaa Xaa Xaa Leu Xaa Xaa Xaa
            35                  40                  45

Xaa Xaa Xaa Xaa Xaa Xaa Xaa Xaa Xaa Xaa Xaa Gly
        50                  55                  60

<210> SEQ ID NO 3
<211> LENGTH: 81
<212> TYPE: PRT
<213> ORGANISM: Artificial Sequence
<220> FEATURE:
<223> OTHER INFORMATION: substrate binding domain
<220> FEATURE:
<221> NAME/KEY: misc_feature
<222> LOCATION: (3)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 3

Asp Thr Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Pro Xaa
65                  70                  75                  80

Phe
```

-continued

```
<210> SEQ ID NO 4
<211> LENGTH: 78
<212> TYPE: PRT
<213> ORGANISM: Artificial Sequence
<220> FEATURE:
<223> OTHER INFORMATION: substrate binding domain
<220> FEATURE:
<221> NAME/KEY: misc_feature
<222> LOCATION: (2)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(58)
<223> OTHER INFORMATION: Xaa can be any naturally occurring amino acid
<220> FEATURE:
<221> NAME/KEY: misc_feature
<222> LOCATION: (60)..(77)
<223> OTHER INFORMATION: Xaa can be any naturally occurring amino acid

<400> SEQUENCE: 4

Ala Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Gly
            20                  25                  30

Xaa Xaa Arg Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Pro Xaa Xaa Xaa Xaa Xaa
    50                  55                  60

Xaa Xaa Xaa Xaa Xaa Xaa Xaa Xaa Xaa Xaa Xaa Xaa Xaa Glu
65                  70                  75

<210> SEQ ID NO 5
<211> LENGTH: 9
<212> TYPE: DNA
<213> ORGANISM: Achromobacter
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 5 cananatnn                                                            9

<210> SEQ ID NO 6
<211> LENGTH: 9
<212> TYPE: DNA
<213> ORGANISM: Acidovorax
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
```

```
<222> LOCATION: (8)..(8)
<223> OTHER INFORMATION: n is a, c, g, or t

<400> SEQUENCE: 6 tngcananc                                                                  9

<210> SEQ ID NO 7
<211> LENGTH: 9
<212> TYPE: DNA
<213> ORGANISM: Acinetobacter
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 7 gtnnangat                                                                  9

<210> SEQ ID NO 8
<211> LENGTH: 9
<212> TYPE: DNA
<213> ORGANISM: Advenella
<220> FEATURE:
<221> NAME/KEY: misc_feature
<222> LOCATION: (6)..(6)
<223> OTHER INFORMATION: n is a, c, g, or t

<400> SEQUENCE: 8 ttgcanatt                                                                  9

<210> SEQ ID NO 9
<211> LENGTH: 9
<212> TYPE: DNA
<213> ORGANISM: Aeromonas
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 9 gggnannca                                                                  9

<210> SEQ ID NO 10
<211> LENGTH: 9
<212> TYPE: DNA
<213> ORGANISM: Alcaligenes
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 10 cananatnn                                                                  9
```

```
<210> SEQ ID NO 11
<211> LENGTH: 9
<212> TYPE: DNA
<213> ORGANISM: Alcanivorax
<220> FEATURE:
<221> NAME/KEY: misc_feature
<222> LOCATION: (2)..(2)
<223> OTHER INFORMATION: n is a, c, g, or t

<400> SEQUENCE: 11 ancagcatg                                                                 9

<210> SEQ ID NO 12
<211> LENGTH: 9
<212> TYPE: DNA
<213> ORGANISM: Alicycliphilus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 12 tgcnaagnn                                                                 9

<210> SEQ ID NO 13
<211> LENGTH: 9
<212> TYPE: DNA
<213> ORGANISM: Anaeromyxobacter
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 13 gggncgnng                                                                 9

<210> SEQ ID NO 14
<211> LENGTH: 9
<212> TYPE: DNA
<213> ORGANISM: Azospirillum
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 14 ntgccngcg                                                                 9

<210> SEQ ID NO 15
<211> LENGTH: 9
<212> TYPE: DNA
<213> ORGANISM: Azotobacter
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
```

<222> LOCATION: (3)..(5)
<223> OTHER INFORMATION: n is a, c, g, or t

<400> SEQUENCE: 15 ntnnngagc                                                                         9

<210> SEQ ID NO 16
<211> LENGTH: 9
<212> TYPE: DNA
<213> ORGANISM: Beijerinckia
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 16 attnncntg                                                                         9

<210> SEQ ID NO 17
<211> LENGTH: 9
<212> TYPE: DNA
<213> ORGANISM: Bordetella
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 17 nttncgtng                                                                         9

<210> SEQ ID NO 18
<211> LENGTH: 9
<212> TYPE: DNA
<213> ORGANISM: Bradyrhizobium
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 18 anatatnng                                                                         9

<210> SEQ ID NO 19
<211> LENGTH: 9
<212> TYPE: DNA
<213> ORGANISM: Brucella
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:

```
<221> NAME/KEY: misc_feature
<222> LOCATION: (9)..(9)
<223> OTHER INFORMATION: n is a, c, g, or t

<400> SEQUENCE: 19 annaangcn                                                                 9

<210> SEQ ID NO 20
<211> LENGTH: 9
<212> TYPE: DNA
<213> ORGANISM: Burkholderia
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 20 gccnacnnt                                                                 9

<210> SEQ ID NO 21
<211> LENGTH: 9
<212> TYPE: DNA
<213> ORGANISM: Corynebacterium
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 21 cacctntnc                                                                 9

<210> SEQ ID NO 22
<211> LENGTH: 9
<212> TYPE: DNA
<213> ORGANISM: Cupriavidus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 22 agtncanng                                                                 9

<210> SEQ ID NO 23
<211> LENGTH: 9
<212> TYPE: DNA
<213> ORGANISM: Delftia
<220> FEATURE:
<221> NAME/KEY: misc_feature
<222> LOCATION: (8)..(9)
<223> OTHER INFORMATION: n is a, c, g, or t

<400> SEQUENCE: 23 gcaaaaann                                                                 9

<210> SEQ ID NO 24
<211> LENGTH: 9
```

```
<212> TYPE: DNA
<213> ORGANISM: Ferrimonas
<220> FEATURE:
<221> NAME/KEY: misc_feature
<222> LOCATION: (9)..(9)
<223> OTHER INFORMATION: n is a, c, g, or t

<400> SEQUENCE: 24 gcggttttn                                                                9

<210> SEQ ID NO 25
<211> LENGTH: 9
<212> TYPE: DNA
<213> ORGANISM: Glaciecola
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 25 tnantngac                                                                9

<210> SEQ ID NO 26
<211> LENGTH: 9
<212> TYPE: DNA
<213> ORGANISM: Gordonia
<220> FEATURE:
<221> NAME/KEY: misc_feature
<222> LOCATION: (3)..(4)
<223> OTHER INFORMATION: n is a, c, g, or t

<400> SEQUENCE: 26 gannccggc                                                                9

<210> SEQ ID NO 27
<211> LENGTH: 9
<212> TYPE: DNA
<213> ORGANISM: Halomonas
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 27 nacacnnaa                                                                9

<210> SEQ ID NO 28
<211> LENGTH: 9
<212> TYPE: DNA
<213> ORGANISM: Janthinobacterium
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
```

```
<221> NAME/KEY: misc_feature
<222> LOCATION: (9)..(9)
<223> OTHER INFORMATION: n is a, c, g, or t

<400> SEQUENCE: 28 tncgnattn                                                                         9

<210> SEQ ID NO 29
<211> LENGTH: 9
<212> TYPE: DNA
<213> ORGANISM: Marinobacter
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 29 cannangnt                                                                         9

<210> SEQ ID NO 30
<211> LENGTH: 9
<212> TYPE: DNA
<213> ORGANISM: Methylocystis
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 30 cgancnacc                                                                         9

<210> SEQ ID NO 31
<211> LENGTH: 9
<212> TYPE: DNA
<213> ORGANISM: Phenylobaculum
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 31 gtnccgcnc                                                                         9

<210> SEQ ID NO 32
<211> LENGTH: 9
<212> TYPE: DNA
<213> ORGANISM: Pseudomonas
<220> FEATURE:
<221> NAME/KEY: misc_feature
<222> LOCATION: (6)..(8)
<223> OTHER INFORMATION: n is a, c, g, or t

<400> SEQUENCE: 32 ttgcannnc                                                                         9
```

<210> SEQ ID NO 33
<211> LENGTH: 9
<212> TYPE: DNA
<213> ORGANISM: Ralstonia
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 33 gccnacnnt                                                                        9

<210> SEQ ID NO 34
<211> LENGTH: 9
<212> TYPE: DNA
<213> ORGANISM: Shewanella
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 34 nttngnnta                                                                        9

<210> SEQ ID NO 35
<211> LENGTH: 9
<212> TYPE: DNA
<213> ORGANISM: Sinorhizobium
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 35 tngnaantt                                                                        9

<210> SEQ ID NO 36
<211> LENGTH: 9
<212> TYPE: DNA
<213> ORGANISM: Sphingobium
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)

```
<223> OTHER INFORMATION: n is a, c, g, or t

<400> SEQUENCE: 36 cnnacnanc                                                                        9

<210> SEQ ID NO 37
<211> LENGTH: 9
<212> TYPE: DNA
<213> ORGANISM: Stenotrophomonas
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 37 gnncngatt                                                                        9

<210> SEQ ID NO 38
<211> LENGTH: 9
<212> TYPE: DNA
<213> ORGANISM: Tistrella
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 38 ccggnngng                                                                        9

<210> SEQ ID NO 39
<211> LENGTH: 9
<212> TYPE: DNA
<213> ORGANISM: Variovorax
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 39 ntntattnt                                                                        9

<210> SEQ ID NO 40
<211> LENGTH: 9
<212> TYPE: DNA
<213> ORGANISM: Verminephrobacter
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t

<400> SEQUENCE: 40
``` cntgnncga                                                        9

<210> SEQ ID NO 41
<211> LENGTH: 9
<212> TYPE: DNA
<213> ORGANISM: Vibrio
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 41 tgnncnntt                                                        9

<210> SEQ ID NO 42
<211> LENGTH: 9
<212> TYPE: DNA
<213> ORGANISM: Xanthobacter
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 42 ctnngcacn                                                        9

<210> SEQ ID NO 43
<211> LENGTH: 9
<212> TYPE: DNA
<213> ORGANISM: Xanthomonas
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 43 gnngtggnc                                                        9

<210> SEQ ID NO 44
<211> LENGTH: 50
<212> TYPE: DNA
<213> ORGANISM: Pseudomonas denitrificans

<400> SEQUENCE: 44
cagcaaggat gctggcccgg gcctgggcgg agacgtcttt cgcgcccgac           50

<210> SEQ ID NO 45
<211> LENGTH: 50
<212> TYPE: DNA
<213> ORGANISM: Pseudomonas denitrificans

<400> SEQUENCE: 45
aaacgttcgt attttatcg cgaacgaacg actaggctcc atcgtcatac            50

<210> SEQ ID NO 46

```
<211> LENGTH: 136
<212> TYPE: DNA
<213> ORGANISM: Pseudomonas denitrificans

<400> SEQUENCE: 46
catgtcagcc tcagcgcacc tcgaatgtgc aaaaacgcag accatacttg cacatcaccg    60
cattgagtac atcaaaaatg cactgttagg atcgatccag acaacaaaaa agccacaggc   120
tgggagaatc ccgatg                                                   136

<210> SEQ ID NO 47
<211> LENGTH: 136
<212> TYPE: DNA
<213> ORGANISM: Pseudomonas denitrificans

<400> SEQUENCE: 47
gtacagtcgg agtcgcgtgg agcttacacg tttttgcgtc tggtatgaac gtgtagtggc    60
gtaactcatg tagtttttac gtgacaatcc tagctaggtc tgttgttttt tcggtgtccg   120
accctcttag ggctac                                                   136

<210> SEQ ID NO 48
<211> LENGTH: 130
<212> TYPE: DNA
<213> ORGANISM: Pseudomonas denitrificans

<400> SEQUENCE: 48
catcgtggcg actctcattg ttagaaaacg cacagcaggt gactttaaac gttcgtattt    60
ttatcgcgaa cgaacgacta ggctccatcg tcatacccaa agaacaagaa cgacgaggg   120 actttccatg                                                          130

<210> SEQ ID NO 49
<211> LENGTH: 130
<212> TYPE: DNA
<213> ORGANISM: Pseudomonas denitrificans

<400> SEQUENCE: 49
gtagcaccgc tgagagtaac aatcttttgc gtgtcgtcca ctgaaatttg caagcataaa    60
aatagcgctt gcttgctgat ccgaggtagc agtatgggtt ttcttgttct tgctgctccc   120
tgaaaggtac                                                          130

<210> SEQ ID NO 50
<211> LENGTH: 136
<212> TYPE: DNA
<213> ORGANISM: Pseudomonas denitrificans

<400> SEQUENCE: 50
catgtcagcc tcagcgcacc tcgaatgtgc aaaaacgcag accatacttg cacatcaccg    60
cattgagtac atcaaaaatg cactgttagg atcgatccag acaacaaaaa agccacaggc   120
tgggagaatc ccgatg                                                   136

<210> SEQ ID NO 51
<211> LENGTH: 136
<212> TYPE: DNA
<213> ORGANISM: Pseudomonas denitrificans

<400> SEQUENCE: 51
gtacagtcgg agtcgcgtgg agcttacacg tttttgcgtc tggtatgaac gtgtagtggc    60
gtaactcatg tagtttttac gtgacaatcc tagctaggtc tgttgttttt tcggtgtccg   120
```
accctcttag ggctac    136

<210> SEQ ID NO 52
<211> LENGTH: 9
<212> TYPE: DNA
<213> ORGANISM: Pseudomonas denitrificans

<400> SEQUENCE: 52 aacgtgtaa    9

<210> SEQ ID NO 53
<211> LENGTH: 9
<212> TYPE: DNA
<213> ORGANISM: Pseudomonas denitrificans

<400> SEQUENCE: 53 aacgtgtag    9

<210> SEQ ID NO 54
<211> LENGTH: 9
<212> TYPE: DNA
<213> ORGANISM: Pseudomonas denitrificans

<400> SEQUENCE: 54 cacgtaaaa    9

<210> SEQ ID NO 55
<211> LENGTH: 9
<212> TYPE: DNA
<213> ORGANISM: Pseudomonas denitrificans

<400> SEQUENCE: 55 taggtctgt    9

<210> SEQ ID NO 56
<211> LENGTH: 9
<212> TYPE: DNA
<213> ORGANISM: Pseudomonas denitrificans

<400> SEQUENCE: 56 aacgtgtaa    9

<210> SEQ ID NO 57
<211> LENGTH: 130
<212> TYPE: DNA
<213> ORGANISM: Pseudomonas denitrificans

<400> SEQUENCE: 57
gtcagcctca gcgcacctcg aatgtgcaaa aacgcagacc atacttgcac atcaccgcat    60
tgagtacatc aaaaatgcac tgttaggatc gatccagaca acaaaaaagc cacaggctgg    120
gagaatcccg    130

<210> SEQ ID NO 58
<211> LENGTH: 130
<212> TYPE: DNA
<213> ORGANISM: Pseudomonas denitrificans

<400> SEQUENCE: 58
cagtcggagt cgcgtggagc ttacacgttt ttgcgtctgg tatgaacgtg tagtggcgta    60
actcatgtag tttttacgtg acaatcctag ctaggtctgt tgttttttcg gtgtccgacc    120
ctcttagggc                                                            130

<210> SEQ ID NO 59
<211> LENGTH: 63
<212> TYPE: PRT
<213> ORGANISM: Achromobacter arsenitoxydans

<400> SEQUENCE: 59

Met Leu Asp Trp Asp Ser Leu Arg Tyr Phe Leu Glu Val Ala Arg Thr
1               5                   10                  15

Gln Arg Val Ser Ala Ala Ala Arg Lys Leu Gly Val Glu His Thr Thr
            20                  25                  30

Val Ser Arg Arg Ile Arg Ala Leu Glu Thr Glu Leu Asp Thr Leu Leu
        35                  40                  45

Phe Glu Lys Ser Arg Ser Ala Gly Phe Val Leu Thr Asp Asp Gly
    50                  55                  60

<210> SEQ ID NO 60
<211> LENGTH: 63
<212> TYPE: PRT
<213> ORGANISM: Achromobacter_piechaudii

<400> SEQUENCE: 60

Met Leu Asp Trp Asp Ser Leu Arg Tyr Phe Leu Glu Val Ala Arg Thr
1               5                   10                  15

Gln Arg Val Ser Ala Ala Ala Arg Lys Leu Gly Val Glu His Thr Thr
            20                  25                  30

Val Ser Arg Arg Ile Arg Ala Leu Glu Thr Glu Leu Asp Thr Leu Leu
        35                  40                  45

Phe Glu Lys Ser Arg Ser Ala Gly Phe Val Leu Thr Asp Asp Gly
    50                  55                  60

<210> SEQ ID NO 61
<211> LENGTH: 63
<212> TYPE: PRT
<213> ORGANISM: Achromobacter xylosoxidans

<400> SEQUENCE: 61

Met Leu Asp Trp Asp Ser Leu Arg Tyr Phe Leu Glu Val Ala Arg Thr
1               5                   10                  15

Gln Arg Val Ser Ala Ala Ala Arg Arg Leu Gly Val Glu His Thr Thr
            20                  25                  30

Val Ser Arg Arg Ile Arg Ala Leu Glu Thr Glu Leu Asp Thr Leu Leu
        35                  40                  45

Phe Glu Lys Ser Arg Ser Ala Gly Phe Val Leu Thr Glu Asp Gly
    50                  55                  60

<210> SEQ ID NO 62
<211> LENGTH: 63
<212> TYPE: PRT
<213> ORGANISM: Acidovorax avenae

<400> SEQUENCE: 62

Met Asp Trp Glu Asn Leu Arg Tyr Phe Leu Glu Leu Ala Arg Thr Gly
1               5                   10                  15

Thr Leu Ala Ala Ala Ala Arg Arg Thr Gly Val Glu His Thr Thr Val
            20                  25                  30

Ala Arg Arg Ile Gln Ala Leu Glu Lys Gln Met Gly Glu Ser Leu Phe
        35                  40                  45

Ala Arg Glu Ala Gly Gly His Arg Leu Thr Glu Ala Gly Arg His
    50                  55                  60

<210> SEQ ID NO 63
<211> LENGTH: 63
<212> TYPE: PRT
<213> ORGANISM: Acidovorax citrulli

<400> SEQUENCE: 63

Met Asp Trp Glu Asn Leu Arg Tyr Phe Leu Glu Leu Ala Arg Thr Gly
1               5                   10                  15

Thr Leu Ala Ala Ala Ala Arg Arg Thr Gly Val Glu His Thr Thr Val
            20                  25                  30

Ala Arg Arg Ile Gln Ala Leu Glu Lys Gln Met Gly Glu Ser Leu Phe
        35                  40                  45

Ala Arg Glu Ala Gly Gly His Arg Leu Thr Glu Ala Gly Arg His
    50                  55                  60

<210> SEQ ID NO 64
<211> LENGTH: 63
<212> TYPE: PRT
<213> ORGANISM: Acidovorax delafieldii

<400> SEQUENCE: 64

Met Asp Trp Asp Asn Leu Arg Tyr Phe Leu Glu Leu Ala Arg Ala Gly
1               5                   10                  15

Thr Leu Val Gly Ala Ala Arg Arg Leu Ala Val Asp His Thr Thr Val
            20                  25                  30

Ala Arg Arg Ile Gln Ala Leu Glu Lys Gln Val Gly Ser Ala Leu Phe
        35                  40                  45

Ala Arg Glu Ala Gly Gly His Arg Leu Thr Glu Ala Gly Arg Val
    50                  55                  60

<210> SEQ ID NO 65
<211> LENGTH: 63
<212> TYPE: PRT
<213> ORGANISM: Acidovorax ebreus

<400> SEQUENCE: 65

Met Asp Trp Asp Asn Leu Arg Tyr Phe Leu Glu Leu Ala Arg Thr Gly
1               5                   10                  15

Thr Leu Ala Gly Ala Ala Arg Arg Thr Gly Val Glu His Thr Thr Val
            20                  25                  30

Ala Arg Arg Ile Gln Ala Leu Glu Lys Gln Met Gly Ala Pro Leu Phe
        35                  40                  45

Ala Arg Glu Ala Ala Gly His Arg Leu Thr Glu Thr Gly Arg His
    50                  55                  60

<210> SEQ ID NO 66
<211> LENGTH: 63
<212> TYPE: PRT
<213> ORGANISM: Acidovorax radicis

<400> SEQUENCE: 66

Met Asp Trp Asp His Phe Arg Tyr Phe Leu Glu Leu Ala Arg Ala Gly
1               5                   10                  15

Thr Leu Val Gly Ala Ala Arg Arg Leu Gly Val Glu His Thr Thr Val
            20                  25                  30

Ser Arg Arg Leu Gln Ala Leu Glu Lys Gln Val Gly Ser Ala Leu Phe
        35                  40                  45

```
Ala Arg Asp Ala Gly Gly His Arg Leu Thr Glu Ala Gly Arg Gln
        50                  55                  60

<210> SEQ ID NO 67
<211> LENGTH: 63
<212> TYPE: PRT
<213> ORGANISM: Acidovorax sp.

<400> SEQUENCE: 67

Met Asp Trp Asp Asn Leu Arg Tyr Phe Leu Glu Leu Ala Arg Ala Gly
1               5                   10                  15

Thr Leu Val Gly Ala Ala Arg Arg Leu Ala Val Asp His Thr Thr Val
            20                  25                  30

Ala Arg Arg Leu Gln Ala Leu Glu Lys Gln Val Gly Ser Ala Leu Phe
        35                  40                  45

Ala Arg Glu Ala Gly Gly His Arg Leu Thr Glu Ala Gly Arg Ala
    50                  55                  60

<210> SEQ ID NO 68
<211> LENGTH: 63
<212> TYPE: PRT
<213> ORGANISM: Acinetobacter

<400> SEQUENCE: 68

Met Lys Val Asp Trp Asp His Leu Arg Phe Phe Leu Val Leu Ala Arg
1               5                   10                  15

Ala Lys Thr Leu Thr Asn Ala Ala Arg Leu Ile Gly Val Glu His Ser
            20                  25                  30

Thr Val Ala Arg Arg Ile Gln Ala Leu Glu Ser Thr Leu Gly Thr Gln
        35                  40                  45

Leu Phe Lys Arg Glu Ala Thr Gly Tyr Glu Leu Thr Ser Glu Gly
    50                  55                  60

<210> SEQ ID NO 69
<211> LENGTH: 63
<212> TYPE: PRT
<213> ORGANISM: Acinetobacter beijerinckii

<400> SEQUENCE: 69

Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Leu Ala Leu Gly Thr Thr
        35                  40                  45

Leu Phe Lys Arg Glu Ala Ser Gly Tyr Glu Leu Thr Met Glu Gly
    50                  55                  60

<210> SEQ ID NO 70
<211> LENGTH: 63
<212> TYPE: PRT
<213> ORGANISM: Acinetobacter bohemicus

<400> SEQUENCE: 70

Met Lys Val Asp Trp Asp His Leu Arg Phe Phe Leu Val Leu Ala Arg
1               5                   10                  15

Ala Lys Thr Leu Thr Asn Ala Ala Arg Leu Ile Gly Val Glu His Ser
            20                  25                  30

Thr Val Ala Arg Arg Ile Gln Ala Leu Glu Gln Asn Leu Gly Thr Gln
```

```
                35                  40                  45

Leu Phe Lys Arg Glu Ala Thr Gly Tyr Glu Leu Thr Ala Glu Gly
 50                  55                  60

<210> SEQ ID NO 71
<211> LENGTH: 63
<212> TYPE: PRT
<213> ORGANISM: Acinetobacter calcoaceticus

<400> SEQUENCE: 71

Met Thr Thr Lys Met Lys Val Asp Trp Asp His Leu His Phe Phe Leu
 1               5                  10                  15

Val Leu Ala Arg Thr Lys Thr Leu Thr Asn Ala Ala Arg Ile Ile Gly
             20                  25                  30

Val Glu His Ser Thr Val Ala Arg Arg Ile Gln Ala Leu Glu Leu Ala
         35                  40                  45

Leu Gly Thr Thr Leu Phe Lys Arg Glu Ala Thr Gly Tyr Glu Leu
 50                  55                  60

<210> SEQ ID NO 72
<211> LENGTH: 63
<212> TYPE: PRT
<213> ORGANISM: Acinetobacter gerneri

<400> SEQUENCE: 72

Met Lys Val Asp Trp Asp His Leu Gln Phe Phe Leu Val Leu Ala Arg
 1               5                  10                  15

Ala Lys Thr Leu Thr Asn Ala Ala Arg Ile Ile Gly Val Glu His Ser
             20                  25                  30

Thr Val Ala Arg Arg Ile Gln Ala Leu Glu Leu Ala Leu Gly Thr Pro
         35                  40                  45

Leu Phe Lys Arg Glu Ala Ser Gly Tyr Glu Leu Thr Leu Glu Gly
 50                  55                  60

<210> SEQ ID NO 73
<211> LENGTH: 63
<212> TYPE: PRT
<213> ORGANISM: Acinetobacter gyllenbergii

<400> SEQUENCE: 73

Met Lys Val Asp Trp Asp His Leu Gln Phe Phe Leu Val Leu Ala Arg
 1               5                  10                  15

Thr Lys Thr Leu Thr Asn Ala Ala Arg Ile Ile Gly Val Glu His Ser
             20                  25                  30

Thr Val Ala Arg Arg Ile Gln Ala Leu Glu Gln Ala Leu Gly Val Thr
         35                  40                  45

Leu Phe Lys Arg Glu Ala Ser Gly Tyr Glu Leu Thr Leu Glu Gly
 50                  55                  60

<210> SEQ ID NO 74
<211> LENGTH: 63
<212> TYPE: PRT
<213> ORGANISM: Acinetobacter johnsonii

<400> SEQUENCE: 74

Met Lys Val Asp Trp Asp His Leu Gln Phe Phe Leu Val Leu Ala Arg
 1               5                  10                  15

Ala Lys Thr Leu Thr Asn Ala Ala Arg Ile Ile Gly Val Glu His Ser
             20                  25                  30
```

```
Thr Val Ala Arg Arg Val Gln Ser Leu Glu Val Ala Leu Gly Thr Pro
            35                  40                  45

Leu Phe Lys Arg Glu Ala Thr Gly Tyr Glu Leu Thr Val Asp Gly
        50                  55                  60
```

<210> SEQ ID NO 75
<211> LENGTH: 63
<212> TYPE: PRT
<213> ORGANISM: Acinetobacter junii

<400> SEQUENCE: 75

```
Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Leu Ala Leu Gly Thr Thr
            35                  40                  45

Leu Phe Lys Arg Glu Ala Ser Gly Tyr Glu Leu Thr Met Glu Gly
        50                  55                  60
```

<210> SEQ ID NO 76
<211> LENGTH: 63
<212> TYPE: PRT
<213> ORGANISM: Acinetobacter nosocomialis

<400> SEQUENCE: 76

```
Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Leu Ala Leu Gly Thr Thr
            35                  40                  45

Leu Phe Lys Arg Glu Ala Thr Gly Tyr Glu Leu Thr Leu Glu Gly
        50                  55                  60
```

<210> SEQ ID NO 77
<211> LENGTH: 63
<212> TYPE: PRT
<213> ORGANISM: Acinetobacter rudis

<400> SEQUENCE: 77

```
Met Ser Met Asp Trp Asn His Leu Arg Phe Phe Leu Val Leu Ala Arg
1               5                   10                  15

Ala Lys Thr Leu Thr Asn Ala Ala Arg Leu Ile Gly Val Glu His Ser
            20                  25                  30

Thr Val Ala Arg Arg Ile Gln Ala Leu Glu Gln Ser Leu Gly Thr Gln
            35                  40                  45

Leu Phe Lys Arg Glu Ala Thr Gly Tyr Glu Leu Thr Ile Glu Gly
        50                  55                  60
```

<210> SEQ ID NO 78
<211> LENGTH: 63
<212> TYPE: PRT
<213> ORGANISM: Acinetobacter tandoii

<400> SEQUENCE: 78

```
Met Lys Val Asp Trp Asp His Leu Gln Phe Phe Leu Val Leu Ala Arg
1               5                   10                  15

Ala Lys Thr Leu Thr Asn Ala Ala Arg Ile Ile Gly Val Glu His Ser
            20                  25                  30
```

```
Thr Val Ala Arg Arg Ile Gln Ser Leu Glu Val Ala Leu Gly Thr Pro
            35                  40                  45

Leu Phe Lys Arg Glu Ala Thr Gly Tyr Glu Leu Thr Val Asp Gly
 50                  55                  60
```

<210> SEQ ID NO 79
<211> LENGTH: 63
<212> TYPE: PRT
<213> ORGANISM: Advenella kashmirensis

<400> SEQUENCE: 79

```
Met Asp Trp Asp Asn Leu Arg Phe Phe Leu Glu Ile Ala Arg Thr Gly
 1               5                   10                  15

Arg Leu Ala Ser Ala Ala His Arg Leu Gly Val Asp Gln Ala Thr Val
            20                  25                  30

Ser Arg Arg Met Thr Ala Leu Glu Thr Gln Leu Gly Arg Arg Leu Phe
        35                  40                  45

Val Arg Ser Thr Thr Gly Met Ser Leu Thr Asp Ala Gly Arg Gln
 50                  55                  60
```

<210> SEQ ID NO 80
<211> LENGTH: 63
<212> TYPE: PRT
<213> ORGANISM: Alcaligenes faecalis

<400> SEQUENCE: 80

```
Met Asp Trp Asp Asn Leu Arg Tyr Phe Leu Glu Val Ala Arg Cys Gln
 1               5                   10                  15

Arg Ile Ser Val Ala Ala Gln Arg Leu Gly Val Gln His Ser Thr Val
            20                  25                  30

Ala Arg Arg Ile Gln Ala Leu Glu Gln Glu Leu Gly Leu Arg Leu Phe
        35                  40                  45

His Lys Ser Thr Val Ser Gly Tyr Ser Leu Thr Ser Glu Gly Gln
 50                  55                  60
```

<210> SEQ ID NO 81
<211> LENGTH: 63
<212> TYPE: PRT
<213> ORGANISM: Alicycliphilus denitrificans

<400> SEQUENCE: 81

```
Met Asp Trp Asp Asn Leu Arg Tyr Phe Leu Glu Leu Ala Arg Thr Gly
 1               5                   10                  15

Thr Leu Ala Ala Ala Arg Arg Thr Gly Val Glu His Thr Thr Val
            20                  25                  30

Ala Arg Arg Ile Gln Ala Leu Glu Lys Gln Met Gly Ala Pro Leu Phe
        35                  40                  45

Ala Arg Glu Ala Ala Gly His Arg Leu Thr Glu Ala Gly Arg His
 50                  55                  60
```

<210> SEQ ID NO 82
<211> LENGTH: 63
<212> TYPE: PRT
<213> ORGANISM: Azospirillum lipoferum

<400> SEQUENCE: 82

```
Met Ala Asp Phe Asn Trp Asn Asp Leu Arg Phe Phe Leu Ala Val Ala
 1               5                   10                  15

Arg Ala Gly Thr Leu Thr Thr Ala Ala Gln Arg Leu Arg Ala Asp His
```

```
                    20                  25                  30

Ser Thr Val Ser Arg Arg Ile Thr Ala Leu Glu Asp Ala Leu Arg Val
                35                  40                  45

Thr Leu Phe Glu Arg Arg Pro Ser Gly Phe Thr Leu Thr Pro Gln
    50                  55                  60
```

<210> SEQ ID NO 83
<211> LENGTH: 63
<212> TYPE: PRT
<213> ORGANISM: Azotobacter chroococcum

<400> SEQUENCE: 83

```
Met Asp Trp Asp Asn Leu Arg Phe Phe Leu Glu Leu Ser Arg Ala Lys
1               5                   10                  15

Lys Leu Thr Val Ala Ala Arg Arg Leu Gly Val Asp His Thr Thr Val
                20                  25                  30

Ala Arg Arg Val Gln Ala Leu Glu Lys Ser Leu Gly Gln Pro Leu Phe
                35                  40                  45

Ile Arg Ser Gly Ser Gly Tyr Ala Pro Thr Glu Ala Gly Arg Arg
    50                  55                  60
```

<210> SEQ ID NO 84
<211> LENGTH: 63
<212> TYPE: PRT
<213> ORGANISM: Azotobacter vinelandii

<400> SEQUENCE: 84

```
Met Asp Trp Asp Asn Leu Arg Phe Phe Leu Glu Leu Ala Arg Ala Lys
1               5                   10                  15

Lys Leu Thr Val Ala Ala Arg Arg Leu Gly Val Asp His Thr Thr Val
                20                  25                  30

Ala Arg Arg Val Gln Ala Leu Glu Lys Ser Leu Gly Gln Pro Leu Phe
                35                  40                  45

Ile Arg Gly Ser Ser Gly Tyr Gly Pro Thr Glu Ala Gly Arg Arg
    50                  55                  60
```

<210> SEQ ID NO 85
<211> LENGTH: 63
<212> TYPE: PRT
<213> ORGANISM: Beijerinckia indica

<400> SEQUENCE: 85

```
Met Ser Asp Phe Asp Trp Asn Ser Leu Arg Ser Phe Leu Ala Val Ala
1               5                   10                  15

Arg Thr Gly Arg Leu Thr Thr Ala Ala Arg Thr Leu Gly Val Asp His
                20                  25                  30

Thr Thr Leu Ser Arg Arg Ile Ala Gly Leu Glu Glu Ala Leu Lys Val
                35                  40                  45

Lys Leu Phe Glu Arg His Pro Ser Gly Tyr Arg Leu Thr Asn Ala
    50                  55                  60
```

<210> SEQ ID NO 86
<211> LENGTH: 63
<212> TYPE: PRT
<213> ORGANISM: Beijerinckia mobilis

<400> SEQUENCE: 86

```
Met Ser Asp Phe Asp Trp Asn His Leu Arg Ser Phe Leu Thr Val Ala
1               5                   10                  15
```

Arg Thr Gly Arg Leu Thr Ile Ser Ala Arg Lys Leu Gly Ile Asp His
                20                  25                  30

Thr Thr Leu Gly Arg Arg Ile Ala Gly Leu Glu Glu Ala Leu Lys Val
            35                  40                  45

Gln Leu Phe Glu Arg His Pro Thr Gly Tyr Arg Leu Thr Asn Ala
    50                  55                  60

<210> SEQ ID NO 87
<211> LENGTH: 63
<212> TYPE: PRT
<213> ORGANISM: Bordetella avium

<400> SEQUENCE: 87

Met Leu Asp Trp Asp Ser Leu Arg Tyr Phe Leu Glu Val Ala Arg Ser
1               5                   10                  15

Gln Arg Val Ser Ala Ala Ala Arg Thr Leu Gly Val Glu His Thr Thr
                20                  25                  30

Val Ala Arg Arg Ile Arg Ala Leu Glu Ala Glu Leu Gly Ser Leu Leu
            35                  40                  45

Phe Glu Lys Ser Arg Ser Ala Gly Phe Val Leu Thr Glu Asp Gly
    50                  55                  60

<210> SEQ ID NO 88
<211> LENGTH: 63
<212> TYPE: PRT
<213> ORGANISM: Bordetella bronchiseptica

<400> SEQUENCE: 88

Met Leu Asp Trp Asp Ser Leu Arg Tyr Phe Leu Glu Val Ala Arg Thr
1               5                   10                  15

Gln Arg Val Ser Ala Ala Ala Arg Lys Leu Gly Val Glu His Thr Thr
                20                  25                  30

Val Ala Arg Arg Val Arg Ala Leu Glu Ala Glu Leu Asp Ser Leu Leu
            35                  40                  45

Phe Glu Lys Ser Arg Ser Ala Gly Tyr Val Leu Thr Glu Asp Gly
    50                  55                  60

<210> SEQ ID NO 89
<211> LENGTH: 63
<212> TYPE: PRT
<213> ORGANISM: Bordetella hinzii

<400> SEQUENCE: 89

Met Leu Asp Trp Asp Ser Leu Arg Tyr Phe Leu Glu Val Ala Arg Ser
1               5                   10                  15

Gln Arg Val Ser Ala Ala Ala Arg Thr Leu Gly Val Glu His Thr Thr
                20                  25                  30

Val Ala Arg Arg Ile Arg Ala Leu Glu Ala Glu Leu Gly Ser Leu Leu
            35                  40                  45

Phe Glu Lys Ser Arg Ser Ala Gly Phe Val Leu Thr Glu Asp Gly
    50                  55                  60

<210> SEQ ID NO 90
<211> LENGTH: 63
<212> TYPE: PRT
<213> ORGANISM: Bordetella petrii

<400> SEQUENCE: 90

Met Leu Asp Trp Asp Gly Leu Arg Tyr Phe Leu Glu Val Ala Arg Thr
1               5                   10                  15

Gln Arg Val Ser Ala Ala Arg Arg Leu Gly Val Glu His Thr Thr
            20                  25                  30

Val Ser Arg Arg Ile Arg Ala Leu Glu Ala Glu Leu Asp Ser Leu Leu
        35                  40                  45

Phe Glu Lys Ser Arg Ser Ala Gly Phe Val Leu Thr Glu Asp Gly
    50                  55                  60

<210> SEQ ID NO 91
<211> LENGTH: 63
<212> TYPE: PRT
<213> ORGANISM: Bosea sp.

<400> SEQUENCE: 91

Met Glu Arg Phe Asp Trp Asp Asp Leu Arg Phe Phe Leu Ala Val Ala
1               5                   10                  15

Arg Ser Gly Arg Leu Thr Ala Ala Arg Arg Leu Gly Ala Asp His
            20                  25                  30

Ala Thr Val Ser Arg Arg Ile Thr Ser Leu Glu Glu Ala Leu Lys Ala
        35                  40                  45

Lys Leu Phe Glu Arg Arg Pro Gln Gly Tyr Thr Leu Thr Ala His
    50                  55                  60

<210> SEQ ID NO 92
<211> LENGTH: 63
<212> TYPE: PRT
<213> ORGANISM: Bradyrhizobium elkanii

<400> SEQUENCE: 92

Met Leu Asp Gln Gly Gly Gly Thr Ile Asp Trp Asp Phe Arg Phe
1               5                   10                  15

Val Leu Ala Ile Val Arg Gly Gly Ser Val Ser Ala Ala Ala Lys Gln
            20                  25                  30

Leu Gly Val Asp His Ala Thr Val Ile Arg Arg Val Asp Arg Leu Glu
        35                  40                  45

Arg His Leu Ser Ala Lys Leu Phe Asp Arg Arg Lys Thr Gly Tyr
    50                  55                  60

<210> SEQ ID NO 93
<211> LENGTH: 63
<212> TYPE: PRT
<213> ORGANISM: Burkholderia ambifaria

<400> SEQUENCE: 93

Met Arg His Thr Pro Glu Pro Val Ser Gly Asn Leu Asn Trp Asp Asp
1               5                   10                  15

Leu Arg Phe Phe Leu Glu Val Ala Arg Thr Gln Arg Ala Ser Gly Ala
            20                  25                  30

Ala Lys Arg Leu Gly Val Asp Tyr Thr Thr Val Ala Arg Arg Ile Arg
        35                  40                  45

Ala Leu Glu Ala Ala Met Gly Thr Leu Leu Phe Asp Lys Ser Arg
    50                  55                  60

<210> SEQ ID NO 94
<211> LENGTH: 63
<212> TYPE: PRT
<213> ORGANISM: Burkholderia ferrariae

<400> SEQUENCE: 94

Met Gln Lys Asn Thr Thr Ser Lys Leu Glu Thr Leu Asn Trp Asp Asp

```
                1               5                  10                 15
Leu Arg Tyr Phe Leu Glu Val Ala Arg Thr Gln Arg Ala Ser Ala Ala
                20                 25                 30

Ala Lys Arg Leu Gly Val Asp His Thr Thr Val Ala Arg Arg Val Arg
        35                 40                 45

Glu Leu Glu Thr Ala Leu Gly Thr Val Leu Phe Asp Lys Ser Arg
    50                 55                 60
```

<210> SEQ ID NO 95
<211> LENGTH: 63
<212> TYPE: PRT
<213> ORGANISM: Burkholderia lata

<400> SEQUENCE: 95

```
Met Arg His Ala Thr Glu Pro Val Ser Gly Asn Leu Asn Trp Asp Asp
1               5                  10                 15

Leu Arg Phe Phe Leu Glu Val Ala Arg Thr Gln Arg Ala Ser Gly Ala
                20                 25                 30

Ala Lys Arg Leu Gly Val Asp Tyr Thr Thr Val Ala Arg Arg Ile Arg
        35                 40                 45

Ala Leu Glu Ala Ala Met Gly Thr Leu Leu Phe Asp Lys Ser Arg
    50                 55                 60
```

<210> SEQ ID NO 96
<211> LENGTH: 63
<212> TYPE: PRT
<213> ORGANISM: Burkholderia oxyphila

<400> SEQUENCE: 96

```
Met Gln Lys Ser Thr Thr Arg Pro Met Glu Thr Leu Asn Trp Asp Asp
1               5                  10                 15

Leu Arg Tyr Phe Leu Glu Val Ala Arg Thr Gln Arg Ala Ser Gly Ala
                20                 25                 30

Ala Arg Arg Leu Gly Val Asp His Thr Thr Val Ala Arg Arg Val Arg
        35                 40                 45

Glu Leu Glu Ala Ala Leu Gly Thr Val Leu Phe Asp Lys Ser Arg
    50                 55                 60
```

<210> SEQ ID NO 97
<211> LENGTH: 63
<212> TYPE: PRT
<213> ORGANISM: Burkholderia ubonensis

<400> SEQUENCE: 97

```
Met Arg His His Pro Glu Pro Val Ser Gly Asn Leu Asn Trp Asp Asp
1               5                  10                 15

Leu Arg Phe Phe Leu Glu Val Ala Arg Thr Gln Arg Ala Ser Gly Ala
                20                 25                 30

Ala Lys Arg Leu Gly Val Asp Tyr Thr Thr Val Ala Arg Arg Ile Arg
        35                 40                 45

Ala Leu Glu Glu Ala Met Gly Thr Leu Leu Phe Asp Lys Ser Arg
    50                 55                 60
```

<210> SEQ ID NO 98
<211> LENGTH: 63
<212> TYPE: PRT
<213> ORGANISM: Chelatococcus sp.

<400> SEQUENCE: 98

Met Asn Arg Phe Asp Trp Asp Asp Leu Arg Phe Phe Leu Ala Val Ala
1               5                   10                  15

Arg Ala Gly Arg Leu Thr Val Ala Ala Arg Arg Leu Gly Ala Asp His
            20                  25                  30

Ala Thr Val Ser Arg Arg Ile Thr Ala Leu Glu Asp Ala Leu Lys Ala
        35                  40                  45

Lys Leu Phe Glu Arg Arg Pro Gln Gly Tyr Ala Leu Thr Glu His
50                  55                  60

<210> SEQ ID NO 99
<211> LENGTH: 63
<212> TYPE: PRT
<213> ORGANISM: Collimonas arenae

<400> SEQUENCE: 99

Met Leu Asp Trp Asp Asn Leu Arg Val Phe Leu Glu Leu Thr Arg Ser
1               5                   10                  15

Gln Gly Leu Val Glu Ala Ala Lys Lys Leu Gly Ile Asp His Ser Thr
            20                  25                  30

Val Ser Arg Arg Met Arg Arg Phe Glu Glu Gln Val Gly Ser Gln Leu
        35                  40                  45

Phe Glu Arg Asn Asn Gln Gly Tyr Thr Leu Thr Ala Glu Gly His
50                  55                  60

<210> SEQ ID NO 100
<211> LENGTH: 63
<212> TYPE: PRT
<213> ORGANISM: Collimonas fungivorans

<400> SEQUENCE: 100

Met Gln Asn Lys Glu Lys Gln Val Lys Ser Thr Lys Ala Met Leu Asp
1               5                   10                  15

Trp Asp Asn Leu Arg Val Phe Leu Glu Leu Thr Arg Ser Gln Gly Leu
            20                  25                  30

Val Glu Thr Ala Lys Lys Leu Gly Ile Asp His Ser Thr Val Ser Arg
        35                  40                  45

Arg Met His Arg Phe Glu Glu Gln Val Gly Ser Gln Leu Phe Glu
50                  55                  60

<210> SEQ ID NO 101
<211> LENGTH: 63
<212> TYPE: PRT
<213> ORGANISM: Comamonas aquatica

<400> SEQUENCE: 101

Met Asp Trp Asp His Leu Arg Phe Phe Trp Ala Leu Val Gln Ala Gly
1               5                   10                  15

Thr Leu Val Gly Ala Ala Lys Ala Leu Gly Val Glu His Thr Thr Val
            20                  25                  30

Ser Arg Arg Ile Gln Ala Leu Glu Lys Gln Leu Gly Ala Thr Leu Phe
        35                  40                  45

Thr Arg Glu Gly Ser Gly Tyr Lys Leu Thr Asp Ala Gly Arg Gln
50                  55                  60

<210> SEQ ID NO 102
<211> LENGTH: 63
<212> TYPE: PRT
<213> ORGANISM: Comamonas badia

<400> SEQUENCE: 102

```
Met Thr Lys Pro Ala Gly Asn Asp Trp Asp Asn Leu Arg Tyr Phe Leu
1               5                   10                  15

Glu Leu Ala Arg Thr Gly Thr Leu Ala Ala Ala Arg Arg Thr Gly
            20                  25                  30

Val Glu His Thr Thr Val Ala Arg Arg Ile Leu Gln Leu Glu Lys Ser
            35                  40                  45

Met Ala Val Pro Leu Phe Ala Arg Glu Ala Ala Gly His Arg Leu
50                  55                  60
```

<210> SEQ ID NO 103
<211> LENGTH: 63
<212> TYPE: PRT
<213> ORGANISM: Comamonas composti

<400> SEQUENCE: 103

```
Met Asp Trp Asp His Leu Arg Phe Phe Ala Glu Leu Ala Arg Ser Gly
1               5                   10                  15

Ser Met Ala Ala Ala Arg Arg Leu Gly Val Glu His Thr Thr Val
            20                  25                  30

Ser Arg Arg Ile Gln Ala Leu Glu Lys Gln Leu Gly Ala Val Leu Phe
            35                  40                  45

Ala Arg Glu Val Gly Gln Trp Arg Leu Thr Glu Gly Arg Gln
50                  55                  60
```

<210> SEQ ID NO 104
<211> LENGTH: 63
<212> TYPE: PRT
<213> ORGANISM: Comamonas granuli

<400> SEQUENCE: 104

```
Met Asp Trp Asp Asn Leu Arg Phe Phe Leu Glu Leu Ala Arg Ala Gly
1               5                   10                  15

Thr Leu Val Gly Ala Ala Arg Arg Leu Gly Val Asp His Thr Thr Val
            20                  25                  30

Ala Arg Arg Ile Gln Gly Leu Glu Lys Gln Val Asp Ala Ala Leu Phe
            35                  40                  45

Ala Arg Glu Ala Leu Gly His Arg Leu Thr Glu Ala Gly Arg Ala
50                  55                  60
```

<210> SEQ ID NO 105
<211> LENGTH: 63
<212> TYPE: PRT
<213> ORGANISM: Comamonas testosteroni

<400> SEQUENCE: 105

```
Met Asp Trp Asp His Leu Arg Phe Phe Gly Glu Leu Ala Arg Ser Gly
1               5                   10                  15

Ser Met Ala Ala Ala Arg Arg Met Gly Val Glu His Thr Thr Val
            20                  25                  30

Ser Arg Arg Ile Gln Ala Leu Glu Lys Gln Leu Gly Ala Val Leu Phe
            35                  40                  45

Ala Arg Glu Gly Gly Gln Trp Arg Leu Thr Glu Ala Gly Arg Gln
50                  55                  60
```

<210> SEQ ID NO 106
<211> LENGTH: 63
<212> TYPE: PRT
<213> ORGANISM: Curvibacter gracilis -continued

<400> SEQUENCE: 106

Met Asp Trp Asn Asn Leu Arg Tyr Phe Leu Glu Leu Ala Arg Thr Gly
1               5                   10                  15

Thr Leu Val Asn Ala Ala Arg Arg Leu Glu Val Asp His Thr Thr Val
            20                  25                  30

Ala Arg Arg Leu Gln Ala Leu Glu Lys Glu Val Gly Thr Pro Leu Phe
        35                  40                  45

Ala Arg Glu Ala Gly Gly His Arg Leu Thr Glu Ala Gly Arg Gln
    50                  55                  60

<210> SEQ ID NO 107
<211> LENGTH: 63
<212> TYPE: PRT
<213> ORGANISM: Curvibacter lanceolatus

<400> SEQUENCE: 107

Met Asp Trp Asn Asn Leu Arg Tyr Phe Leu Glu Leu Ala Arg Thr Gly
1               5                   10                  15

Thr Leu Val Asn Ala Ala Arg Arg Leu Glu Val Asp His Thr Thr Val
            20                  25                  30

Ala Arg Arg Leu Gln Ala Leu Glu Lys Glu Val Gly Thr Pro Leu Phe
        35                  40                  45

Ala Arg Glu Ala Gly Gly His Arg Leu Thr Glu Ala Gly Arg Gln
    50                  55                  60

<210> SEQ ID NO 108
<211> LENGTH: 63
<212> TYPE: PRT
<213> ORGANISM: Derxia gummosa

<400> SEQUENCE: 108

Met Asp Trp Asp Asn Leu Arg Tyr Phe Leu Glu Leu Ser Arg Ser Gly
1               5                   10                  15

Arg Leu Ala Val Ala Ala Arg Arg Leu Gly Val Asp His Thr Thr Val
            20                  25                  30

Ser Arg Arg Val Gln Ala Leu Glu Thr Ala Val Gly Gln Pro Leu Phe
        35                  40                  45

Val Arg Glu Ala Gly Gly His Val Leu Thr Glu Ala Gly Arg Arg
    50                  55                  60

<210> SEQ ID NO 109
<211> LENGTH: 63
<212> TYPE: PRT
<213> ORGANISM: Halomonas elongata

<400> SEQUENCE: 109

Met Leu Asp Trp Gln Asp Ile Gln Ile Phe Leu Glu Val Ala Arg Ser
1               5                   10                  15

Gln Arg Leu Ala Asp Ala Ala Arg Arg Leu Gly Leu Asp His Ser Thr
            20                  25                  30

Leu Ser Arg Arg Thr Arg Arg Phe Glu Gln Arg Leu Asn Thr Gln Leu
        35                  40                  45

Phe Glu Arg Ser Thr His Gly Tyr His Leu Thr Glu Ala Gly His
    50                  55                  60

<210> SEQ ID NO 110
<211> LENGTH: 63
<212> TYPE: PRT
<213> ORGANISM: Halomonas halocynthiae

```
<400> SEQUENCE: 110

Met Leu Asp Trp Gln Asp Ile Gln Ile Phe Leu Glu Val Ala Arg Ser
1               5                   10                  15

Glu Arg Leu Thr Asp Ala Ala Arg Arg Leu Gly Leu Asp His Ser Thr
            20                  25                  30

Leu Ser Arg Arg Thr Arg Arg Phe Glu His Lys Leu Asn Thr Gln Leu
        35                  40                  45

Phe Glu Arg Ser Thr His Gly Tyr His Leu Thr Thr Ala Gly Gln
    50                  55                  60

<210> SEQ ID NO 111
<211> LENGTH: 63
<212> TYPE: PRT
<213> ORGANISM: Halomonas sp.

<400> SEQUENCE: 111

Met Leu Asp Trp Gln Asp Ile Gln Ile Phe Leu Glu Val Ala Arg Ser
1               5                   10                  15

Gln Arg Leu Thr Asp Ala Ala Arg Arg Leu Gly Leu Asp His Ser Thr
            20                  25                  30

Leu Ser Arg Arg Thr Arg Arg Phe Glu Gln Lys Leu Asn Thr Gln Leu
        35                  40                  45

Phe Glu Arg Ser Thr His Gly Tyr His Leu Thr Glu Ala Gly Gln
    50                  55                  60

<210> SEQ ID NO 112
<211> LENGTH: 63
<212> TYPE: PRT
<213> ORGANISM: Herbaspirillum huttiense

<400> SEQUENCE: 112

Met Leu Asp Trp Asp Asn Leu Arg Ile Phe Leu Glu Leu Thr Arg Ser
1               5                   10                  15

Gln Gly Leu Val Asp Ala Ala Lys Lys Leu Gly Ile Asp His Ser Thr
            20                  25                  30

Val Ser Arg Arg Met Lys Arg Phe Glu Glu Gln Val Gly Ser Gln Leu
        35                  40                  45

Phe Asp Arg Asn Asn His Gly Tyr Lys Leu Thr Ala Asp Gly Tyr
    50                  55                  60

<210> SEQ ID NO 113
<211> LENGTH: 63
<212> TYPE: PRT
<213> ORGANISM: Herbaspirillum lusitanum

<400> SEQUENCE: 113

Met Met Asp Trp Asp Asn Leu Arg Val Phe Leu Glu Leu Thr Arg Ser
1               5                   10                  15

Gln Gly Leu Val Asp Ala Ala Lys Lys Leu Gly Ile Asp His Ser Thr
            20                  25                  30

Val Ser Arg Arg Ile Lys Arg Phe Glu Glu Gln Val Gly Ser Gln Leu
        35                  40                  45

Phe Asp Arg Asn Asn His Gly Tyr Ser Leu Thr Ala Asp Gly Tyr
    50                  55                  60

<210> SEQ ID NO 114
<211> LENGTH: 63
<212> TYPE: PRT
```

<213> ORGANISM: Herbaspirillum seropedicae

<400> SEQUENCE: 114

Met Leu Asp Trp Asp Asn Leu Arg Ile Phe Leu Glu Leu Thr Arg Ser
1               5                   10                  15

Gln Gly Leu Val Asp Ala Ala Lys Lys Leu Gly Ile Asp His Ser Thr
            20                  25                  30

Val Ser Arg Arg Met Lys Arg Phe Glu Glu Gln Val Gly Ser Gln Leu
        35                  40                  45

Phe Asp Arg Asn Asn His Gly Tyr Lys Leu Thr Ala Asp Gly Tyr
    50                  55                  60

<210> SEQ ID NO 115
<211> LENGTH: 63
<212> TYPE: PRT
<213> ORGANISM: Herbaspirillum sp.

<400> SEQUENCE: 115

Met Leu Asp Trp Asp Asn Leu Arg Ile Phe Leu Glu Leu Thr Arg Ser
1               5                   10                  15

Gln Gly Leu Val Asp Ala Ala Lys Lys Leu Gly Ile Asp His Ser Thr
            20                  25                  30

Val Ser Arg Arg Met Lys Arg Phe Glu Glu Gln Val Gly Ser Gln Leu
        35                  40                  45

Phe Asp Arg Asn Asn His Gly Tyr Lys Leu Thr Ala Asp Gly Tyr
    50                  55                  60

<210> SEQ ID NO 116
<211> LENGTH: 63
<212> TYPE: PRT
<213> ORGANISM: Janthinobacterium lividum

<400> SEQUENCE: 116

Met Leu Asp Trp Asp Asn Val Arg Val Phe Leu Glu Leu Thr Arg Ser
1               5                   10                  15

Ala Gly Leu Val Asp Ala Ala Lys Lys Leu Gly Ile Asp His Ser Thr
            20                  25                  30

Val Ser Arg Arg Met Arg Lys Phe Glu Glu Gln Val Gly Thr Gln Leu
        35                  40                  45

Phe Asp Arg Asn Tyr Val Gly Tyr Gln Leu Thr Pro Glu Gly His
    50                  55                  60

<210> SEQ ID NO 117
<211> LENGTH: 63
<212> TYPE: PRT
<213> ORGANISM: Janthinobacterium sp.

<400> SEQUENCE: 117

Met Leu Asp Trp Asp Asn Val Arg Val Phe Leu Glu Leu Thr Arg Ser
1               5                   10                  15

Ala Gly Leu Val Asp Ala Ala Lys Lys Leu Gly Ile Asp His Ser Thr
            20                  25                  30

Val Ser Arg Arg Met Arg Lys Phe Glu Glu Gln Val Gly Thr Gln Leu
        35                  40                  45

Phe Asp Arg Asn Tyr Val Gly Tyr Gln Leu Thr Pro Glu Gly His
    50                  55                  60

<210> SEQ ID NO 118
<211> LENGTH: 63

```
<212> TYPE: PRT
<213> ORGANISM: Kiloniella laminariae

<400> SEQUENCE: 118

Met Asn Pro Thr Phe Asp Trp Asn Asp Leu Arg Pro Phe Leu Ala Val
1               5                   10                  15

Ala Arg Thr Gly Lys Leu Thr Ile Ala Ala Lys Arg Leu Lys Val Asp
            20                  25                  30

His Thr Thr Val Ser Arg Arg Ile Gln Ala Leu Glu Asn Ala Leu Asn
        35                  40                  45

Ala Thr Leu Phe Glu Arg Gly Pro Gln Gly Tyr Ala Leu Thr Glu
    50                  55                  60

<210> SEQ ID NO 119
<211> LENGTH: 63
<212> TYPE: PRT
<213> ORGANISM: Magnetospirillum gryphiswaldense

<400> SEQUENCE: 119

Met Asp Trp Asp Asn Leu Arg Ile Phe Leu Glu Leu Ala Arg Gly Arg
1               5                   10                  15

Arg Leu Met Asp Ala Ala Glu Arg Leu Gly Ile Asp Tyr Ser Thr Val
            20                  25                  30

Ser Arg Arg Ile Arg Arg Phe Glu Gln Glu Leu Gly Thr Gln Leu Phe
        35                  40                  45

Asp Arg Asn Asn Gln Gly Tyr Thr Leu Thr Ala Gln Gly Leu His
    50                  55                  60

<210> SEQ ID NO 120
<211> LENGTH: 63
<212> TYPE: PRT
<213> ORGANISM: Marinobacterium stanieri

<400> SEQUENCE: 120

Met Leu Asn Trp Gln Asp Met Gln Ile Phe Leu Glu Val Ala Arg Ala
1               5                   10                  15

Asn Arg Leu Thr Asp Ala Ala Arg Arg Leu Asn Ile Asp His Ser Thr
            20                  25                  30

Val Ser Arg Arg Ile Arg Arg Phe Glu Ala Ser Leu Asn Ala Gln Leu
        35                  40                  45

Phe Glu Arg Ser Thr His Gly Tyr Glu Leu Ala Pro Ala Gly Lys
    50                  55                  60

<210> SEQ ID NO 121
<211> LENGTH: 63
<212> TYPE: PRT
<213> ORGANISM: Microvirga sp.

<400> SEQUENCE: 121

Met Ser Ala Phe Asp Trp Asp Asp Leu Arg Phe Phe Leu Ala Val Ala
1               5                   10                  15

Arg Ala Gly Arg Leu Thr Ala Ala Arg Gln Leu Glu Ala Asp His
            20                  25                  30

Thr Thr Val Ser Arg Arg Ile Ser Ala Leu Glu Ala Ser Leu Lys Ala
        35                  40                  45

Lys Leu Phe Glu Arg Ser Pro Gln Gly Tyr Thr Leu Thr Glu Pro
    50                  55                  60

<210> SEQ ID NO 122
```

```
<211> LENGTH: 63
<212> TYPE: PRT
<213> ORGANISM: Microvirgula aerodenitrificans

<400> SEQUENCE: 122

Met Asp Trp Asp Asn Leu Arg Val Phe Leu Glu Ile Ala Arg Ser Glu
1               5                   10                  15

Thr Leu Val Gln Ala Ala Arg Arg Leu Gly Met Asp His Ser Thr Val
            20                  25                  30

Ser Arg Arg Leu Arg Arg Phe Glu Gln Gln Leu Gly Ser Gln Leu Phe
        35                  40                  45

Glu Arg Asn Asn Gln Gly Ala Ala Leu Thr Pro Gln Gly Tyr Gln
    50                  55                  60

<210> SEQ ID NO 123
<211> LENGTH: 63
<212> TYPE: PRT
<213> ORGANISM: Mumia flava

<400> SEQUENCE: 123

Met Arg His Ala Thr Glu Pro Val Ser Gly Asn Leu Asn Trp Asp Asp
1               5                   10                  15

Leu Arg Phe Phe Leu Glu Val Ala Arg Thr Gln Arg Ala Ser Gly Ala
            20                  25                  30

Ala Lys Arg Leu Gly Val Asp Tyr Thr Thr Val Ala Arg Arg Ile Arg
        35                  40                  45

Ala Leu Glu Ala Ala Met Gly Thr Leu Leu Phe Asp Lys Ser Arg
    50                  55                  60

<210> SEQ ID NO 124
<211> LENGTH: 63
<212> TYPE: PRT
<213> ORGANISM: Niveispirillum irakense

<400> SEQUENCE: 124

Met Ala Glu Arg Phe Asp Trp Asp Asp Leu Gln Ser Phe Leu Ala Val
1               5                   10                  15

Ala Arg Ser Gly Arg Leu Thr Leu Ala Ala Arg Arg Met Gly Val Asp
            20                  25                  30

His Thr Thr Leu Gly Arg Arg Leu Thr Gly Leu Glu Arg Ala Leu Gly
        35                  40                  45

Thr Asn Leu Phe Glu Arg His Ala Thr Gly Tyr Ser Leu Thr Gln
    50                  55                  60

<210> SEQ ID NO 125
<211> LENGTH: 63
<212> TYPE: PRT
<213> ORGANISM: Oligella urethralis

<400> SEQUENCE: 125

Met Met Asp Trp Asp Gly Leu Arg Tyr Phe Leu Ala Val Ala Arg Thr
1               5                   10                  15

Ser Lys Ile Ser Glu Ala Gly Arg Arg Leu Gly Val Glu His Thr Thr
            20                  25                  30

Val Ala Arg Arg Ile Arg Gln Leu Glu Gln Ala Met Gly Thr Val Leu
        35                  40                  45

Phe Asp Lys Ser Arg Arg Tyr Gly Tyr Leu Leu Thr Glu Ala Gly
    50                  55                  60
```

-continued

```
<210> SEQ ID NO 126
<211> LENGTH: 63
<212> TYPE: PRT
<213> ORGANISM: Ottowia thiooxydans

<400> SEQUENCE: 126

Met Asp Trp Asp Leu Leu Arg Tyr Phe Glu Leu Ala Arg Thr Gly
1               5                   10                  15

Lys Leu Thr Ala Ala Ala Arg Arg Leu Asp Val Asp His Thr Thr Val
                20                  25                  30

Ser Arg Arg Val Gln Thr Leu Glu Lys Lys Leu Gly Ser Thr Leu Phe
            35                  40                  45

Val Arg Thr Ser Ser Gly Met Glu Leu Thr Glu Glu Gly Arg Leu
    50                  55                  60

<210> SEQ ID NO 127
<211> LENGTH: 63
<212> TYPE: PRT
<213> ORGANISM: Pandoraea apista

<400> SEQUENCE: 127

Met Ala Gly Ala Ser Ser Thr Glu Pro Arg Pro Asp Trp Asp Leu
1               5                   10                  15

Arg Tyr Phe Leu Glu Val Ala Arg Thr Gln Arg Val Ser Ala Ala Ala
                20                  25                  30

Gln Arg Leu Gly Val Asp His Thr Thr Val Ser Arg Val Arg Ala
            35                  40                  45

Leu Glu Gln Ala Leu Gly Thr Leu Leu Phe Asp Lys Ser Arg Asn
    50                  55                  60

<210> SEQ ID NO 128
<211> LENGTH: 58
<212> TYPE: PRT
<213> ORGANISM: Pandoraea sp.

<400> SEQUENCE: 128

Met Arg Tyr Phe Leu Glu Val Ala Arg Thr Gln Arg Val Ser Ala Ala
1               5                   10                  15

Ala Val Arg Leu Gly Val Asp His Thr Thr Val Ser Arg Arg Val Arg
                20                  25                  30

Ala Leu Glu Gln Ser Leu Gly Thr Leu Leu Phe Asp Lys Ser Arg Asn
            35                  40                  45

Ala Gly Phe Ala Leu Thr Pro Glu Gly Gln
    50                  55

<210> SEQ ID NO 129
<211> LENGTH: 63
<212> TYPE: PRT
<213> ORGANISM: Pannonibacter phragmitetus

<400> SEQUENCE: 129

Met Asn Trp Asp Asp Leu Arg Ile Phe Leu Ala Val Ala Arg Ala Gly
1               5                   10                  15

Gln Met Leu Gly Ala Ala Lys Arg Leu Gly Val Asn His Ala Thr Val
                20                  25                  30

Ala Arg Arg Leu Thr Ala Leu Glu Asp Ser Leu Asn Thr Arg Leu Val
            35                  40                  45

Glu Arg Gly Thr Thr Gly Cys Ser Leu Thr Glu Ala Gly Glu Arg
    50                  55                  60
```

-continued

<210> SEQ ID NO 130
<211> LENGTH: 63
<212> TYPE: PRT
<213> ORGANISM: Perlucidibaca piscinae

<400> SEQUENCE: 130

Met Gln Lys Ser Thr Ser Leu Thr Ser Asn Met Asn Trp Asp Asp Leu
1               5                   10                  15

Arg Val Phe Leu Ala Val Leu Arg His Gly Ser Ala Ser Gln Ala Ala
            20                  25                  30

Arg Gln Leu Gly Leu Asn His Thr Thr Val Ala Arg Arg Ile Arg Leu
        35                  40                  45

Leu Glu Glu Ala Leu Gly Thr Leu Leu Phe Glu Arg Ser Arg Ser
    50                  55                  60

<210> SEQ ID NO 131
<211> LENGTH: 63
<212> TYPE: PRT
<213> ORGANISM: Polynucleobacter necessarius

<400> SEQUENCE: 131

Met Asn Ser Met Asn Trp Asp His Leu Gln Tyr Phe Leu Ala Leu Ala
1               5                   10                  15

Lys Asp Gly Arg Leu Ile Val Ala Ala Arg Ser Leu Gly Val Asn His
            20                  25                  30

Thr Thr Val Ser Arg Arg Ile Gln Ala Leu Glu Arg Glu Met Gly Val
        35                  40                  45

Gln Leu Phe Ser Arg Asn Asn Leu Gly Phe Glu Leu Thr Glu Ala
    50                  55                  60

<210> SEQ ID NO 132
<211> LENGTH: 63
<212> TYPE: PRT
<213> ORGANISM: Pseudogulbenkiania ferrooxidans

<400> SEQUENCE: 132

Met Gln Lys Asn Pro Ile Pro Val Asp Arg Leu Asn Trp Asp Asp Ile
1               5                   10                  15

Lys Phe Phe Leu Glu Val Ala Arg Thr His Thr Ala Ser Ser Ala Ala
            20                  25                  30

Lys Arg Leu Gly Val Asp Tyr Thr Thr Val Ser Arg Arg Ile Arg Ala
        35                  40                  45

Leu Glu Gln Ala Leu Gly Ala Leu Leu Phe Glu Lys Ser Arg Ser
    50                  55                  60

<210> SEQ ID NO 133
<211> LENGTH: 63
<212> TYPE: PRT
<213> ORGANISM: Pseudomonas aeruginosa

<400> SEQUENCE: 133

Met Asp Trp Asp Asn Leu Arg Phe Phe Leu Glu Leu Ser Arg Ser Arg
1               5                   10                  15

Thr Leu Ser Ala Ala Ala Arg Arg Leu Glu Val Asp Tyr Thr Thr Val
            20                  25                  30

Ser Arg Arg Ile Gln Thr Leu Glu Lys Asn Leu Gly Ala Gln Leu Phe
        35                  40                  45

Ser Arg Gln Ala Asn Gly Tyr Ala Leu Ser Glu Ala Gly Arg Ser
    50                  55                  60

<210> SEQ ID NO 134
<211> LENGTH: 63
<212> TYPE: PRT
<213> ORGANISM: Pseudomonas alkylphenolia

<400> SEQUENCE: 134

Met Gln Lys Asn Ile Thr Ser Leu Gly Ala Leu Asn Trp Asp Asp Leu
1               5                   10                  15

Lys Phe Phe Leu Glu Val Ala Arg Thr Arg Lys Ala Ser Ser Ala Ala
            20                  25                  30

Lys Arg Leu Gly Val Asp Tyr Thr Thr Val Ser Arg Arg Ile Ser Ser
        35                  40                  45

Leu Glu Leu Ala Leu Gly Thr Leu Leu Phe Glu Lys Ser Arg Thr
    50                  55                  60

<210> SEQ ID NO 135
<211> LENGTH: 63
<212> TYPE: PRT
<213> ORGANISM: Pseudomonas amygdali

<400> SEQUENCE: 135

Met Gln Lys Asn Ile Thr Ser Leu Gly Leu Leu Asn Trp Asp Asp Leu
1               5                   10                  15

Lys Phe Phe Leu Glu Val Ala Arg Thr Arg Lys Val Ser Ser Ala Ala
            20                  25                  30

Arg Arg Leu Ala Val Asp Tyr Thr Thr Val Ser Arg Arg Ile Asn Ser
        35                  40                  45

Leu Glu Thr Ser Leu Gly Thr Leu Leu Phe Glu Lys Ser Arg Asn
    50                  55                  60

<210> SEQ ID NO 136
<211> LENGTH: 63
<212> TYPE: PRT
<213> ORGANISM: Pseudomonas azotifigens

<400> SEQUENCE: 136

Met Asp Trp Asp Asn Leu Arg Phe Phe Leu Glu Val Ala Arg Ala Gly
1               5                   10                  15

Arg Leu Thr Thr Ala Ala Arg Arg Leu Gly Val Asp His Thr Thr Val
            20                  25                  30

Ser Arg Arg Leu Gln Ala Leu Glu Lys Ser Thr Gly Leu Gln Leu Phe
        35                  40                  45

Leu Arg Glu Pro Gly Gly Tyr Arg Leu Thr Glu Ala Gly Arg Gly
    50                  55                  60

<210> SEQ ID NO 137
<211> LENGTH: 63
<212> TYPE: PRT
<213> ORGANISM: Pseudomonas balearica

<400> SEQUENCE: 137

Met Asp Trp Asp Asn Leu Arg Tyr Phe Leu Glu Val Ala Arg Ala Gly
1               5                   10                  15

Arg Leu Thr Ser Ala Ala Arg Arg Leu Asn Val Asp His Thr Thr Val
            20                  25                  30

Ser Arg Arg Leu Gln Ala Leu Glu Lys Ser Met Gly Met Gln Leu Phe
        35                  40                  45

Val Arg Glu Pro Gly Gly Tyr Arg Leu Thr Glu Ala Gly Arg Asn

<210> SEQ ID NO 138
<211> LENGTH: 63
<212> TYPE: PRT
<213> ORGANISM: Pseudomonas bauzanensis

<400> SEQUENCE: 138

Met Asp Trp Asp Asn Leu Arg Phe Phe Leu Glu Leu Ser Arg Ala Gly
1               5                   10                  15

Arg Leu Thr Thr Ala Ala Arg Arg Leu Gly Val Asp His Thr Thr Val
            20                  25                  30

Ser Arg Arg Leu Gln Ala Leu Glu Lys Ser Leu Gly Val Ala Leu Phe
        35                  40                  45

Ile Arg Asp Thr Ser Gly Tyr Thr Leu Thr Glu Ala Gly Arg Ser
    50                  55                  60

<210> SEQ ID NO 139
<211> LENGTH: 63
<212> TYPE: PRT
<213> ORGANISM: Pseudomonas chloritidismutans

<400> SEQUENCE: 139

Met Asp Trp Asp Asn Leu Arg Tyr Phe Leu Glu Val Ala Arg Ala Gly
1               5                   10                  15

Arg Leu Thr Thr Ala Ala Arg Arg Leu Ala Val Asp His Thr Thr Val
            20                  25                  30

Ser Arg Arg Leu Gln Ala Leu Glu Lys Ser Met Gly Leu Gln Leu Phe
        35                  40                  45

Leu Arg Glu Pro Gly Gly Tyr Lys Leu Thr Glu Ala Gly Cys Asn
    50                  55                  60

<210> SEQ ID NO 140
<211> LENGTH: 63
<212> TYPE: PRT
<213> ORGANISM: Pseudomonas chlororaphis

<400> SEQUENCE: 140

Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Thr Ala Ala
            20                  25                  30

Lys Arg Leu Ala Val Asp Tyr Thr Thr Val Ser Arg Arg Ile Ser Ser
        35                  40                  45

Leu Glu Ala Ala Leu Gly Thr Leu Leu Phe Glu Lys Ser Arg Thr
    50                  55                  60

<210> SEQ ID NO 141
<211> LENGTH: 63
<212> TYPE: PRT
<213> ORGANISM: Pseudomonas corrugata

<400> SEQUENCE: 141

Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Thr Ala Ala
            20                  25                  30

Lys Arg Leu Gly Val Asp Tyr Thr Thr Val Ser Arg Arg Ile Gly Ser
        35                  40                  45

```
Leu Glu Ala Ser Leu Gly Thr Leu Leu Phe Glu Lys Ser Arg Thr
    50                  55                  60
```

<210> SEQ ID NO 142
<211> LENGTH: 63
<212> TYPE: PRT
<213> ORGANISM: Pseudomonas cremoricolorata

<400> SEQUENCE: 142

```
Met Gln Lys Asp Pro Thr Ser Leu Ser Ala Leu Asn Trp Asp Leu
1               5                   10                  15

Lys Phe Phe Leu Glu Val Ala Arg Thr Arg Lys Ala Ser Ser Ala Ala
                20                  25                  30

Lys Arg Leu Gly Val Asp Tyr Thr Thr Val Ser Arg Arg Ile Ala Ser
            35                  40                  45

Leu Glu Ser Ala Leu Gly Thr Leu Leu Phe Glu Lys Ser Arg Ser
    50                  55                  60
```

<210> SEQ ID NO 143
<211> LENGTH: 63
<212> TYPE: PRT
<213> ORGANISM: Pseudomonas denitrificans

<400> SEQUENCE: 143

```
Met Asp Trp Asp Asn Leu Arg Phe Phe Leu Glu Leu Ser Arg Ala Gly
1               5                   10                  15

Lys Leu Thr Val Ala Ala Arg Arg Leu Gly Val Asp His Thr Thr Val
                20                  25                  30

Ala Arg Arg Leu Gln Ala Leu Glu Lys Ser Ile Gly Ala Gln Leu Leu
            35                  40                  45

Val Arg Glu Pro Gly Gly Tyr Arg Leu Thr Glu Ala Gly His Gly
    50                  55                  60
```

<210> SEQ ID NO 144
<211> LENGTH: 63
<212> TYPE: PRT
<213> ORGANISM: Pseudomonas fluorescens

<400> SEQUENCE: 144

```
Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Val Ala Ala
                20                  25                  30

Lys Arg Leu Ser Val Asp Tyr Thr Thr Val Ser Arg Arg Ile Ser Ser
            35                  40                  45

Leu Glu Gly Ser Leu Gly Thr Leu Leu Phe Glu Lys Ser Arg Thr
    50                  55                  60
```

<210> SEQ ID NO 145
<211> LENGTH: 63
<212> TYPE: PRT
<213> ORGANISM: Pseudomonas frederiksbergensis

<400> SEQUENCE: 145

```
Met Phe Asp Trp Asn Asp Leu Arg Tyr Phe Leu Glu Leu Gln Arg Ser
1               5                   10                  15

Gly Arg Leu Leu Thr Ala Ala Arg Arg Leu Asn Thr Thr His Ala Thr
                20                  25                  30

Val Ala Arg His Ile Glu Ala Ile Glu Lys Ser Leu Gly Thr Ala Leu
            35                  40                  45
```

```
Phe Val Gln His Ala Gln Gly Tyr Glu Leu Thr Pro Ala Gly Glu
    50                  55                  60

<210> SEQ ID NO 146
<211> LENGTH: 63
<212> TYPE: PRT
<213> ORGANISM: Pseudomonas fulva

<400> SEQUENCE: 146

Met Gln Lys Ser Met Met Ser Ala Gly Gln Met Asn Trp Asp Asp Leu
1               5                   10                  15

Lys Phe Phe Leu Glu Val Ala Arg Thr Arg Thr Ala Ser Ser Ala Ala
                20                  25                  30

Arg Arg Leu Gly Val Asp Tyr Thr Thr Val Ser Arg Arg Ile Gly Ala
            35                  40                  45

Leu Glu Lys Ala Leu Gly Thr Leu Leu Phe Glu Arg Ser Arg Ala
    50                  55                  60

<210> SEQ ID NO 147
<211> LENGTH: 63
<212> TYPE: PRT
<213> ORGANISM: Pseudomonas japonica

<400> SEQUENCE: 147

Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Ser Ala Ala
                20                  25                  30

Lys Arg Leu Gly Val Asp Tyr Thr Thr Val Ser Arg Arg Ile Ser Ser
            35                  40                  45

Leu Glu Gln Ala Leu Gly Thr Leu Leu Phe Glu Lys Ser Arg Thr
    50                  55                  60

<210> SEQ ID NO 148
<211> LENGTH: 63
<212> TYPE: PRT
<213> ORGANISM: Pseudomonas knackmussii

<400> SEQUENCE: 148

Met Asp Trp Asp Asn Leu Arg Phe Phe Leu Glu Leu Ser Arg Ala Gly
1               5                   10                  15

Lys Leu Thr Val Ala Ala Arg Arg Leu Gly Val Asp His Thr Thr Val
                20                  25                  30

Ala Arg Arg Leu Gln Ala Leu Glu Lys Ser Ile Gly Ala Gln Leu Leu
            35                  40                  45

Val Arg Glu Pro Ser Gly Tyr Arg Leu Thr Glu Ala Gly His Gly
    50                  55                  60

<210> SEQ ID NO 149
<211> LENGTH: 63
<212> TYPE: PRT
<213> ORGANISM: Pseudomonas lutea

<400> SEQUENCE: 149

Met Gln Lys Asn Ile Thr Ser Leu Ser Gly Leu Asn Trp Asp Asp Leu
1               5                   10                  15

Lys Phe Phe Leu Glu Val Ala Arg Thr Arg Lys Ala Ser Ser Ala Ala
                20                  25                  30

Lys Arg Leu Ala Val Asp Tyr Thr Thr Val Ser Arg Arg Ile Ser Ser
```

```
                35                  40                  45

Leu Glu Ala Ala Leu Gly Thr Leu Leu Phe Glu Lys Ser Arg Asn
     50                  55                  60

<210> SEQ ID NO 150
<211> LENGTH: 63
<212> TYPE: PRT
<213> ORGANISM: Pseudomonas mandelii

<400> SEQUENCE: 150

Met Gln Lys Arg Thr Thr Gln Ser His Val Asn Trp Asp Asp Met Arg
1               5                  10                  15

Phe Phe Leu Glu Val Ala Arg Ala His Thr Ala Ser Gly Ala Ala Arg
                20                  25                  30

Arg Leu Gly Val Asp Tyr Thr Thr Val Ser Arg Arg Ile Arg Ala Leu
            35                  40                  45

Glu Gln Ser Leu Gly Ala Leu Leu Phe Glu Lys Ser Arg Ala Ser
     50                  55                  60

<210> SEQ ID NO 151
<211> LENGTH: 63
<212> TYPE: PRT
<213> ORGANISM: Pseudomonas mediterranea

<400> SEQUENCE: 151

Met Gln Lys Asn Ile Thr Ser Leu Gly Ser Leu Asn Trp Asp Asp Leu
1               5                  10                  15

Lys Phe Phe Leu Glu Val Ala Arg Thr Arg Lys Ala Ser Thr Ala Ala
                20                  25                  30

Lys Arg Leu Gly Val Asp Tyr Thr Thr Val Ser Arg Arg Ile Gly Ser
            35                  40                  45

Leu Glu Ala Ser Leu Gly Thr Leu Leu Phe Glu Lys Ser Arg Thr
     50                  55                  60

<210> SEQ ID NO 152
<211> LENGTH: 63
<212> TYPE: PRT
<213> ORGANISM: Pseudomonas mendocina

<400> SEQUENCE: 152

Met Gln Lys Asn Met Val Leu Gly Arg Ile Asn Trp Asp Asp Leu Arg
1               5                  10                  15

Phe Phe Leu Glu Val Ala Arg Thr Arg Thr Ala Ser Ala Ala Ser Arg
                20                  25                  30

Arg Leu Gly Val Asp Tyr Thr Thr Val Ser Arg Arg Ile Arg Ser Leu
            35                  40                  45

Glu Gln Ser Leu Gly Ala Leu Leu Phe Glu Lys Ser Arg Ser Ala
     50                  55                  60

<210> SEQ ID NO 153
<211> LENGTH: 63
<212> TYPE: PRT
<213> ORGANISM: Pseudomonas monteilii

<400> SEQUENCE: 153

Met Gln Lys Asp Leu Thr Ser Leu Ser Ala Leu Asn Trp Asp Asp Leu
1               5                  10                  15

Lys Phe Phe Leu Glu Val Ala Arg Thr Arg Lys Ala Ser Ser Ala Ala
                20                  25                  30
```

```
Lys Arg Leu Ser Val Asp Tyr Thr Thr Val Ser Arg Arg Ile Ser Ser
             35                  40                  45

Leu Glu Gly Ala Leu Gly Thr Leu Leu Phe Glu Lys Ser Arg Thr
         50                  55                  60

<210> SEQ ID NO 154
<211> LENGTH: 63
<212> TYPE: PRT
<213> ORGANISM: Pseudomonas nitroreducens

<400> SEQUENCE: 154

Met Asp Trp Asp Asn Leu Arg Phe Phe Leu Glu Leu Ser Arg Ala Gly
1               5                   10                  15

Lys Leu Thr Val Ala Ala Arg Arg Leu Gly Val Asp His Thr Thr Val
             20                  25                  30

Ala Arg Arg Leu Gln Ala Leu Glu Lys Ser Ile Gly Ala Gln Leu Leu
         35                  40                  45

Val Arg Glu Pro Ala Gly Tyr Arg Leu Thr Glu Ala Gly His Gly
     50                  55                  60

<210> SEQ ID NO 155
<211> LENGTH: 63
<212> TYPE: PRT
<213> ORGANISM: Pseudomonas parafulva

<400> SEQUENCE: 155

Met Gln Lys Asp Leu Thr Ser Leu Ser Ala Leu Asn Trp Asp Asp Leu
1               5                   10                  15

Lys Phe Phe Leu Glu Val Ala Arg Thr Arg Lys Ala Ser Ser Ala Ala
             20                  25                  30

Lys Arg Leu Gly Val Asp Tyr Thr Thr Val Ser Arg Arg Ile Ser Ser
         35                  40                  45

Leu Glu Gly Ala Leu Gly Thr Leu Leu Phe Glu Lys Ser Arg Thr
     50                  55                  60

<210> SEQ ID NO 156
<211> LENGTH: 63
<212> TYPE: PRT
<213> ORGANISM: Pseudomonas plecoglossicida

<400> SEQUENCE: 156

Met Gln Lys Asp Leu Thr Ser Leu Ser Ala Leu Asn Trp Asp Asp Leu
1               5                   10                  15

Lys Phe Phe Leu Glu Val Ala Arg Thr Arg Lys Ala Ser Ser Ala Ala
             20                  25                  30

Lys Arg Leu Ser Val Asp Tyr Thr Thr Val Ser Arg Arg Ile Ser Ser
         35                  40                  45

Leu Glu Gly Ala Leu Gly Thr Leu Leu Phe Glu Lys Ser Arg Thr
     50                  55                  60

<210> SEQ ID NO 157
<211> LENGTH: 63
<212> TYPE: PRT
<213> ORGANISM: Pseudomonas protegens

<400> SEQUENCE: 157

Met Phe Asp Trp Asn Asp Leu Arg Phe Phe Leu Glu Leu Gln Arg Ser
1               5                   10                  15

Gly Arg Leu Leu Thr Ala Ala Arg Arg Leu Asn Thr Thr His Ala Thr
             20                  25                  30
```

```
Val Ala Arg His Ile Glu Ala Val Glu Lys Ala Leu Gly Thr Ala Leu
         35                  40                  45

Phe Val Gln His Ala Gln Gly Tyr Glu Leu Thr Pro Ala Gly Glu
 50                  55                  60
```

<210> SEQ ID NO 158
<211> LENGTH: 63
<212> TYPE: PRT
<213> ORGANISM: Pseudomonas pseudoalcaligenes

<400> SEQUENCE: 158

```
Met His Lys Ser Ser Asn Leu Asp Gln Leu Lys Trp Asp Asp Leu Arg
 1               5                  10                  15

Phe Phe Leu Glu Val Ala Arg Thr Arg Thr Ala Thr Gly Ala Ala Arg
             20                  25                  30

Arg Leu Gly Val Asp Tyr Thr Thr Val Ser Arg Arg Val Arg Ala Leu
         35                  40                  45

Glu Gln Ala Leu Gly Ala Leu Leu Phe Glu Lys Ser Arg Ala Ala
 50                  55                  60
```

<210> SEQ ID NO 159
<211> LENGTH: 63
<212> TYPE: PRT
<213> ORGANISM: Pseudomonas psychrotolerans

<400> SEQUENCE: 159

```
Met Gln Lys Ser Asn Asn Pro Ala Ala Arg Leu Asp Trp Asp Asp Leu
 1               5                  10                  15

Arg Phe Phe Leu Glu Val Ala Arg Thr Gln Lys Gly Ser Ala Ala Ala
             20                  25                  30

Arg Arg Leu Gly Val Asp Tyr Thr Thr Val Ser Arg Arg Ile Ala Ala
         35                  40                  45

Leu Glu Lys Ala Leu Gly Ala Leu Leu Phe Glu Lys Ser Arg Ser
 50                  55                  60
```

<210> SEQ ID NO 160
<211> LENGTH: 63
<212> TYPE: PRT
<213> ORGANISM: Pseudomonas putida

<400> SEQUENCE: 160

```
Met Asn Met Gln Lys Arg Thr Thr Gln Ser His Val Asn Trp Asp Asp
 1               5                  10                  15

Met Arg Phe Phe Leu Glu Val Ala Arg Ala Arg Thr Ala Ser Gly Ala
             20                  25                  30

Ala Arg Arg Leu Gly Val Asp Tyr Thr Thr Val Ser Arg Arg Ile Arg
         35                  40                  45

Ala Leu Glu Gln Ser Leu Gly Ala Leu Leu Phe Glu Lys Ser Arg
 50                  55                  60
```

<210> SEQ ID NO 161
<211> LENGTH: 63
<212> TYPE: PRT
<213> ORGANISM: Pseudomonas resinovorans

<400> SEQUENCE: 161

```
Met Gln Lys Thr Pro Asn Ser Val Gly Arg Leu Asn Trp Asp Asp Leu
 1               5                  10                  15

Lys Tyr Phe Leu Glu Val Ala Arg Thr Arg Thr Ala Ser Thr Ala Ala
```

```
            20                  25                  30

Arg Arg Leu Asp Val Asp Tyr Thr Thr Val Ser Arg Arg Ile Arg Ala
        35                  40                  45

Leu Glu Gln Gly Met Gly Ala Leu Leu Phe Glu Lys Ser Arg Asn
    50                  55                  60
```

<210> SEQ ID NO 162
<211> LENGTH: 63
<212> TYPE: PRT
<213> ORGANISM: Pseudomonas rhodesiae

<400> SEQUENCE: 162

```
Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Val Ala Ala
            20                  25                  30

Lys Arg Leu Ala Val Asp Tyr Thr Thr Val Ser Arg Arg Ile Ser Ser
        35                  40                  45

Leu Glu Val Ser Leu Gly Thr Leu Leu Phe Glu Lys Ser Arg Thr
    50                  55                  60
```

<210> SEQ ID NO 163
<211> LENGTH: 63
<212> TYPE: PRT
<213> ORGANISM: Pseudomonas savastanoi

<400> SEQUENCE: 163

```
Met Gln Lys Asn Ile Thr Ser Leu Gly Leu Leu Asn Trp Asp Asp Leu
1               5                   10                  15

Lys Phe Phe Leu Glu Val Ala Arg Thr Arg Lys Val Ser Ser Ala Ala
            20                  25                  30

Arg Arg Leu Ala Val Asp Tyr Thr Thr Val Ser Arg Arg Ile Asn Ser
        35                  40                  45

Leu Glu Thr Ser Leu Gly Thr Leu Leu Phe Glu Lys Ser Arg Asn
    50                  55                  60
```

<210> SEQ ID NO 164
<211> LENGTH: 63
<212> TYPE: PRT
<213> ORGANISM: Pseudomonas simiae

<400> SEQUENCE: 164

```
Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Val Ala Ala
            20                  25                  30

Lys Arg Leu Ala Val Asp Tyr Thr Thr Val Ser Arg Arg Ile Ser Ser
        35                  40                  45

Leu Glu Val Ser Leu Gly Thr Leu Leu Phe Glu Lys Ser Arg Thr
    50                  55                  60
```

<210> SEQ ID NO 165
<211> LENGTH: 63
<212> TYPE: PRT
<213> ORGANISM: Pseudomonas sp.

<400> SEQUENCE: 165

```
Met Asp Trp Asp Asn Leu Arg Phe Phe Leu Glu Leu Ser Arg Ala Gly
1               5                   10                  15
```

```
Lys Leu Thr Val Ala Ala Arg Arg Leu Gly Val Asp His Thr Val
                20                  25                  30

Ala Arg Arg Leu Gln Ala Leu Glu Lys Ser Ile Gly Ala Gln Leu Leu
            35                  40                  45

Val Arg Glu Pro Ser Gly Tyr Arg Leu Thr Glu Ala Gly His Gly
        50                  55                  60

<210> SEQ ID NO 166
<211> LENGTH: 63
<212> TYPE: PRT
<213> ORGANISM: Pseudomonas stutzeri

<400> SEQUENCE: 166

Met Asp Trp Asp Asn Leu Arg Phe Phe Leu Glu Leu Ser Arg Ala Gly
1               5                   10                  15

Lys Leu Thr Val Ala Ala Arg Arg Leu Ala Val Asp His Thr Thr Val
                20                  25                  30

Ala Arg Arg Val Gln Ala Leu Glu Lys Ser Leu Asp Arg Gln Leu Phe
            35                  40                  45

Ile Arg Ala Lys Ala Gly Tyr Arg Leu Ser Glu Ala Gly Arg Glu
        50                  55                  60

<210> SEQ ID NO 167
<211> LENGTH: 63
<212> TYPE: PRT
<213> ORGANISM: Pseudomonas syringae

<400> SEQUENCE: 167

Met Gln Lys Asn Ile Thr Ser Leu Ser Leu Leu Asn Trp Asp Asp Leu
1               5                   10                  15

Lys Phe Phe Leu Glu Val Ala Arg Thr Arg Lys Val Ser Ser Ala Ala
                20                  25                  30

Arg Arg Leu Ala Val Asp Tyr Thr Thr Val Ser Arg Arg Ile Asn Ser
            35                  40                  45

Leu Glu Thr Ser Leu Gly Thr Leu Leu Phe Glu Lys Ser Arg Asn
        50                  55                  60

<210> SEQ ID NO 168
<211> LENGTH: 63
<212> TYPE: PRT
<213> ORGANISM: Pseudomonas taiwanensis

<400> SEQUENCE: 168

Met Gln Lys Asp Leu Thr Ser Leu Ser Ala Leu Asn Trp Asp Asp Leu
1               5                   10                  15

Lys Phe Phe Leu Glu Val Ala Arg Thr Arg Lys Ala Ser Ser Ala Ala
                20                  25                  30

Lys Arg Leu Ser Val Asp Tyr Thr Thr Val Ser Arg Arg Ile Ser Ser
            35                  40                  45

Leu Glu Gly Ala Leu Gly Thr Leu Leu Phe Glu Lys Ser Arg Thr
        50                  55                  60

<210> SEQ ID NO 169
<211> LENGTH: 63
<212> TYPE: PRT
<213> ORGANISM: Pseudomonas thermotolerans

<400> SEQUENCE: 169

Met His Gln Thr Ala Leu Glu Arg Leu Asn Trp Asp Asp Leu Arg Phe
1               5                   10                  15
```

Phe Leu Glu Val Ala Arg Ser Gly Thr Ala Ser Gly Ala Ala Arg Arg
            20                  25                  30

Leu Gly Val Asp Tyr Thr Thr Val Ser Arg Arg Ile Arg Ala Leu Glu
        35                  40                  45

Gln Ala Leu Gly Ala Leu Leu Phe Glu Lys Ser Arg Ser Ala Gly
    50                  55                  60

<210> SEQ ID NO 170
<211> LENGTH: 63
<212> TYPE: PRT
<213> ORGANISM: Pseudomonas tolaasii

<400> SEQUENCE: 170

Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Val Ala Ala
            20                  25                  30

Lys Arg Leu Ala Val Asp Tyr Thr Thr Val Ser Arg Arg Ile Ser Ser
        35                  40                  45

Leu Glu Val Ser Leu Gly Thr Leu Leu Phe Glu Lys Ser Arg Thr
    50                  55                  60

<210> SEQ ID NO 171
<211> LENGTH: 63
<212> TYPE: PRT
<213> ORGANISM: Pseudomonas umsongensis

<400> SEQUENCE: 171

Met Gln Lys Asn Ile Thr Ser Leu Gly Ser Leu Asn Trp Asp Asp Leu
1               5                   10                  15

Lys Phe Phe Leu Glu Val Ala Arg Thr Arg Lys Ala Ser Thr Ala Ala
            20                  25                  30

Lys Arg Leu Ala Val Asp Tyr Thr Thr Val Ser Arg Arg Ile Ser Ser
        35                  40                  45

Leu Glu Thr Ser Leu Gly Thr Leu Leu Phe Glu Lys Ser Arg Thr
    50                  55                  60

<210> SEQ ID NO 172
<211> LENGTH: 63
<212> TYPE: PRT
<213> ORGANISM: Pseudomonas viridiflava

<400> SEQUENCE: 172

Met Gln Lys Asn Ile Thr Ser Leu Gly Leu Leu Asn Trp Asp Asp Leu
1               5                   10                  15

Lys Phe Phe Leu Glu Val Ala Arg Thr Arg Lys Val Ser Ser Ala Ala
            20                  25                  30

Lys Arg Leu Ala Val Asp Tyr Thr Thr Val Ser Arg Arg Ile Thr Ser
        35                  40                  45

Leu Glu Asn Ser Leu Gly Thr Leu Leu Phe Glu Lys Ser Arg Asn
    50                  55                  60

<210> SEQ ID NO 173
<211> LENGTH: 63
<212> TYPE: PRT
<213> ORGANISM: Pseudomonas vranovensis

<400> SEQUENCE: 173

Met Gln Lys Asn Ile Thr Ser Leu Gly Ser Leu Asn Trp Asp Asp Leu

```
            1               5                  10                 15
Lys Phe Phe Leu Glu Val Ala Arg Thr Arg Lys Ala Ser Ala Ala Ala
                    20                  25                  30

Lys Arg Leu Gly Val Asp Tyr Thr Thr Val Ser Arg Arg Ile Ser Ser
            35                  40                  45

Leu Glu Val Ser Leu Gly Thr Leu Leu Phe Glu Lys Ser Arg Thr
    50                  55                  60
```

<210> SEQ ID NO 174
<211> LENGTH: 63
<212> TYPE: PRT
<213> ORGANISM: Pseudomonas xanthomarina

<400> SEQUENCE: 174

```
Met Asp Trp Asp Asn Leu Arg Tyr Phe Leu Glu Val Ala Arg Ala Gly
1               5                  10                 15

Arg Leu Thr Thr Ala Ala Arg Arg Leu Ala Val Asp His Thr Thr Val
            20                  25                  30

Ser Arg Arg Leu Gln Ala Leu Glu Lys Ser Met Gly Leu Gln Leu Phe
            35                  40                  45

Leu Arg Glu Pro Gly Gly Tyr Lys Leu Thr Glu Ala Gly Arg Asn
    50                  55                  60
```

<210> SEQ ID NO 175
<211> LENGTH: 63
<212> TYPE: PRT
<213> ORGANISM: Pusillimonas sp.

<400> SEQUENCE: 175

```
Met Leu Asp Trp Asp Gly Leu Arg Tyr Phe Leu Glu Val Ala Arg Thr
1               5                  10                 15

Gln Arg Val Ser Ala Ala Ala Leu Arg Leu Gly Val Arg His Ser Thr
            20                  25                  30

Val Ser Arg Arg Ile His Ala Leu Glu Leu Glu Leu Gly Thr Leu Leu
            35                  40                  45

Phe Asp Lys Ser Lys Ser Thr Gly Phe Thr Leu Thr Glu Glu Gly
    50                  55                  60
```

<210> SEQ ID NO 176
<211> LENGTH: 70
<212> TYPE: PRT
<213> ORGANISM: Achromobacter sp.

<400> SEQUENCE: 176

```
Met Leu Asp Trp Asp Ser Leu Arg Tyr Phe Leu Glu Val Ala Arg Thr
1               5                  10                 15

Gln Arg Val Ser Ala Ala Ala Arg Lys Leu Gly Val Glu His Thr Thr
            20                  25                  30

Val Ser Arg Arg Ile Arg Ala Leu Glu Thr Glu Leu Asp Thr Leu Leu
            35                  40                  45

Phe Glu Lys Ser Arg Ser Ala Gly Phe Val Leu Thr Glu Asp Gly Gln
    50                  55                  60

Arg Leu Phe Val His Ala
65                  70
```

<210> SEQ ID NO 177
<211> LENGTH: 70
<212> TYPE: PRT
<213> ORGANISM: Acidovorax avenae

<400> SEQUENCE: 177

Met Asp Trp Glu Asn Leu Arg Tyr Phe Leu Glu Leu Ala Arg Thr Gly
1               5                   10                  15

Thr Leu Ala Ala Ala Ala Arg Arg Thr Gly Val Glu His Thr Thr Val
            20                  25                  30

Ala Arg Arg Ile Gln Ala Leu Glu Lys Gln Met Gly Glu Ser Leu Phe
        35                  40                  45

Ala Arg Glu Ala Gly Gly His Arg Leu Thr Glu Ala Gly Arg His Leu
    50                  55                  60

Leu Pro Ala Val Glu Ala
65                  70

<210> SEQ ID NO 178
<211> LENGTH: 70
<212> TYPE: PRT
<213> ORGANISM: Acidovorax citrulli

<400> SEQUENCE: 178

Met Asp Trp Glu Asn Leu Arg Tyr Phe Leu Glu Leu Ala Arg Thr Gly
1               5                   10                  15

Thr Leu Ala Ala Ala Ala Arg Arg Thr Gly Val Glu His Thr Thr Val
            20                  25                  30

Ala Arg Arg Ile Gln Ala Leu Glu Lys Gln Met Gly Glu Ser Leu Phe
        35                  40                  45

Ala Arg Glu Ala Gly Gly His Arg Leu Thr Glu Ala Gly Arg His Leu
    50                  55                  60

Leu Pro Ala Val Glu Ala
65                  70

<210> SEQ ID NO 179
<211> LENGTH: 70
<212> TYPE: PRT
<213> ORGANISM: Acidovorax delafieldii

<400> SEQUENCE: 179

Met Asp Trp Asp Asn Leu Arg Tyr Phe Leu Glu Leu Ala Arg Ala Gly
1               5                   10                  15

Thr Leu Val Gly Ala Ala Arg Arg Leu Ala Val Asp His Thr Thr Val
            20                  25                  30

Ala Arg Arg Ile Gln Ala Leu Glu Lys Gln Val Gly Ser Ala Leu Phe
        35                  40                  45

Ala Arg Glu Ala Gly Gly His Arg Leu Thr Glu Ala Gly Arg Val Leu
    50                  55                  60

Leu Pro Gln Val Glu Ala
65                  70

<210> SEQ ID NO 180
<211> LENGTH: 70
<212> TYPE: PRT
<213> ORGANISM: Acidovorax ebreus

<400> SEQUENCE: 180

Met Asp Trp Asp Asn Leu Arg Tyr Phe Leu Glu Leu Ala Arg Thr Gly
1               5                   10                  15

Thr Leu Ala Gly Ala Ala Arg Arg Thr Gly Val Glu His Thr Thr Val
            20                  25                  30

Ala Arg Arg Ile Gln Ala Leu Glu Lys Gln Met Gly Ala Pro Leu Phe

```
                    35                  40                  45
Ala Arg Glu Ala Ala Gly His Arg Leu Thr Glu Thr Gly Arg His Leu
            50                  55                  60

Leu Pro Ala Val Glu Ala
65                  70

<210> SEQ ID NO 181
<211> LENGTH: 71
<212> TYPE: PRT
<213> ORGANISM: Acinetobacter baumannii

<400> SEQUENCE: 181

Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Leu Ala Leu Gly Thr Thr
            35                  40                  45

Leu Phe Lys Arg Glu Ala Thr Gly Tyr Glu Leu Thr Leu Glu Gly Met
            50                  55                  60

Ala Leu Val Pro Arg Val Glu
65                  70

<210> SEQ ID NO 182
<211> LENGTH: 71
<212> TYPE: PRT
<213> ORGANISM: Acinetobacter guillouiae

<400> SEQUENCE: 182

Met Lys Val Asp Trp Asp His Leu Gln Phe Phe Leu Val Leu Ala Arg
1               5                   10                  15

Ala Lys Thr Leu Thr Asn Ala Ala Arg Ile Ile Gly Val Glu His Ser
            20                  25                  30

Thr Val Ser Arg Arg Ile Gln Ala Leu Glu Leu Ala Leu Gly Thr Pro
            35                  40                  45

Leu Phe Arg Arg Glu Ala Thr Gly Tyr Glu Leu Thr Met Glu Gly Leu
            50                  55                  60

Ala Leu Val Pro Arg Val Glu
65                  70

<210> SEQ ID NO 183
<211> LENGTH: 70
<212> TYPE: PRT
<213> ORGANISM: Acinetobacter gyllenbergii

<400> SEQUENCE: 183

Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Gln Ala Leu Gly Val Thr
            35                  40                  45

Leu Phe Lys Arg Glu Ala Ser Gly Tyr Glu Leu Thr Leu Glu Gly Met
            50                  55                  60

Ala Leu Val Pro Arg Val
65                  70

<210> SEQ ID NO 184
```

```
<211> LENGTH: 70
<212> TYPE: PRT
<213> ORGANISM: Acinetobacter johnsonii

<400> SEQUENCE: 184

Met Lys Val Asp Trp Asp His Leu Gln Phe Phe Leu Val Leu Ala Arg
1               5                   10                  15

Ala Lys Thr Leu Thr Asn Ala Ala Arg Ile Ile Gly Val Glu His Ser
            20                  25                  30

Thr Val Ala Arg Arg Val Gln Ser Leu Glu Val Ala Leu Gly Thr Pro
        35                  40                  45

Leu Phe Lys Arg Glu Ala Thr Gly Tyr Glu Leu Thr Val Asp Gly Met
    50                  55                  60

Ala Leu Val Pro Arg Val
65                  70

<210> SEQ ID NO 185
<211> LENGTH: 70
<212> TYPE: PRT
<213> ORGANISM: Acinetobacter junii

<400> SEQUENCE: 185

Met Lys Val Asp Trp Asp His Leu Gln Phe Phe Leu Val Leu Ala Arg
1               5                   10                  15

Thr Lys Thr Leu Thr Asn Ala Ala Arg Ile Ile Gly Val Glu His Ser
            20                  25                  30

Thr Val Ala Arg Arg Ile Gln Ala Leu Glu Leu Ala Leu Gly Thr Thr
        35                  40                  45

Leu Phe Lys Arg Glu Ala Ser Gly Tyr Glu Leu Thr Met Glu Gly Leu
    50                  55                  60

Ala Leu Val Pro Gln Val
65                  70

<210> SEQ ID NO 186
<211> LENGTH: 71
<212> TYPE: PRT
<213> ORGANISM: Acinetobacter soli

<400> SEQUENCE: 186

Met Lys Val Asp Trp Asp His Leu Arg Phe Phe Leu Val Leu Ala Arg
1               5                   10                  15

Ala Lys Thr Leu Thr Asn Ala Ala Arg Leu Ile Gly Val Glu His Ser
            20                  25                  30

Thr Val Ala Arg Arg Ile Gln Ala Leu Glu Ser Thr Leu Gly Thr Gln
        35                  40                  45

Leu Phe Lys Arg Glu Ala Thr Gly Tyr Glu Leu Thr Ser Glu Gly Leu
    50                  55                  60

Ala Leu Val Pro Arg Val Glu
65                  70

<210> SEQ ID NO 187
<211> LENGTH: 70
<212> TYPE: PRT
<213> ORGANISM: Advenella kashmirensis

<400> SEQUENCE: 187

Met Pro Asp Trp Asp Asp Ile Arg Tyr Phe Leu Glu Val Ala Arg Thr
1               5                   10                  15

His Arg Ala Ser Ala Ala Ala Ala Arg Leu Gly Val Glu His Thr Thr
```

```
                    20                  25                  30

Val Thr Arg Arg Ile Arg His Leu Glu Ala Asp Leu Gly Gln Leu Leu
            35                  40                  45

Phe Glu Lys Ser Arg Arg Ser Gly Phe Thr Leu Thr Arg Ser Gly Gln
    50                  55                  60

Gln Leu Leu Ala His Ala
65                  70

<210> SEQ ID NO 188
<211> LENGTH: 70
<212> TYPE: PRT
<213> ORGANISM: Afipia birgiae

<400> SEQUENCE: 188

Met Thr Asp Gln Phe Asp Trp Asn Leu Val Arg Ser Phe Leu Ala Ile
1               5                   10                  15

Thr Arg Ser Gly Ser Met Thr Ala Ala Lys Arg Leu Lys Ile Asp
            20                  25                  30

Tyr Ser Thr Leu Ser Arg Arg Ile Ala Ala Leu Glu Ala Ser Leu Gly
            35                  40                  45

Ser Gln Leu Phe Asp Arg Arg Thr Ser Gly Ser Ser Leu Thr Glu Ala
    50                  55                  60

Gly Asp Arg Leu Leu Glu
65                  70

<210> SEQ ID NO 189
<211> LENGTH: 70
<212> TYPE: PRT
<213> ORGANISM: Afipia broomeae

<400> SEQUENCE: 189

Met Thr Asp Gln Phe Asp Trp Asn Leu Val Arg Ser Phe Leu Ala Ile
1               5                   10                  15

Thr Arg Thr Gly Ser Met Thr Ala Ala Lys Arg Leu Lys Ile Asp
            20                  25                  30

Tyr Ser Thr Leu Ser Arg Arg Ile Ala Ala Leu Glu Thr Ser Leu Gly
            35                  40                  45

Ser Gln Leu Phe Asp Arg Arg Thr Ser Gly Ser Ser Leu Thr Glu Ala
    50                  55                  60

Gly Glu Arg Leu Leu Glu
65                  70

<210> SEQ ID NO 190
<211> LENGTH: 70
<212> TYPE: PRT
<213> ORGANISM: Agrobacterium tumefaciens

<400> SEQUENCE: 190

Met Asn Trp Asp Asp Val Arg Leu Phe Leu Ser Val Ala Arg Ser Gly
1               5                   10                  15

Gln Phe Leu Ser Ala Ala Arg Lys Leu Gly Val Asn His Ala Thr Leu
            20                  25                  30

Ser Arg Arg Ile Ser Ala Leu Glu Ala Ala Ile Gly Thr Gln Leu Phe
            35                  40                  45

Leu Arg Ser Thr Asn Gly Cys Glu Leu Thr Glu Glu Gly Gln Arg Leu
    50                  55                  60

Leu Ala Gly Ala Glu His
65                  70
```

<210> SEQ ID NO 191
<211> LENGTH: 70
<212> TYPE: PRT
<213> ORGANISM: Alcaligenes faecalis

<400> SEQUENCE: 191

Met Asp Trp Asp Asn Leu Arg Tyr Phe Leu Glu Val Ala Arg Cys Gln
1               5                   10                  15

Arg Ile Ser Val Ala Ala Gln Arg Leu Gly Val Gln His Ser Thr Val
            20                  25                  30

Ala Arg Arg Ile Gln Ala Leu Glu Gln Glu Leu Gly Leu Arg Leu Phe
        35                  40                  45

His Lys Ser Thr Val Ser Gly Tyr Ser Leu Thr Ser Glu Gly Gln Asn
    50                  55                  60

Leu Gln Gln Arg Met Glu
65                  70

<210> SEQ ID NO 192
<211> LENGTH: 70
<212> TYPE: PRT
<213> ORGANISM: Alicycliphilus denitrificans

<400> SEQUENCE: 192

Met Asp Trp Asp Asn Leu Arg Tyr Phe Leu Glu Leu Ala Arg Thr Gly
1               5                   10                  15

Thr Leu Ala Ala Ala Ala Arg Arg Thr Gly Val Glu His Thr Thr Val
            20                  25                  30

Ala Arg Arg Ile Gln Ala Leu Glu Lys Gln Met Gly Ala Pro Leu Phe
        35                  40                  45

Ala Arg Glu Ala Ala Gly His Arg Leu Thr Glu Ala Gly Arg His Leu
    50                  55                  60

Leu Pro Ala Val Glu Ala
65                  70

<210> SEQ ID NO 193
<211> LENGTH: 70
<212> TYPE: PRT
<213> ORGANISM: Azorhizobium caulinodans

<400> SEQUENCE: 193

Ala Val Thr Gly Ala Asp Phe Glu Trp Ser Asp Leu Arg Tyr Leu Leu
1               5                   10                  15

Thr Val Ala Arg Ser Gly Ser Leu Thr Ala Ala Ala Arg Gln Met Gly
            20                  25                  30

Val Glu His Ser Thr Val Ser Arg Arg Ile Thr Ala Leu Glu Thr Ala
        35                  40                  45

Leu Gly Ala Lys Leu Phe Asp Arg Arg Thr Gly Leu Leu Leu Thr
    50                  55                  60

Pro Gln Gly Glu Arg Leu
65                  70

<210> SEQ ID NO 194
<211> LENGTH: 70
<212> TYPE: PRT
<213> ORGANISM: Azospirillum lipoferum

<400> SEQUENCE: 194

Met Ala Asp Phe Asn Trp Asn Asp Leu Arg Phe Phe Leu Ala Val Ala

```
                1               5                  10                 15
Arg Ala Gly Thr Leu Thr Thr Ala Ala Gln Arg Leu Arg Ala Asp His
                20                 25                 30

Thr Thr Val Ser Arg Arg Ile Ser Ala Leu Glu Asp Ala Leu Arg Val
        35                 40                 45

Thr Leu Phe Glu Arg Arg Pro Ser Gly Phe Thr Leu Thr Pro Gln Gly
    50                 55                 60

Glu Arg Leu Lys Gln Thr
65                  70

<210> SEQ ID NO 195
<211> LENGTH: 70
<212> TYPE: PRT
<213> ORGANISM: Azospirillum sp.

<400> SEQUENCE: 195

Met Ala Asp Phe Asn Trp Asn Asp Leu Arg Phe Phe Leu Ala Val Ala
1               5                  10                 15

Arg Ala Gly Thr Leu Thr Thr Ala Ala Gln Arg Leu Arg Ala Asp His
                20                 25                 30

Thr Thr Val Ser Arg Arg Ile Thr Ala Leu Glu Asp Ala Leu Arg Val
        35                 40                 45

Thr Leu Phe Glu Arg Arg Pro Ser Gly Phe Thr Leu Thr Pro Gln Gly
    50                 55                 60

Glu Arg Leu Lys Gln Thr
65                  70

<210> SEQ ID NO 196
<211> LENGTH: 70
<212> TYPE: PRT
<213> ORGANISM: Bordetella hinzii

<400> SEQUENCE: 196

Met Leu Asp Trp Asp Ser Leu Arg Tyr Phe Leu Glu Val Ala Arg Ser
1               5                  10                 15

Gln Arg Val Ser Ala Ala Ala Arg Thr Leu Gly Val Glu His Thr Thr
                20                 25                 30

Val Ala Arg Arg Ile Arg Ala Leu Glu Ala Glu Leu Gly Ser Leu Leu
        35                 40                 45

Phe Glu Lys Ser Arg Ser Ala Gly Phe Val Leu Thr Glu Asp Gly Gln
    50                 55                 60

Arg Leu Phe Val Tyr Ala
65                  70

<210> SEQ ID NO 197
<211> LENGTH: 70
<212> TYPE: PRT
<213> ORGANISM: Bordetella petrii

<400> SEQUENCE: 197

Met Leu Asp Trp Asp Ser Leu Arg Tyr Phe Leu Glu Val Ala Arg Thr
1               5                  10                 15

Gln Arg Val Ser Ala Ala Ala Arg Arg Leu Gly Val Glu His Thr Thr
                20                 25                 30

Val Ala Arg Arg Ile Arg Ala Leu Glu Ala Glu Leu Asp Ser Leu Leu
        35                 40                 45

Phe Glu Lys Ser Arg Ser Thr Gly Phe Val Leu Thr Glu Asp Gly Gln
    50                 55                 60
```

Arg Leu Phe Val Tyr Ala
65                  70

<210> SEQ ID NO 198
<211> LENGTH: 70
<212> TYPE: PRT
<213> ORGANISM: Bordetella trematum

<400> SEQUENCE: 198

Met Leu Asp Trp Asp Ser Leu Arg Tyr Phe Leu Glu Val Ala Arg Ser
1               5                   10                  15

Gln Arg Val Ser Ala Ala Ala Arg Thr Leu Gly Val Glu His Thr Thr
            20                  25                  30

Val Ala Arg Arg Val Arg Ala Leu Glu Ala Glu Leu Gly Ser Leu Leu
        35                  40                  45

Phe Glu Lys Ser Arg Ser Ala Gly Phe Val Leu Thr Glu Asp Gly Gln
    50                  55                  60

Arg Leu Leu Val Tyr Ala
65                  70

<210> SEQ ID NO 199
<211> LENGTH: 70
<212> TYPE: PRT
<213> ORGANISM: Bosea sp.

<400> SEQUENCE: 199

Met Glu Arg Phe Asp Trp Asp Asp Leu Arg Phe Phe Leu Ala Val Ala
1               5                   10                  15

Arg Ser Gly Arg Leu Thr Ala Ala Ala Arg Arg Leu Gly Ala Asp His
            20                  25                  30

Ala Thr Val Ser Arg Arg Ile Thr Ser Leu Glu Glu Ala Leu Lys Ala
        35                  40                  45

Lys Leu Phe Glu Arg Arg Pro Gln Gly Tyr Thr Leu Thr Ala His Gly
    50                  55                  60

Glu Arg Leu Leu Ala Lys
65                  70

<210> SEQ ID NO 200
<211> LENGTH: 70
<212> TYPE: PRT
<213> ORGANISM: Bradyrhizobium yuanmingense

<400> SEQUENCE: 200

Met Leu Asp Gln Gly Ala Ile Asp Trp Asp Asp Phe Arg Phe Val Leu
1               5                   10                  15

Ala Ile Val Arg Gly Gly Ser Val Ser Ala Ala Lys Gln Leu Gly
            20                  25                  30

Val Asp His Ala Thr Val Ile Arg Arg Val Asp Arg Leu Glu Lys His
        35                  40                  45

Leu Ser Ala Lys Leu Phe Asp Arg Arg Lys Thr Gly Tyr Leu Leu Thr
    50                  55                  60

Glu Ala Gly Gln Arg Val
65                  70

<210> SEQ ID NO 201
<211> LENGTH: 70
<212> TYPE: PRT
<213> ORGANISM: Brucella abortus

```
<400> SEQUENCE: 201

Arg Trp Met Arg Pro Phe Thr Trp Asp Asp Leu Gln Tyr Phe Leu Ala
1               5                   10                  15

Val Ala Arg Thr Gly Gln Leu Ser Thr Ala Ala Arg Gln Leu Arg Thr
            20                  25                  30

Ser His Val Thr Val Leu Arg Arg Ile Asp Arg Leu Glu Gln Ala Leu
        35                  40                  45

Ser Thr Lys Leu Phe Glu Arg Asn Pro Arg Gly Tyr Leu Leu Thr Pro
    50                  55                  60

Met Gly Glu Arg Leu Val
65                  70

<210> SEQ ID NO 202
<211> LENGTH: 70
<212> TYPE: PRT
<213> ORGANISM: Brucella inopinata

<400> SEQUENCE: 202

Gln Ala Lys Asn Ala Met Asn Trp Asp Asp Ile Arg Ile Phe Leu Ala
1               5                   10                  15

Val Ala Arg Ser Gly Gln Ile Leu Gly Ala Ala Arg Gln Leu Gly Leu
            20                  25                  30

Asn His Thr Thr Val Ala Arg Arg Leu Thr Ala Leu Glu Thr Ala Leu
        35                  40                  45

Ser Thr Thr Leu Leu Thr Arg Arg Thr Asn Gly Ser Thr Leu Thr His
    50                  55                  60

Ala Gly Glu Glu Phe Leu
65                  70

<210> SEQ ID NO 203
<211> LENGTH: 71
<212> TYPE: PRT
<213> ORGANISM: Brucella melit

```
Ser Thr Lys Leu Phe Glu Arg Asn Pro Arg Gly Tyr Leu Leu Thr Pro
 50                  55                  60

Met Gly Glu Arg Leu Val
 65                  70

<210> SEQ ID NO 205
<211> LENGTH: 70
<212> TYPE: PRT
<213> ORGANISM: Brucella ovis

<400> SEQUENCE: 205

Gln Ala Lys Asn Ala Met Asn Trp Asp Asp Ile Arg Ile Phe Leu Ala
 1               5                  10                  15

Val Ala Arg Ser Gly Gln Ile Leu Gly Ala Ala Arg Arg Leu Gly Leu
             20                  25                  30

Asn His Thr Thr Val Ala Arg Arg Leu Thr Ala Leu Glu Thr Ala Leu
         35                  40                  45

Ser Thr Thr Leu Leu Thr Arg Arg Thr Asn Gly Ser Thr Leu Thr His
 50                  55                  60

Ala Gly Glu Glu Phe Leu
 65                  70

<210> SEQ ID NO 206
<211> LENGTH: 70
<212> TYPE: PRT
<213> ORGANISM: Brucella pinnipedialis

<400> SEQUENCE: 206

Met Pro Ala Gln Ala Lys Asn Ala Met Asn Trp Asp Asp Ile Arg Ile
 1               5                  10                  15

Phe Leu Ala Val Ala Arg Ser Gly Gln Ile Leu Gly Ala Ala Arg Arg
             20                  25                  30

Leu Gly Leu Asn His Thr Thr Val Ala Arg Arg Leu Thr Ala Leu Glu
         35                  40                  45

Thr Ala Leu Ser Thr Thr Leu Leu Thr Arg Arg Thr Asn Gly Ser Thr
 50                  55                  60

Leu Thr His Ala Gly Glu
 65                  70

<210> SEQ ID NO 207
<211> LENGTH: 70
<212> TYPE: PRT
<213> ORGANISM: Brucella sp.

<400> SEQUENCE: 207

Gln Ala Lys Asn Ala Met Asn Trp Asp Asp Ile Arg Ile Phe Leu Ala
 1               5                  10                  15

Val Ala Arg Ser Gly Gln Ile Leu Gly Ala Ala Arg Arg Leu Gly Leu
             20                  25                  30

Asn His Thr Thr Val Ala Arg Arg Leu Thr Ala Leu Glu Thr Ala Leu
         35                  40                  45

Ser Thr Thr Leu Leu Thr Arg Arg Thr Asn Gly Ser Thr Leu Thr His
 50                  55                  60

Ala Gly Glu Glu Phe Leu
 65                  70

<210> SEQ ID NO 208
<211> LENGTH: 70
```

```
<212> TYPE: PRT
<213> ORGANISM: Brucella suis

<400> SEQUENCE: 208

Met Asn Trp Asp Asp Ile Arg Ile Ph

```
Val Ala Arg Arg Val Arg Glu Leu Glu Ala Ala Leu Gly Thr Val Leu
            35                  40                  45

Phe Asp Lys Ser Arg Ser Gly Gly Phe Val Leu Thr Thr Glu Gly Gln
 50                  55                  60

Arg Leu Leu Ala Tyr Ala
 65                  70

<210> SEQ ID NO 212
<211> LENGTH: 70
<212> TYPE: PRT
<213> ORGANISM: Collimonas arenae

<400> SEQUENCE: 212

Thr Asn Ala Met Leu Asp Trp Asp Asn Leu Arg Val Phe Leu Glu Leu
 1               5                  10                  15

Thr Arg Ser Gln Gly Leu Val Glu Ala Ala Lys Lys Leu Gly Ile Asp
            20                  25                  30

His Ser Thr Val Ser Arg Arg Met Arg Arg Phe Glu Glu Gln Val Gly
            35                  40                  45

Ser Gln Leu Phe Glu Arg Asn Asn Gln Gly Tyr Thr Leu Thr Ala Glu
 50                  55                  60

Gly His Arg Leu Ile Glu
 65                  70

<210> SEQ ID NO 213
<211> LENGTH: 70
<212> TYPE: PRT
<213> ORGANISM: Collimonas fungivorans

<400> SEQUENCE: 213

Thr Lys Ala Met Leu Asp Trp Asp Asn Leu Arg Val Phe Leu Glu Leu
 1               5                  10                  15

Thr Arg Ser Gln Gly Leu Val Glu Thr Ala Lys Lys Leu Gly Ile Asp
            20                  25                  30

His Ser Thr Val Ser Arg Arg Met His Arg Phe Glu Glu Gln Val Gly
            35                  40                  45

Ser Gln Leu Phe Glu Arg Asn Asn Gln Gly Tyr Thr Leu Thr Ala Glu
 50                  55                  60

Gly His Arg Leu Ile Glu
 65                  70

<210> SEQ ID NO 214
<211> LENGTH: 70
<212> TYPE: PRT
<213> ORGANISM: Polynucleobacter necessarius

<400> SEQUENCE: 214

Met Asn Ser Met Asn Trp Asp His Leu Gln Tyr Phe Leu Ala Leu Ala
 1               5                  10                  15

Lys Asp Gly Arg Leu Ile Val Ala Ala Arg Ser Leu Gly Val Asn His
            20                  25                  30

Thr Thr Val Ser Arg Arg Ile Gln Ala Leu Glu Arg Glu Met Gly Val
            35                  40                  45

Gln Leu Phe Ser Arg Asn Asn Leu Gly Phe Glu Leu Thr Glu Ala Gly
 50                  55                  60

Met Gln Leu Gln Asn Ile
 65                  70
```

<210> SEQ ID NO 215
<211> LENGTH: 70
<212> TYPE: PRT
<213> ORGANISM: Pseudogulbenkiania sp.

<400> SEQUENCE: 215

Leu Asn Trp Asp Asp Ile Lys Phe Phe Leu Glu Val Ala Arg Thr His
1               5                   10                  15

Thr Ala Ser Ser Ala Ala Lys Arg Leu Gly Val Asp Tyr Thr Thr Val
            20                  25                  30

Ser Arg Arg Ile Arg Ala Leu Glu Gln Ala Leu Gly Ala Leu Leu Phe
        35                  40                  45

Glu Lys Ser Arg Ser Ala Gly Phe Val Leu Thr Val Asp Gly Gln Gln
    50                  55                  60

Leu Leu Arg Tyr Ala Glu
65                  70

<210> SEQ ID NO 216
<211> LENGTH: 70
<212> TYPE: PRT
<213> ORGANISM: Pseudomonas aeruginosa

<400> SEQUENCE: 216

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Gly Thr Thr His Ala Thr
            20                  25                  30

Val Ala Arg His Ile Glu Asn Ile Glu Arg Asp Leu Gly Thr Gln Leu
        35                  40                  45

Phe Ala Gln His Thr Gly Gly Tyr Gln Leu Thr Pro Ala Gly Gln Ala
    50                  55                  60

Leu Leu Lys His Ala Glu
65                  70

<210> SEQ ID NO 217
<211> LENGTH: 70
<212> TYPE: PRT
<213> ORGANISM: Pseudomonas agarici

<400> SEQUENCE: 217

Met Phe Asp Trp Asn Asp Leu Arg Phe Phe Leu Glu Leu Gln Arg Ser
1               5                   10                  15

Gly Arg Leu Leu Ser Ala Ala Lys Arg Leu Asn Thr Thr His Ser Thr
            20                  25                  30

Val Ala Arg His Ile Glu Thr Ile Glu Arg Asn Leu Gly Thr Ala Leu
        35                  40                  45

Phe Val Gln His Ala Gln Gly Tyr Glu Leu Thr Pro Ser Gly Gln Ala
    50                  55                  60

Leu Leu Lys His Ala Glu
65                  70

<210> SEQ ID NO 218
<211> LENGTH: 70
<212> TYPE: PRT
<213> ORGANISM: Pseudomonas alkylphenolia

<400> SEQUENCE: 218

Met Phe Asp Trp Asn Asp Leu Arg Phe Phe Leu Glu Leu Gln Arg Ser
1               5                   10                  15

```
Gly Arg Leu Leu Thr Ala Ala Lys Arg Leu Asn Thr Thr His Ser Thr
            20                  25                  30

Val Ala Arg His Ile Asp Asn Ile Glu Gln Ser Leu Gly Thr Ala Leu
            35                  40                  45

Phe Val Gln His Ala Gln Gly Tyr Glu Leu Thr Pro Ser Gly Gln Ala
    50                  55                  60

Leu Leu Lys His Ala Glu
65              70

<210> SEQ ID NO 219
<211> LENGTH: 70
<212> TYPE: PRT
<213> ORGANISM: Pseudomonas batumici

<400> SEQUENCE: 219

Leu Asn Trp Asp Asp Leu Lys Phe Phe Leu Glu Val Ala Arg Thr Arg
1               5                   10                  15

Lys Ala Ser Ser Ala Ala Lys Arg Leu Ala Val Asp Tyr Thr Thr Val
            20                  25                  30

Ser Arg Arg Ile Ser Ser Leu Glu Gly Ala Leu Gly Thr Leu Leu Phe
            35                  40                  45

Glu Lys Ser Arg Thr Asn Gly Phe Val Leu Thr Ala Glu Gly Gln Arg
    50                  55                  60

Leu Met Gly Tyr Ala Glu
65              70

<210> SEQ ID NO 220
<211> LENGTH: 70
<212> TYPE: PRT
<213> ORGANISM: Pseudomonas brassicacearum

<400> SEQUENCE: 220

Met Phe Asp Trp Asn Asp Leu Arg Tyr Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Ile Glu Lys Ser Leu Gly Ser Ala Leu
            35                  40                  45

Phe Val Gln His Ala Gln Gly Tyr Glu Leu Thr Pro Ala Gly Glu Thr
    50                  55                  60

Leu Leu Lys His Ala Glu
65              70

<210> SEQ ID NO 221
<211> LENGTH: 70
<212> TYPE: PRT
<213> ORGANISM: Pseudomonas chloritidismutans

<400> SEQUENCE: 221

Met Asp Trp Asp Asn Leu Arg Tyr Phe Leu Glu Val Ala Arg Ala Gly
1               5                   10                  15

Arg Leu Thr Thr Ala Ala Arg Arg Leu Ala Val Asp His Thr Thr Val
            20                  25                  30

Ser Arg Arg Leu Gln Ala Leu Glu Lys Ser Met Gly Leu Gln Leu Phe
            35                  40                  45

Leu Arg Glu Pro Gly Gly Tyr Lys Leu Thr Glu Ala Gly Cys Asn Leu
    50                  55                  60
```

-continued

Leu Pro Arg Val Glu Ala
65                  70

<210> SEQ ID NO 222
<211> LENGTH: 70
<212> TYPE: PRT
<213> ORGANISM: Pseudomonas chlororaphis

<400> SEQUENCE: 222

Met Phe Asp Trp Asn Asp Leu Arg Phe Phe Leu Glu Leu Gln Arg Ser
1               5                   10                  15

Gly Arg Leu Leu Thr Ala Ala Gln Arg Leu Lys Thr Thr His Ala Thr
            20                  25                  30

Val Ala Arg His Ile Glu Glu Ile Glu Lys Ser Leu Gly Thr Ala Leu
        35                  40                  45

Phe Ile Gln His Ala Gln Gly Tyr Glu Leu Thr Pro Ala Gly Glu Ala
    50                  55                  60

Leu Leu Lys His Ala Glu
65                  70

<210> SEQ ID NO 223
<211> LENGTH: 70
<212> TYPE: PRT
<213> ORGANISM: Pseudomonas corrugata

<400> SEQUENCE: 223

Met Phe Asp Trp Asn Asp Leu Arg Tyr Phe Leu Glu Leu Gln Arg Ser
1               5                   10                  15

Gly Arg Leu Leu Ser Ala Ala Arg Arg Leu Asn Thr Thr His Ala Thr
            20                  25                  30

Val Ala Arg His Ile Glu Ala Ile Glu Lys Ser Leu Gly Thr Ala Leu
        35                  40                  45

Phe Ile Gln His Ala Gln Gly Tyr Glu Leu Thr Pro Ala Gly Glu Thr
    50                  55                  60

Leu Leu Lys His Ala Glu
65                  70

<210> SEQ ID NO 224
<211> LENGTH: 70
<212> TYPE: PRT
<213> ORGANISM: Pseudomonas cremoricolorata

<400> SEQUENCE: 224

Met Phe Asp Trp Asn Asp Leu Arg Phe Phe Leu Glu Leu Gln Arg Ser
1               5                   10                  15

Gly Arg Leu Leu Ser Ala Gly Arg Arg Leu Lys Thr Thr His Ser Thr
            20                  25                  30

Val Ala Arg His Ile Glu Arg Ile Glu Ala Ser Leu Gly Thr Ala Leu
        35                  40                  45

Phe Ile His His Ala Gln Gly Phe Glu Leu Thr Pro Ala Gly Gln Ala
    50                  55                  60

Leu Leu Lys His Ala Glu
65                  70

<210> SEQ ID NO 225
<211> LENGTH: 70
<212> TYPE: PRT
<213> ORGANISM: Pseudomonas denitrificans

<400> SEQUENCE: 225

```
Met Phe Asp Trp Asn Asp Leu Arg Tyr Phe Leu Glu Leu His Arg Ser
1               5                   10                  15

Gly Arg Leu Leu Thr Thr Ala Lys Arg Leu Asn Thr Thr His Ala Thr
            20                  25                  30

Val Ala Arg His Ile Glu Asn Ile Glu Arg Asp Leu Gly Thr Gln Leu
            35                  40                  45

Phe Ala Gln His Thr Gly Gly Tyr Gln Leu Thr Pro Ala Gly Gln Ala
        50                  55                  60

Leu Leu Lys His Ala Glu
65                  70

<210> SEQ ID NO 226
<211> LENGTH: 70
<212> TYPE: PRT
<213> ORGANISM: Pseudomonas extremaustralis

<400> SEQUENCE: 226

Met Phe Asp Trp Asn Asp Leu Arg Tyr Phe Leu Glu Leu Gln Arg Ser
1               5                   10                  15

Gly Arg Leu Leu Thr Ala Ala Gln Arg Leu Lys Thr Thr His Ala Thr
            20                  25                  30

Val Ala Arg His Ile Asp Ala Ile Glu Lys Ser Leu Gly Thr Ala Leu
            35                  40                  45

Phe Val Gln His Ala Gln Gly Tyr Glu Leu Thr Pro Ala Gly Glu Ala
        50                  55                  60

Leu Leu Lys His Ala Glu
65                  70

<210> SEQ ID NO 227
<211> LENGTH: 70
<212> TYPE: PRT
<213> ORGANISM: Pseudomonas fluorescens

<400> SEQUENCE: 227

Met Phe Asp Trp Asn Asp Leu Arg Phe Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Ile Glu Lys Ser Leu Gly Thr Ala Leu
            35                  40                  45

Phe Val Gln His Ala Gln Gly Tyr Glu Met Thr Pro Ala Gly Glu Ala
        50                  55                  60

Leu Leu Lys His Ala Glu
65                  70

<210> SEQ ID NO 228
<211> LENGTH: 70
<212> TYPE: PRT
<213> ORGANISM: Pseudomonas frederiksbergensis

<400> SEQUENCE: 228

Met Phe Asp Trp Asn Asp Leu Arg Tyr Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Ile Glu Lys Ser Leu Gly Thr Ala Leu
            35                  40                  45
```

-continued

Phe Val Gln His Ala Gln Gly Tyr Glu Leu Thr Pro Ala Gly Glu Thr
    50                  55                  60

Leu Leu Lys His Ala Glu
65                  70

<210> SEQ ID NO 229
<211> LENGTH: 70
<212> TYPE: PRT
<213> ORGANISM: Pseudomonas fuscovaginae

<400> SEQUENCE: 229

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Thr Ile Glu Gln Ser Leu Gly Thr Ala Leu
        35                  40                  45

Phe Ile Gln His Ala Gln Gly Tyr Glu Leu Thr Pro Ala Gly Gln Ala
    50                  55                  60

Leu Leu Lys His Ala Glu
65                  70

<210> SEQ ID NO 230
<211> LENGTH: 70
<212> TYPE: PRT
<213> ORGANISM: Pseudomonas japonica

<400> SEQUENCE: 230

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Asn Ile Glu Gln Ser Leu Gly Thr Ala Leu
        35                  40                  45

Phe Val Gln His Ala Gln Gly Tyr Glu Leu Thr Pro Ser Gly Gln Ala
    50                  55                  60

Leu Leu Lys His Ala Glu
65                  70

<210> SEQ ID NO 231
<211> LENGTH: 70
<212> TYPE: PRT
<213> ORGANISM: Pseudomonas knackmussii

<400> SEQUENCE: 231

Met Phe Asp Trp Asn Asp Leu Arg Tyr Leu Leu Glu Leu His Arg Ser
1               5                   10                  15

Gly Arg Leu Leu Thr Ala Ala Lys Arg Leu Asn Thr Thr His Ala Thr
            20                  25                  30

Val Ala Arg His Ile Glu Ala Ile Glu Arg Asp Leu Gly Thr Gln Leu
        35                  40                  45

Phe Ala Gln His Thr Gly Gly Tyr Gln Leu Thr Pro Ala Gly Leu Ala
    50                  55                  60

Leu Leu Lys His Ala Glu
65                  70

<210> SEQ ID NO 232
<211> LENGTH: 70
<212> TYPE: PRT

<213> ORGANISM: Pseudomonas luteola

<400> SEQUENCE: 232

Met Phe Asn Trp Asp Asp Leu Arg Phe Phe Leu Glu Leu Gln Arg Ser
1               5                   10                  15

Gly Arg Leu Leu Ser Ala Ala Arg Arg Met Gly Thr Ser His Thr Thr
            20                  25                  30

Val Ala Arg His Ile Glu Ser Leu Glu Arg Thr Leu Gly Thr Gln Leu
        35                  40                  45

Leu Val Gln His Thr Gln Gly Tyr Gln Leu Thr Pro Ala Gly Gln Ala
    50                  55                  60

Leu Leu Lys His Ala Glu
65                  70

<210> SEQ ID NO 233
<211> LENGTH: 70
<212> TYPE: PRT
<213> ORGANISM: Pseudomonas mediterranea

<400> SEQUENCE: 233

Met Phe Asp Trp Asn Asp Leu Arg Tyr Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Ile Glu Lys Ser Leu Gly Thr Ala Leu
        35                  40                  45

Phe Ile Gln His Ala Gly Gly Tyr Glu Leu Thr Pro Ala Gly Glu Thr
    50                  55                  60

Leu Leu Lys His Ala Glu
65                  70

<210> SEQ ID NO 234
<211> LENGTH: 70
<212> TYPE: PRT
<213> ORGANISM: Pseudomonas nitroreducens

<400> SEQUENCE: 234

Met Phe Asp Trp Asn Asp Leu Arg Tyr Phe Leu Glu Leu His Arg Ser
1               5                   10                  15

Gly Arg Leu Leu Thr Thr Ala Lys Arg Leu Gly Thr Thr His Ala Thr
            20                  25                  30

Val Ala Arg His Ile Glu Ser Ile Glu Arg Asp Leu Gly Thr Gln Leu
        35                  40                  45

Phe Ala Gln His Thr Gly Gly Tyr Gln Leu Thr Pro Ala Gly Gln Ala
    50                  55                  60

Leu Leu Lys His Ala Glu
65                  70

<210> SEQ ID NO 235
<211> LENGTH: 70
<212> TYPE: PRT
<213> ORGANISM: Pseudomonas parafulva

<400> SEQUENCE: 235

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Asn Ile Glu Gln Ser Leu Gly Thr Ala Leu
            35                  40                  45

Phe Val Gln His Ala Gln Gly Tyr Glu Leu Thr Pro Ser Gly His Ala
        50                  55                  60

Leu Leu Lys His Ala Glu
65                  70

<210> SEQ ID NO 236
<211> LENGTH: 70
<212> TYPE: PRT
<213> ORGANISM: Pseudomonas plecoglossicida

<400> SEQUENCE: 236

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Ser Ile Glu Lys Ser Leu Gly Thr Pro Leu
            35                  40                  45

Phe Met Gln His Ala Gln Gly Tyr Glu Leu Thr Pro Ser Gly Gln Ala
        50                  55                  60

Leu Leu Lys His Ala Glu
65                  70

<210> SEQ ID NO 237
<211> LENGTH: 70
<212> TYPE: PRT
<213> ORGANISM: Pseudomonas protegens

<400> SEQUENCE: 237

Met Phe Asp Trp Asn Asp Leu Arg Phe Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Val Glu Lys Ala Leu Gly Thr Ala Leu
            35                  40                  45

Phe Val Gln His Ala Gln Gly Tyr Glu Leu Thr Pro Ala Gly Glu Ala
        50                  55                  60

Leu Leu Lys His Ala Glu
65                  70

<210> SEQ ID NO 238
<211> LENGTH: 70
<212> TYPE: PRT
<213> ORGANISM: Pseudomonas psychrophila

<400> SEQUENCE: 238

Met Phe Asp Trp Asn Asp Leu Arg Tyr Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Ser Ile Glu Gln His Leu Gly Thr Ala Leu
            35                  40                  45

Phe Val Gln His Ala Gln Gly Tyr Glu Leu Thr Pro Ala Gly Gln Ala
        50                  55                  60

Leu Leu Lys His Ala Glu
65                  70

```
<210> SEQ ID NO 239
<211> LENGTH: 70
<212> TYPE: PRT
<213> ORGANISM: Pseudomonas putida

<400> SEQUENCE: 239

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Asp Asn Ile Glu Gln Ser Leu Gly Thr Ala Leu
        35                  40                  45

Phe Val Gln His Ala Gln Gly Tyr Glu Leu Thr Pro Ser Gly Gln Ala
    50                  55                  60

Leu Leu Lys His Ala Glu
65                  70

<210> SEQ ID NO 240
<211> LENGTH: 70
<212> TYPE: PRT
<213> ORGANISM: Pseudomonas rhizosphaerae

<400> SEQUENCE: 240

Met Phe Asp Trp Asn Asp Leu Arg Phe Phe Leu Glu Leu Gln Arg Ser
1               5                   10                  15

Gly Arg Leu Leu Thr Ala Ala Lys Arg Leu His Thr Thr His Ser Thr
            20                  25                  30

Val Ala Arg His Ile Glu Ser Ile Glu Gly His Leu Gly Thr Pro Leu
        35                  40                  45

Phe Val Gln Asn Ala His Gly Tyr Glu Leu Thr Pro Ala Gly Gln Thr
    50                  55                  60

Leu Leu Lys His Ala Glu
65                  70

<210> SEQ ID NO 241
<211> LENGTH: 70
<212> TYPE: PRT
<213> ORGANISM: Pseudomonas sp.

<400> SEQUENCE: 241

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Glu Ser Ile Glu Lys Ser Leu Gly Thr Pro Leu
        35                  40                  45

Phe Val Gln His Ala Gln Gly Tyr Asp Leu Thr Pro Ser Gly Gln Ala
    50                  55                  60

Leu Leu Lys His Ala Glu
65                  70

<210> SEQ ID NO 242
<211> LENGTH: 70
<212> TYPE: PRT
<213> ORGANISM: Pseudomonas stutzeri

<400> SEQUENCE: 242

Met Asp Trp Asp Asn Leu Arg Tyr Phe Leu Glu Val Ala Arg Ala Gly
1               5                   10                  15
```

```
Arg Leu Thr Thr Ala Ala Arg Arg Leu Ala Val Asp His Thr Thr Val
            20                  25                  30

Ser Arg Arg Leu Gln Ala Leu Glu Lys Ser Ile Gly Leu Gln Leu Phe
        35                  40                  45

Leu Arg Glu Pro Gly Gly Tyr Lys Leu Thr Glu Ala Gly Arg Asn Leu
    50                  55                  60

Leu Pro Arg Val Glu Ala
65              70

<210> SEQ ID NO 243
<211> LENGTH: 70
<212> TYPE: PRT
<213> ORGANISM: Pseudomonas tolaasii

<400> SEQUENCE: 243

Met Phe Asp Trp Asn Asp Leu Arg Tyr Phe Leu Glu Leu Gln Arg Ser
1               5                   10                  15

Gly Arg Leu Leu Thr Ala Ala Gln Arg Leu Lys Thr Thr His Ala Thr
            20                  25                  30

Val Ala Arg His Ile Glu Ala Ile Glu Lys Ser Leu Gly Thr Ala Leu
        35                  40                  45

Phe Val Gln His Ala Gln Gly Tyr Glu Leu Thr Pro Ala Gly Glu Ala
    50                  55                  60

Leu Leu Lys His Ala Glu
65              70

<210> SEQ ID NO 244
<211> LENGTH: 70
<212> TYPE: PRT
<213> ORGANISM: Pseudomonas umsongensis

<400> SEQUENCE: 244

Met Phe Asp Trp Asn Asp Leu Arg Phe Phe Leu Glu Leu Gln Arg Ser
1               5                   10                  15

Gly Arg Leu Leu Thr Ala Ala Arg Arg Leu Asn Thr Thr His Ala Thr
            20                  25                  30

Val Ala Arg His Ile Glu Ala Ile Glu Lys Ser Leu Gly Thr Ala Leu
        35                  40                  45

Phe Val Gln His Ala Gln Gly Tyr Glu Leu Thr Pro Ala Gly Glu Ala
    50                  55                  60

Leu Leu Lys His Ala Glu
65              70

<210> SEQ ID NO 245
<211> LENGTH: 70
<212> TYPE: PRT
<213> ORGANISM: Pseudomonas veronii

<400> SEQUENCE: 245

Leu Asn Trp Asp Asp Leu Lys Phe Phe Leu Glu Val Ala Arg Thr Arg
1               5                   10                  15

Lys Ala Ser Val Ala Ala Lys Arg Leu Ala Val Asp Tyr Thr Thr Val
            20                  25                  30

Ser Arg Arg Ile Ser Ser Leu Glu Val Ser Leu Gly Thr Leu Leu Phe
        35                  40                  45

Glu Lys Ser Arg Thr Ser Gly Phe Val Leu Thr Asn Glu Gly Gln Arg
    50                  55                  60

Leu Leu Gly Tyr Ala Glu
```

<210> SEQ ID NO 246
<211> LENGTH: 70
<212> TYPE: PRT
<213> ORGANISM: Pseudomonas vranovensis

<400> SEQUENCE: 246

Met Phe Asp Trp Asn Asp Leu Arg Phe Phe Leu Glu Leu Gln Arg Ser
1               5                   10                  15

Gly Arg Leu Leu Thr Ala Ala Lys Arg Leu Asn Thr Thr His Ser Thr
            20                  25                  30

Val Ala Arg His Ile Asp Asn Ile Glu Gln Ser Leu Gly Thr Ala Leu
        35                  40                  45

Phe Val Gln His Ala Gln Gly Tyr Glu Leu Thr Pro Ser Gly Gln Ala
    50                  55                  60

Leu Leu Lys His Ala Glu
65                  70

<210> SEQ ID NO 247
<211> LENGTH: 70
<212> TYPE: PRT
<213> ORGANISM: Pseudomonas xanthomarina

<400> SEQUENCE: 247

Met Asp Trp Asp Asn Leu Arg Tyr Phe Leu Glu Val Ala Arg Ala Gly
1               5                   10                  15

Arg Leu Thr Thr Ala Ala Arg Arg Leu Ala Val Asp His Thr Thr Val
            20                  25                  30

Ser Arg Arg Leu Gln Ala Leu Glu Lys Ser Met Gly Leu Gln Leu Phe
        35                  40                  45

Leu Arg Glu Pro Gly Gly Tyr Lys Leu Thr Glu Ala Gly Arg Asn Leu
    50                  55                  60

Leu Pro Arg Val Glu Ala
65                  70

<210> SEQ ID NO 248
<211> LENGTH: 70
<212> TYPE: PRT
<213> ORGANISM: Pusillimonas sp.

<400> SEQUENCE: 248

Met Leu Asp Trp Asp Gly Leu Arg Tyr Phe Leu Glu Val Ala Arg Thr
1               5                   10                  15

Gln Arg Val Ser Ala Ala Ala Leu Arg Leu Gly Val Arg His Ser Thr
            20                  25                  30

Val Ser Arg Arg Ile His Ala Leu Glu Leu Glu Leu Gly Thr Leu Leu
        35                  40                  45

Phe Asp Lys Ser Lys Ser Thr Gly Phe Thr Leu Thr Glu Glu Gly Asn
    50                  55                  60

Arg Phe Phe Ala Tyr Ala
65                  70

<210> SEQ ID NO 249
<211> LENGTH: 70
<212> TYPE: PRT
<213> ORGANISM: Rhizobium alamii

<400> SEQUENCE: 249

```
Met Asn Trp Asp Asp Val Arg Ile Phe Leu Ala Val Ala Arg Thr Gly
1               5                   10                  15

Gln Ile Leu Ala Ala Ser Lys Arg Leu Gly Leu Asn His Ala Thr Leu
            20                  25                  30

Ser Arg Arg Leu Thr Ser Leu Glu Glu Ala Leu Lys Thr Arg Leu Phe
            35                  40                  45

Ile Arg Arg Thr Asn Gly Cys Glu Leu Thr Ala Glu Gly Ala Val Phe
        50                  55                  60

Leu Ala Ser Ala Glu Arg
65                  70
```

<210> SEQ ID NO 250
<211> LENGTH: 71
<212> TYPE: PRT
<213> ORGANISM: Rhizobium etli

<400> SEQUENCE: 250

```
Met Asn Trp Asp Asp Val Arg Ile Phe Leu Ala Val Ala Arg Thr Gly
1               5                   10                  15

Gln Ile Leu Ala Ala Ser Lys Arg Leu Gly Leu Asn His Ala Thr Leu
            20                  25                  30

Ser Arg Arg Leu Thr Ser Leu Glu Glu Ala Leu Lys Thr Arg Leu Phe
            35                  40                  45

Ile Arg Arg Thr Asn Gly Cys Glu Leu Thr Ala Glu Gly Gly Ile Phe
        50                  55                  60

Leu His Ala Ala Glu Arg Met
65                  70
```

<210> SEQ ID NO 251
<211> LENGTH: 70
<212> TYPE: PRT
<213> ORGANISM: Rhizobium freirei

<400> SEQUENCE: 251

```
Met Asp Trp Asp Asp Val Arg Met Phe Leu Ala Val Ala Arg Thr Gly
1               5                   10                  15

Gln Ile Leu Ala Ala Ser Lys Arg Leu Gly Val Asn His Ala Thr Leu
            20                  25                  30

Ser Arg Arg Val Thr Thr Leu Glu Glu Arg Leu Lys Thr Arg Leu Leu
            35                  40                  45

Val Arg Arg Thr Asn Gly Cys Asp Leu Thr Ala Glu Gly Glu Ile Phe
        50                  55                  60

Leu His Ala Ala Glu Arg
65                  70
```

<210> SEQ ID NO 252
<211> LENGTH: 70
<212> TYPE: PRT
<213> ORGANISM: Rhizobium giardinii

<400> SEQUENCE: 252

```
Met Asn Trp Asp Asp Val Arg Met Phe Leu Ala Val Ala Arg Ser Gly
1               5                   10                  15

Gln Ile Leu Ser Ala Ser Lys Arg Leu Gly Val Asn His Ala Thr Leu
            20                  25                  30

Ser Arg Arg Val Thr Ala Leu Glu Glu Ser Leu Lys Thr Arg Leu Leu
            35                  40                  45

Ile Arg Arg Thr Asn Gly Cys Asp Leu Thr Ala Glu Gly Glu Ile Phe
```

Val His Ala Ala Glu Arg
65              70

<210> SEQ ID NO 253
<211> LENGTH: 70
<212> TYPE: PRT
<213> ORGANISM: Rhizobium leguminosarum

<400> SEQUENCE: 253

Met Asn Trp Asp Asp Val Arg Ile Phe Leu Ala Val Ala Arg Thr Gly
1               5                   10                  15

Gln Ile Leu Ala Ala Ser Lys Arg Leu Gly Leu Asn His Ala Thr Leu
            20                  25                  30

Ser Arg Arg Leu Thr Ser Leu Glu Glu Ala Leu Lys Thr Arg Leu Phe
        35                  40                  45

Ile Arg Arg Thr Asn Gly Cys Glu Leu Thr Ala Glu Gly Glu Val Phe
    50                  55                  60

Leu Ala Ser Ala Glu Arg
65              70

<210> SEQ ID NO 254
<211> LENGTH: 70
<212> TYPE: PRT
<213> ORGANISM: Rhizobium phaseoli

<400> SEQUENCE: 254

Met Asn Trp Asp Asp Val Arg Ile Phe Leu Ala Val Ala Arg Thr Gly
1               5                   10                  15

Gln Ile Leu Ala Ala Ser Lys Arg Leu Gly Leu Asn His Ala Thr Leu
            20                  25                  30

Ser Arg Arg Leu Thr Ser Leu Glu Glu Ala Leu Lys Thr Arg Leu Phe
        35                  40                  45

Ile Arg Arg Thr Asn Gly Cys Glu Leu Thr Ala Glu Gly Gly Val Phe
    50                  55                  60

Leu His Ala Ala Glu Arg
65              70

<210> SEQ ID NO 255
<211> LENGTH: 70
<212> TYPE: PRT
<213> ORGANISM: Rhizobium sullae

<400> SEQUENCE: 255

Met Asn Trp Asp Asp Val Arg Ile Phe Leu Ala Val Ala Arg Thr Gly
1               5                   10                  15

Gln Ile Leu Ala Ala Ser Lys Arg Leu Gly Leu Asn His Ala Thr Leu
            20                  25                  30

Ser Arg Arg Val Thr Ser Leu Glu Gly Ala Leu Lys Ser Arg Leu Phe
        35                  40                  45

Thr Arg Arg Thr Asn Gly Cys Glu Leu Thr Ala Glu Gly Glu Val Phe
    50                  55                  60

Leu Ala Ser Ala Glu Arg
65              70

<210> SEQ ID NO 256
<211> LENGTH: 70
<212> TYPE: PRT
<213> ORGANISM: Simplicispira psychrophila

<400> SEQUENCE: 256

Ile Asn Trp Asp Asn Leu Arg Leu Phe Leu Ala Val Val Arg Ala Gln
1               5                   10                  15

Ser Ala Gln Glu Ala Ala Arg Arg Leu Asn Val Asp His Ser Thr Val
            20                  25                  30

Thr Arg Arg Leu His Arg Leu Glu Lys Glu Leu Gly Thr Gln Leu Phe
        35                  40                  45

Glu Arg Thr Pro Ala Gly His Val Leu Thr Ala Ala Gly His Arg Leu
    50                  55                  60

Leu Glu His Val Glu Arg
65                  70

<210> SEQ ID NO 257
<211> LENGTH: 71
<212> TYPE: PRT
<213> ORGANISM: Sinorhizobium americanum

<400> SEQUENCE: 257

Met Asp Trp Asp Asp Val Arg Val Phe Leu Ala Val Ala Arg Thr Gly
1               5                   10                  15

Gln Ile Leu Ala Ala Ser Lys Arg Leu Gly Ile Asn His Ala Thr Leu
            20                  25                  30

Ser Arg Arg Val Thr Ala Leu Glu Glu Thr Leu Lys Thr Arg Leu Leu
        35                  40                  45

Val Arg Arg Pro Asn Gly Cys Glu Leu Thr Ala Glu Gly Glu Ile Phe
    50                  55                  60

Leu Ser Ala Ala Glu Arg Met
65                  70

<210> SEQ ID NO 258
<211> LENGTH: 70
<212> TYPE: PRT
<213> ORGANISM: Sinorhizobium medicae

<400> SEQUENCE: 258

Met Asn Trp Asp Asp Val Arg Val Phe Leu Ala Val Ala Arg Thr Gly
1               5                   10                  15

Gln Ile Leu Ala Ala Ser Lys Arg Leu Gly Val Asn His Ala Thr Leu
            20                  25                  30

Ser Arg Arg Val Thr Ala Leu Glu Ala Thr Leu Lys Thr Arg Leu Leu
        35                  40                  45

Val Arg Arg Pro Ser Gly Cys Glu Leu Thr Ala Glu Gly Glu Val Phe
    50                  55                  60

Phe Ala Ala Ala Glu Arg
65                  70

<210> SEQ ID NO 259
<211> LENGTH: 70
<212> TYPE: PRT
<213> ORGANISM: Sneathiella glossodoripedis

<400> SEQUENCE: 259

Met Phe Asp Trp Asn Asp Ile Arg Phe Phe Leu Glu Leu Ser Arg Lys
1               5                   10                  15

Gly Arg Leu Thr Glu Val Ala Lys Ala Leu Lys Val Asp His Thr Thr
            20                  25                  30

Val Ser Arg Arg Ile Ser Thr Leu Glu Lys Asn Leu Asp Ala Lys Leu

```
                35                  40                  45
Phe Glu Asn Thr Thr Arg Gly Tyr Val Leu Thr Gln Ala Gly Glu Arg
         50                  55                  60

Leu Leu Thr Gln Ala Glu
 65                  70

<210> SEQ ID NO 260
<211> LENGTH: 70
<212> TYPE: PRT
<213> ORGANISM: Spiribacter sp.

<400> SEQUENCE: 260

Asn Trp Asn Asp Val Lys Val Phe Val Ala Leu Ala Arg His Gly Arg
 1               5                  10                  15

Leu Thr Arg Ala Ala Arg Ala Leu Gly Ile Thr His Val Thr Val Ala
                20                  25                  30

Asn Arg Met Ala Val Leu Glu Gln Ala Leu Glu Thr Gln Leu Leu Arg
            35                  40                  45

His Ser Asp Ser Gly Phe Asp Leu Thr Lys Ala Gly Ala Glu Phe Phe
         50                  55                  60

Arg His Ala Glu Glu Leu
 65                  70

<210> SEQ ID NO 261
<211> LENGTH: 70
<212> TYPE: PRT
<213> ORGANISM: Streptomyces sp.

<400> SEQUENCE: 261

Met Pro Asp Gln Ala Ser Glu Ile Asp Trp Asp Asp Phe Arg Phe Val
 1               5                  10                  15

Leu Ala Ile Val Arg Ser Gly Thr Val Ser Ala Ala Ala Lys Gln Leu
                20                  25                  30

Gly Val Asp His Thr Thr Val Ile Arg Arg Val Asp Arg Leu Glu Arg
            35                  40                  45

Gln Leu Ser Ala Lys Leu Phe Asp Arg Arg Lys Thr Gly Tyr Gln Leu
         50                  55                  60

Thr Glu Ser Gly His Arg
 65                  70

<210> SEQ ID NO 262
<211> LENGTH: 70
<212> TYPE: PRT
<213> ORGANISM: Tistrella mobilis

<400> SEQUENCE: 262

Met Phe Asp Trp Asn Asp Leu Arg Phe Phe Leu Glu Val Ser Arg Arg
 1               5                  10                  15

Gly Arg Leu Val Thr Ala Ala Arg His Leu Ala Val Asp His Thr Thr
                20                  25                  30

Val Ser Arg Arg Ile Gln Ala Leu Glu Glu Arg Met Asn Thr Lys Leu
            35                  40                  45

Phe Asp Arg Thr Pro Ala Gly Tyr Ser Leu Thr Pro Ala Gly Ala Gln
         50                  55                  60

Leu Val Glu Tyr Ala Glu
 65                  70

<210> SEQ ID NO 263
```

```
<211> LENGTH: 70
<212> TYPE: PRT
<213> ORGANISM: Variovorax paradoxus

<400> SEQUENCE: 263

Met Asp Trp Asp Asn Leu Arg Tyr Phe Leu Glu Leu Ala Arg Ser Gly
1               5                   10                  15

Thr Leu Met Ser Ala Ala Arg Arg Leu Glu Val Asp His Thr Thr Val
            20                  25                  30

Ala Arg Arg Ile Gln Ala Leu Glu Lys Glu Val Gly Ala Pro Leu Phe
        35                  40                  45

Ser Arg Glu Ala Gly Gly His Arg Leu Thr Glu Ala Gly Arg Lys Leu
    50                  55                  60

Gln Pro Gln Val Glu Ala
65                  70

<210> SEQ ID NO 264
<211> LENGTH: 70
<212> TYPE: PRT
<213> ORGANISM: Variovorax sp.

<400> SEQUENCE: 264

Met Asp Trp Asp Asn Leu Arg Phe Phe Leu Glu Leu Ala Arg Ser Gly
1               5                   10                  15

Thr Leu Val Gly Ala Ala Arg Arg Leu Ala Val Asp His Thr Thr Val
            20                  25                  30

Ala Arg Arg Ile Gln Ala Leu Glu Lys Arg Val Gly Thr Ala Leu Phe
        35                  40                  45

Ser Arg Glu Ala Asp Gly His Arg Leu Thr Glu Ala Gly Arg Arg Leu
    50                  55                  60

Gln Pro Gln Val Glu Ala
65                  70

<210> SEQ ID NO 265
<211> LENGTH: 70
<212> TYPE: PRT
<213> ORGANISM: Xanthobacter sp.

<400> SEQUENCE: 265

Met Pro Gly Gly Asp Phe Glu Trp Ser Asp Leu Thr Phe Phe Leu Ala
1               5                   10                  15

Val Ala Arg Ala Gly Arg Leu Thr Val Ala Ala Arg Leu Lys Val
            20                  25                  30

Glu His Ser Thr Val Ser Arg Ile Ala Ala Leu Glu Thr Ala Leu
        35                  40                  45

Gly Ala Lys Leu Phe Asp Arg Arg Pro His Gly Tyr Ala Leu Thr Ala
    50                  55                  60

Ala Gly Asp Arg Leu Leu
65                  70

<210> SEQ ID NO 266
<211> LENGTH: 54
<212> TYPE: PRT
<213> ORGANISM: Artificial Sequence
<220> FEATURE:
<223> OTHER INFORMATION: Consensus

<400> SEQUENCE: 266

Met Asp Trp Asp Asp Leu Arg Phe Phe Leu Glu Leu Ala Arg Ser Gly
1               5                   10                  15
```

```
Leu Leu Ala Ala Arg Arg Leu Gly Val Asp His Thr Thr Val Ala Arg
        20                  25                  30

Arg Ile Ala Leu Glu Ala Leu Gly Thr Leu Phe Arg Gly Tyr Leu Thr
         35                  40                  45

Ala Gly Leu Leu Ala Glu
        50
```